United States Patent [19]

Weiner et al.

[11] Patent Number: 5,846,531
[45] Date of Patent: Dec. 8, 1998

[54] MARINE MELA GENE

[75] Inventors: Ronald M. Weiner, Adelphi, Md.; William Claiborne Fuqua, Jr., San Antonio, Tex.

[73] Assignee: University of Maryland, College Park, Md.

[21] Appl. No.: 476,254

[22] Filed: Jun. 7, 1995

Related U.S. Application Data

[63] Continuation-in-part of Ser. No. 148,945, Nov. 8, 1993, Pat. No. 5,474,933, which is a continuation-in-part of Ser. No. 974,837, Nov. 10, 1992, abandoned, which is a continuation of Ser. No. 496,804, Mar. 21, 1990, abandoned.

[51] Int. Cl.$^6$ .............................. A61K 38/44; C12N 9/02
[52] U.S. Cl. ........................... 424/94.4; 435/189; 106/15
[58] Field of Search .................................. 435/69.1, 212, 435/252.3, 252.35, 320.1, 189; 536/22.1, 23.2, 23.1, 23.7; 424/94.4; 106/15

[56] References Cited

U.S. PATENT DOCUMENTS 5,047,344  9/1991  Weiner et al. ........................ 435/252.1

FOREIGN PATENT DOCUMENTS 213 898  3/1987  European Pat. Off. .

OTHER PUBLICATIONS

Michael Wrangstadh et al., "Starvation–specific formation of a peripheral exopolysaccharide by a marine *Pseudomonas* ssp. strain S9", *Biol. Abstr.* 90(6):AB–1060 Abst. No. 67829, 1990.

L. Dagasan et al., "Activity of Cloned Tyrosinas from *Alteromonas colwelliana*", *Abstracts of the Annual Meeting 1989 of Amer. Soc. Microbiol.*, vol. 89, p. 253, Abstr. No. K–50, (1989).

W. C. Fuqua, "Genetic Characterization of the *Alteromonas colwelliana* tyrosinase" *Abstracts of the Annual Meeting 1989 of Amer. Soc. Microbiol.*, vol. 89, p. 185, Abst. No. H–95, (1989).

Marcel Salanoubat et al., "Molecular cloning and sequencing of sucrose synthase cDNA from potato (*Solanum tuberosum L.*): preliminary characterization of sucrose synthase mRNA distribution", *Gene*, vol. 60, pp. 47–56 (1987).

Pamela J. Hanic–Joyce et al., "Molecular Characterization of the Yeast *PRT1* Gene in Which Mutations Affect Translation Initiation and Regulation of Cell Proliferation", The *Journal of Biological Chemistry*, vol. 262, No. 6, pp. 2845–2851 (1987).

A.V. Kaliman et al., "The nucleotide sequence of the region of bacteriophage T5 early genes D10–D–15", *Nucleic Acids Research*, vol. 16, No. 21, pp. 10353–10354 (1988).

Ambaliou Sanni et al., "Structure and Expression of the Genes Encoding the α and β Subunits of Yeast Phenylalanyl–tRNA Synthetase", *The Journal of Biological Chemistry*, vol. 263, No. 30, pp. 15407–15415 (1988).

Peter J. Curtis, "Sequence Comparison of Human and Murine Erythrocyte alpha–spectrin cDNA", *Gene*, vol. 36, pp. 357–362 (1985).

Shigeki Shibahara et al., "Cloning and expression of cDNA encoding mouse tyrosinase", *Nucleic Acids Research*, vol. 14, No. 6, pp. 2413–2426 (1986).

Michael Wrangstadh et al., "The role of an extracellular polysaccharide produced by the marine *Pseudomonas sp.* S9 in cellular detachment during starvation", *Can. J. Microbiol*, vol. 35, pp. 309–312 (1988).

David G. Allison et al., "The Role of Exopolysaccharides in Adhesion of Freshwater Bacteria", *Journal of General Microbiology*, vol. 133, pp. 1319–1327 (1987).

R.R. Read et al., "Purification and characterization of adhesive exopolysaccharides from *Pseudomonas putida* and *Pseudomonas fluorescens*", *Can. J. Microbiol.*, vol. 33, pp. 1080–1090 (1987).

Edward J. Yurkow et al., "Purification of Tyrosinase to Homogeneity Based on its Resistance to Sodium Dodecyl Sulfate–Proteinase K Digestion", *Archives of Biochemistry and Biophysics*, vol. 275, No. 1, pp. 122–129 (1989).

Glen N. Gaulton et al., Control of Tyrosinase Gene Expression and its Relationship to Neural Crest Induction in *Rana pipiens*, *The Journal of Biological Chemistry*, vol. 258, No. 24, pp. 14845–14849 (1983).

William K Fitt, Factors Influencing Bacterial Prouction of Inducers of Settlement Behavior of Larvae of the Oyster *Crassostrea gigas*, *Microb. Ecol.*, vol. 17, pp. 287–298 (1989).

Glover *Gene Cloning* p. 1–19 (1986).

Fugua et al., "The Cloning and Characterization of Marine Bacterial . . ." Annual Meeting of ASM, May 8–13, 1988.

*Primary Examiner*—Charles L. Patterson, Jr.
*Attorney, Agent, or Firm*—Nikaido Marmelstein Murray & Oram LLP

[57] ABSTRACT

The present invention provides the isolated genes encoding marine melA from the genus Shewanella, especially from the species *S. colwelliana,* and the MelA encoded thereby in homogeneous form. Further, the invention provides antibodies to marine MelA as well as methods of using the MelA to induce oyster larval settlement. Moreover, these marine melA genes are also useful as selectable markers for genetic engineering.

7 Claims, 23 Drawing Sheets

```
AAAAACCAGCATCGCGCTGGTTTTTTTTATTGCAGCACAACAATAAACCTCTACACTAGCA  60

CACTTAATTATCTACTCACTGGCCTAACGCTTTCATGTCAGAACATATTCTCATTGCGGT  120

ATTTTTACCGACCTTTTTTTTCGTCTCAATTACACCAGGTATGTGTATGACACTGGCCAT  180
                                              M  T  L  A  M

GACTCTCGGTATGAGTATCGGTGTGCGCCGAACCTTATGGATGATGGTTGGTGAGCTAGC  240
 T  L  G  M  S  I  G  V  R  R  T  L  W  M  M  V  G  E  L  A

AGGCGTTGCCCTCGTGGCGATTGCCGCCGTAATGGGTGTCGCCAGTATGATGCTGAACTA  300
 G  V  A  L  V  A  I  A  A  V  M  G  V  A  S  M  M  L  N  Y

TCCACAACTCTTCGATATTTTAAAATGGGTCGGTGGGCTCTATCTTGGTTACATCGGCAT  360
 P  Q  L  F  D  I  L  K  W  V  G  G  L  Y  L  G  Y  I  G  I

TAGCATGTGGCGGGCCAAAGGGAAAATGGCCAACCTTGACAATACCTCCAGTCAGATCAG  420
 S  M  W  R  A  K  G  K  M  A  N  L  D  N  T  S  S  Q  I  S

TAATCGAGCGCTAATAACTCAAGGCTTTGTCACCGCAATTGCTAATCCAAAAGGCTGGGC  480
 N  R  A  L  I  T  Q  G  F  V  T  A  I  A  N  P  K  G  W  A

CTTTATGATCTCGCTGCTCCCCCCTTTTATCAGCGTTGACCAAGCGATTGCACCACAATT  540
 F  M  I  S  L  L  P  P  F  I  S  V  D  Q  A  I  A  P  Q  L

AATGGTATTACTGTCAATTATTATGATGACAGAGTTCTTCAGCATGCTTGCTTATGCGAG  600
 M  V  L  L  S  I  I  M  M  T  E  F  F  S  M  L  A  Y  A  S

CGGCGGAAAACCCTTAAACTGTTTTTAAGTCGAGGCGATAACATCAAGTGGATGAACCGC  660
 G  G  K  P  L  N  C  F  *

ATAGCAGGGAGTTTAATGATCTGTGTTGGCTTATGGTTGGCGCTAGGTTAACGCAGAGTC  720
```

FIG. 13

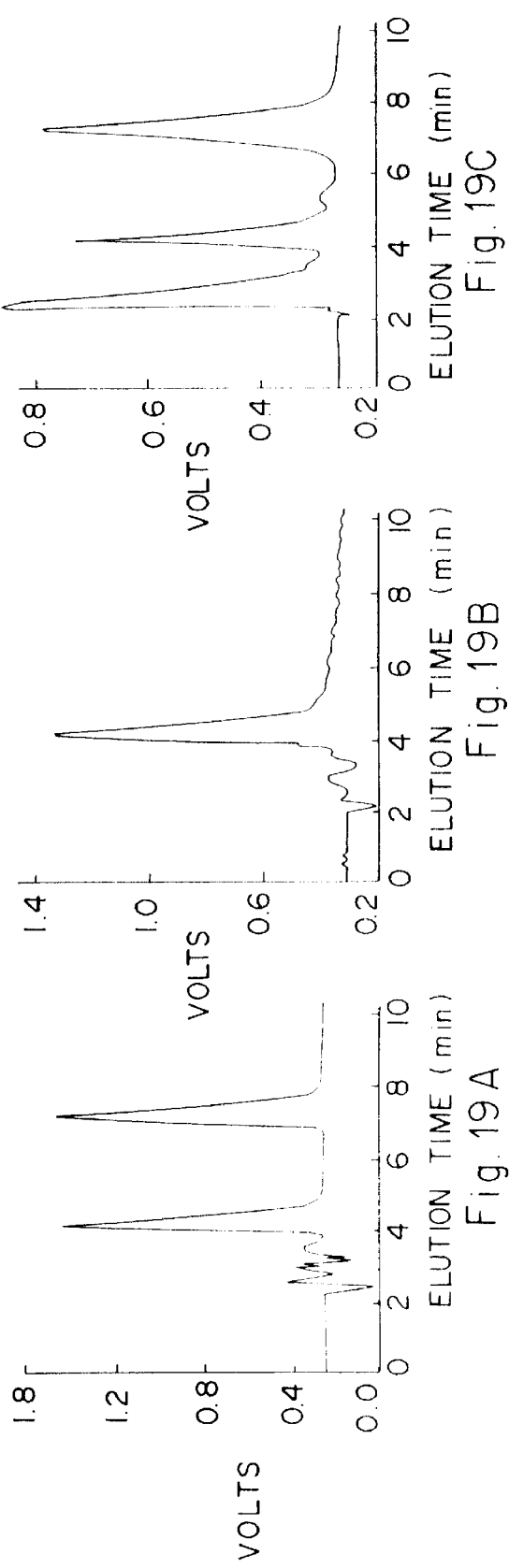

```
         10        20        30        40        50        60
MelA  MASEQNPLGLLGIEFTEFATPDLDFMHKVFIDFGFSKLKKHKQKDIVYYKQNDINFLLNN
       ||:||:|:||:|:|:|:  : :: :|  :||:|  :|: ||:   |:|:;||::|||
pHPPH ADLYENPMGLMGFEFIELASPTPNTLEPIFEIMGFTKVATHRSKDVHLYRQGAINLILNN 70        80        90       100       110
MelA  EKQGFSAQFAKTHGPAISSMGWRVEDANFAFEGAVARGAKPAADEV--KDLPYPAIYGIG
       | :: :: ||  :|||:;::|:;||:|: |:: |:: ||:|  |:   :| ||| |||
pHPPH EPHSVASYFAAEHGPSVCGMAFRVKDSQKAYKRALELGAQPIHIETGPMELNLPAIKGIG 120       130       140       150       160       170
MelA  DSLIYFIDTFGDDNNIYTSDFEALDEPIITQ-EKGFIEVDHLTNNVHKGTMEYWSNFYKD
       :: :|:||  ||:::;||: ||  |::    : |: :||||:||::| |:||:|||::
pHPPH GAPLYLIDRFGEGSSIYDIDFVFLEGVDRHPVGAGLKIIDHLTHNVYRGRMAYWANFYEK 180       190       200       210       220       230
MelA  IFGFTEVRYFDIKGSQTALISYALRSPDGSFCIPINEGKGDDRNQIDEYLKEYDGPGVQH
       :|:| |:||||||||: |:|:| |:  :|||   |:||:::::  :||:|:|:::: |:||
pHPPH LFNFREIRYFDIKGEYTGLTSKAMTAPDGMIRIPLNEESSKGAGQIEEFLMQFNGEGIQH 240       250       260       270       280       290
MelA  LAFRSRDIVASLDAMEGSSIQTLDIIPE-YYDTIFEKLPQVTEDRDRIKHHQILVDGDED
       :||  | :: :: ::: :  :: :::   |: ||: :::|| :  || ||:||:|||
pHPPH VAFLSDDLIKTWDHLKSIGMRFMTAPPDTYYEMLEGRLPNHGEPVGELQARGILLDGSSE 300       310       320       330       340
MelA  G----YLLQIFTKNLFGPIFIEIIQRKNNLGFGEGNFKALFESIERDQVRRGVL
       :    ||||:::|:||:|:|:|||||:: ||||||||||||||||||||||||
pHPPH SGDKRLLLQIFSETLMGPVFFEFIQRKGDDGFGEGNFKALFESIERDQVRRGVLSTD
```

FIG. 21

MARINE MELA GENE

CROSS REFERENCE TO RELATED APPLICATIONS

This application is a continuation-in-part of U.S. application Ser. No. 08/148,945, filed Nov. 8, 1993, now U.S. Pat. No. 5,474,933, which is a continuation-in-part of U.S. application Ser. No. 07/974,837, filed Nov. 10, 1992, now abandoned which is a continuation of U.S. application Ser. No. 07/496,804, filed Mar. 21, 1990 now abandoned.

FIELD OF THE INVENTION

The present invention relates to marine melA genes from *Vibrio cholerae,* the genus Hyphomonas, and in particular the genus Shewanella. Neither the melA or other marine genes that are involved in tyrosine conversion to pigment precursors have heretofore been extensively characterized, and it has been surprisingly found that the melA gene product from *S. colwelliana* differs substantially from that of other known genes involved with tyrosine metabolism, especially as relates to biochemical properties, and primary protein structure.

BACKGROUND OF THE INVENTION

*Shewanella colwelliana* are periphytic, gram-negative marine bacteria originally isolated from the walls of oyster spat tanks. The bacterium, originally designated LST (Lewis Spat Tank isolate), was temporarily assigned to the genus Alteromonas (R. M. Weiner, V. E. Coyne, P. Brayton, P. West, and S. F. Raiken (1988) *Int. J. System. Bact.* 38:240–244), and has now been reclassified to the recently established genus Shewanella (V. E. Coyne, C. J. Pillidge, D. D. Sledjeski, H. Hori, B. A. Ortiz-Conde, D. G. Muir, R. M. Weiner, and R. R. Colwell (1989) *System. Appl. Microbiol.* 12:275–279). These bacteria synthesize melanin, a brown-black polymeric pigment, and melanin metabolite precursors associated with an exopolysaccharide capable of inducing settlement and metamorphosis of oyster larvae, especially *Crassostrea virginica* larvae. Melanin synthesis occurs during late logarithmic and early stationary stages of growth.

Melanin is a general class of dark pigments found in bacteria, fungi, and higher organisms. This broad class of pigment is composed of complex polymers synthesized from phenolic or polyphenolic compounds (A. A. Bell and M. H. Wheeler (1986) *Ann. Rev. Phytopathol.* 24:411–451). The polymer is highly recalcitrant to degradation, and is observed frequently in the environment (i.e., humic soil deposits). Melanin is thought to be a "stable" free radical because it contains semiquinone free radicals that are stabilized by quinone and hydroxyquinone constituents of the polymer (A. A. Bell and M. H. Wheeler (1986) *An. Rev. Phytopathol.* 24:411–451). In addition, due to its complex composition melanin is capable of acting as either an oxidant or a reductant (M. S. Blois (1971) p. 125–139 in T. Kawamura, T. B. Fitzpatrick, and M. Seiji (eds), *Biology of Normal and Abnormal Melanocytes* Univ. Tokyo Press, Tokyo).

The classic Mason-Raper biosynthetic pathway for the synthesis of DOPA melanin was proposed in the late 1920's for one class of melanin (H. S. Raper (1928) *Physiol. Rev.* 8:245–282). In this pathway tyrosine is converted to DOPA via ortho-hydroxylation, and DOPA is then oxidized at both ring hydroxyl groups to form dopaquinone.

Melanogenesis has been documented for a number of bacterial species such as Streptomyces, Bacillus, Rhizobium, Legionella, and Vibrio; from fungi such as Neurospora and mushrooms; from amphibians such as Xenopus; and from mammals such as mice and humans. By far the best studied enzymes known to mediate melanogenesis are the tyrosinases (also known as catechol oxidase, phenolase, and polyphenol oxidase). Some of the genes encoding these tyrosinases have been cloned and sequenced but until the present invention no tyrosinase gene from a gram-negative bacterium or marine microorganism has been cloned or even isolated. In particular, cloned and sequenced tyrosinase genes have been reported from *Streptomyces antibioticus,* from *Streptomyces glaucescens,* from mouse pigment cells, and from human melanocytes [Bernan, V. et al. (1985) *Gene* 37: 101–110; Hintermann, G. et al. (1985) *Mol. Gen. Genet.* 200: 422–432; Shibahara, S. et al. (1986) *Nucleic Acids Res.* 14: 2413–2427; Kwon, B. S. et al. (1987) *Proc. Natl. Acad. Sci. USA* 84: 7473–7477]. Additionally, the protein sequence of the *Neurospora crassa* tyrosinase has been determined [Lerch, K. (1982) *J. Biol. Chem.* 257: 6414–6419].

Almost all genetic investigations in animals have focused on the mouse and human genes. A number of genetic loci have been defined in mice, where the $A^Y$ (lethal yellow) and e (extension) loci affect whether the melanin is black or yellow (sulfhydryl phaomelanin). Other loci, the b (brown), p (pink), and c (albino) appear to modulate the levels of tyrosinase activity in melanocytes (M. Jimenez, K. Tsukamoto, and V. J. Hearing (1991) *J. Biol. Chem.* 266:1147–1156). A gene encoding tyrosinase, corresponding to the b locus, was isolated from a cDNA library generated from B16 mouse melanoma cells (S. Shibahara, Y. Tomita, T. Sakakura, C. Nager, B. Chaudhuri, and R. Muller (1986) *Nucl. Acids Res.* 14:2413–2427). The DNA sequence encoded a protein predicted to be 58 kD after cleavage of a presumptive amino terminal signal sequence, in agreement with size estimates of purified mouse tyrosinase (J. B. Burnett (1971) *Biol. Chem.* 246:3079–3091). However, later studies disputed the authenticity of this clone. A second gene was cloned, that mapped to the c locus, and the authors claimed that the previous b locus gene was actually 5,6-hydroxyindole conversion factor, an accessory protein involved in mammalian melanogenesis (G. Muller, S. Ruppert, E. Schmid, and G. Schutz (1988) *EMBO J.* 7:2723–2730). The c locus gene encoded a protein of 58.5 kD, in general agreement with previous purified size estimates. Supporting these studies, the human tyrosinase gene was isolated from a cDNA library and also mapped to the c locus (B. Kwon, A. Haq, S. H. Pomerantz, and R. Halaban *Proc. Natl. Acad. Sci., USA* 84:7473–7477). Furthermore, individuals with oculocutaneous albinism have been shown to possess a missense mutation in the c locus (L. B. Giebel, K. M. Strunk, R. A. King, J. M. Hanifin, and R. A. Spritz (1990) *Proc. Natl. Acad. Sci., USA* 87:3255–3258).

The b locus and the c locus share a high degree of sequence conservation (86%) and also have the requisite copper-binding motifs of tyrosinases from Neurospora and Streptomyces (G. Muller, S. Ruppert, E. Schmid, and G. Schutz (1988) *EMBO J.* 7:2723–2730; S. Shibahara, Y. Tomita, T. Sakakura, C. Nager, B. Chaudhuri, and R. Muller (1986) *Nucl. Acids Res.* 14:2413–2427). More recent studies have further complicated the issue by revealing that both the b locus and the c locus gene products possess tyrosinase activity, and a locus encoding the TRP2 protein may be a third tyrosinase (M. Jimenez, K. Tsukamoto, and V. J. Hearing (1991) *J. Biol. Chem.* 266:1147–1156). These results suggest that a family of tyrosinases may mediate melanogenesis in mammals, each one functioning in a different aspect of the process. Reflecting this, the b locus protein is preferentially expressed in transformed melanocytes while the c locus is expressed at higher levels in normal melanocytes (M. Jimenez, K. Tsukamoto, and V. J. Hearing (1991) *J. Biol. Chem.* 266:1147–1156). The functions of the p, e, and $A^Y$ loci are yet to be determined but could be involved in regulation of tyrosinase(s).

The Streptomyces tyrosinase is the most extensively studied bacterial melanogenesis system. The ability to synthesize melanin is highly unstable and spontaneous mutants arise frequently (H. Schrempf (1983) *Mol. Gen. Genet.* 189:501–505). Two classes of mutants have been defined, Class I mutants defective in tyrosinase activity, and Class II mutants defective in tyrosine secretion (R. R. Crameri, L. Ettlinger, R. Hutter, K. Lerch, M. A. Suter, and J. A. Vetterli (1982) *J. Gen. Microbiol.* 128:371–379). Neither of these mutants demonstrated any detrimental effects from loss of melanin synthesis, suggesting that the gene was nonessential for growth in laboratory culture. The Class I mutants were further divided into three genetic loci mutable for tyrosinase gene expression (R. Crameri, G. Hintermann, R. Hutter, and T. Keiser (1984) *Can. J. Microbiol.* 30:1058–1067). The melA and melB loci were thought to be genes involved in the regulation of melanogenesis and melC the tyrosinase structural gene.

The tyrosinase genes for two species, *S. glaucescens* and *S. antibioticus* have been cloned and sequenced (V. Bernan, D. Filpula, W. Herber, M. Bibb and E. Katz (1985) *Gene* 37:101–110; G. Hintermann, M. Zatchez, and R. Hutter (1985) Mol. Gen. Genet. 200:422–432; M. Huber, G. Hintermann, and K. Lerch (1985) *Biochemistry* 24:6038–6044; E. Katz, C. J. Thompson, and D. A. Hopwood (1983) *J. Gen. Micro.* 129:2703–2714) and are the only bacterial melanogenesis genes reported to be cloned. The cloned fragments correspond to the melC locus defined in the earlier mutational analyses.

The role of melanin as an oxygen/free radical sink is an attractive hypothesis long proposed as a function for the polymer (A. A. Bell and M. H. Wheeler (1986) *Ann. Rev. Phytopathol.* 24:411–451). Most melanin synthesis systems, including those in Streptomyces, are dispensable for growth in the laboratory (H. Schrempf (1983) *Mol. Gen. Genet.* 189:501–505). Melanization may act as an oxygen/free radical sink, involved in coping with oxygen and oxidative stress. It is possible that other melanizing bacteria also benefit from the trapping of free radicals and/or the increased oxygen demand during melanin polymerization.

When *S. colwelliana* D is grown on marine agar plates, the melanin diffuses outward from the colonies. Production is greatly enhanced by the addition of tyrosine, suggesting that the pigment is derived from tyrosine metabolism (Fuqua et al, *J. Gen. Microbiol.* 139:1105–1114 (1993)).

Some *Pseudomonas aeruginosa* strains produce melanin-like pigments when grown on peptone agar. (*Pigment Microbiology*, P. X. Margalith, ed. Chapman & Hall, pp. 11–13 (1992)). This would not take place in tyrosine-free media. Since tyrosinase inhibitors (KCN, $Na_2S$) are without effect and DOPA can not be identified in culture extracts, there are doubts with regard to the identity of the pigment. All melanin-forming strains have been found to accumulate homogentisic acid (2,5-dihydroxyphenylacetic acid), while melanin negative strains do not. It has been argued that the melanin strains were not tyrosinase-positive, but rather mutants defective in the metabolism of homogentisic acid. Under oxidative conditions in the presence of amino acids this was polymerized into a brown aeruginosa melanin. A similar brown pigment was shown to be produced by strains of *Serratia marcescens* when cultivated on tyrosine.

In this organism, melanogenesis is mediated primarily by MelA, the product of the melA gene. (Fuqua et al, *Gene*, 109:131–136 (1991); Fuqua et al, *J. Gen. Microbiol.* 139:1105–1114 (1993)). When *E. coli* express the cloned melA gene, they are transformed to a melanogenic phenotype, which is again enhanced by tyrosine in the medium (Fuqua et al, *Gene* 109:131–136 (1991); Fuqua et al, *J. Gen. Microbiol.*, 139:1105–1114 (1993)). Analysis of lysates of *S. colwelliana* D and transformed *E. coli* demonstrate the accumulation of a dominant, electrochemically active intermediate, previously referred to as TyrP, (Fuqua, Doctoral dissertation. University of Maryland, College Park (1991)). a primary intermediate in pigment production by *S. colwelliana* D.

There are a variety of known pathways by which tyrosine can be converted to melanin. Melanins comprise a general class of complex, polyphenolic heteropolymers which are found as dark pigments in bacteria, fungi and higher organisms. Eumelanins are black and are synthesized by the classic Mason-Raper biosynthetic pathway in which a tyrosinase converts tyrosine to dihydroxyphenylalanine (DOPA) and then to dopaquinone which then autooxidizes and polymerizes to form eumelanin (Raper, *Physiol Rev.* 8:245–282 (1928)). Phaomelanins are brown, red or yellow pigments that form when dopaquinone reacts with glutathione or cysteine prior to further oxidation and polymerization. Structural analogues of tyrosine, or tyrosine metabolites, may also serve as precursors for eumelanin and phaomelanin synthesis (Bell et al, *Ann. Rev. Phytopathol.* 24:411–451 (1986); Nicolaus, *Melanins,* Mermann, Paris (1968); Prota, *Arch. Biochem. Biophys.* 160:73–82 (1974)). Allomelanins, formed from catechol by a mechanism that is not well characterized, are described primarily from plants, but are also produced by bacteria. Pyomelanins, also called alkaptons, are produced from tyrosine through homogentisic acid (Yabuuchi et al, *Int. J. Syst Bact.* 22:53–65 (1972)). While most melanins fall into these categories, other types of melanins exist. (Bell et al, *Ann. Rev. Phytopathol.* 24:411–451 (1986)).

Bacteria are known to produce phaomelanins (Ivins et al, *Infect. Immun.* 34:895–899 (1981)) and pyomelanins (Yabuuchi et al, *Int. J. Syst Bact.* 22:53–65 (1972)). Melanin synthesis in bacteria has been most intensively studied in *Streptomyces spp.* (Lerch et al, *Eur. J. Biochem.* 52:125–138 (1981); Lerch et al, *Eur. J. Biochem.* 31:427–437 (1972)). These, and other bacteria (Aurstad et al, *Acta Vet. Scand.* 13:251–259 (1972); Pomerantz et al, *Arch. Biochem. Biophys.* 160:73–82 (1988)), synthesize a eumelanin via the action of tyrosinase on tyrosine via the Mason-Raper pathway.

Pyomelanin production via HGA pathway has been reported in several strains of Pseudomonas (Mann, S., *Arch. Mikrobiol.* 65:359–379 (1969); Ogunnariwo, J. et al, *J. Med. Microbiol.* 8:199–203 (1975); Yabuuchi, E. et al, *Int. J. Syst. Bacteriol.* 22:53–64 (1972)), the marine bacteria *S. colwelliana* D (Coon et al, *Appl. Environ. Microbiol.* 60:3006–3010 (1972)), and other prokaryotes (Blakley, *Can. J. Microbiol.* 18:1247–1255 (1972)).

Preliminary experiments into the melanogenic pathway of *S. colwelliana* D indicated that TyrP was not an intermediate in the Mason-Raper melanogenic pathway. For example, TyrP was detected neither as a product of mushroom tyrosinase action on tyrosine, nor when DOPA was oxidized under a variety of conditions. TyrP was not found to coelute with authentic standards of known Mason-Raper intermediates or a multitude of related compounds.

SUMMARY OF THE INVENTION

The present invention provides a marine melA gene from the genus Shewanella. In particular, this gene may be an isolated nucleic acid, preferably DNA, RNA or recombinant DNA. Replicable expression vectors and transformed microorganisms and cells containing the nucleic acids or vectors are also provided. In a preferred embodiment, the invention is directed to the melA gene from S. colwelliana. The melA enzyme gene product encoded by this gene is active in catalyzing production of melanin synthesis as well as components in marine exopolysaccharides. Hence, the cloned gene is useful for increasing melA expression, in turn useful for a variety of purposes including adhesibility of marine exopolysaccharides and inducing oyster larval settlement.

Another aspect of the invention is directed to a marine melA from the genus Shewanella, including the recombinant form of the enzyme and peptide fragments of the protein.

A further aspect of this invention provides antibodies to a marine melA from the genus Shewanella and a method of using these antibodies in an immunoassay for detecting the melA.

Yet another aspect of the subject invention is directed to a method of detecting a melA gene from the genus Shewanella by a hybridization technique or by the polymerase chain reaction (PCR).

A still further aspect of the invention provides the subject melA gene as a selectable marker for genetic engineering.

Another aspect of the invention provides a bioremediation filter containing a mixture of exopolysaccharide, homogentisic melanin and precursors thereof which complex with metals.

Yet another aspect of the invention is to provide a method for complexing metals, including contacting a solution containing the metals with a mixture of exopolysaccharide, homogentisic melanin and precursors thereof.

Yet another aspect of the invention provides for the use of homogentisic melanin in pigments, dyes, and colorings.

Yet another aspect of the invention provides for the use of homogentisic melanin as a UV-blocking agent in sunscreens.

BRIEF DESCRIPTION OF THE DRAWINGS

FIG. 13 is the DNA sequence and predicted amino acid sequence of melA. This figure depicts 720 nucleotides of sequence obtained downstream of melA. The asterisks at the top of the sequence denote each interval of ten nucleotides. Stippling identifies the putative translational start site for mlgA, and the termination codon is indicated under the sequence. [SEQ. ID NOS. 6 & 7]

FIG. 19 shows the production of TyrP by HPLC chromatographs with electrochemical detection. (A) Standard solutions of HGA and 3,4-dihydroxyphenylalanine (DOPA). (B) Supernatant from a culture of S. colwelliana D just prior to pigmentation. (C) Lysate form S. colwelliana D, incubated with tyrosine. (D) Supernatant from PT1 cultured in 4 mM tyrosine in phosphate buffer. (E) Lysate from E. coli transformed with the melA gene from S. colwelliana D, incubated with tyrosine. (F) Lysate from S. colwelliana strain C75 with inactivated melA incubated with tyrosine.

FIG. 21 shows a comparison of the amino acid sequence of MelA, the product of the melA gene in S. colwelliana D against the amino acid sequence of Pseudomonas pHPPH. The comparison was performed by the BestFit subprogram of the GCG software package. Residues connected by a vertical line are identical; residues connected by dots are similar. Residue numbering is relative to the open reading frame of MelA. [SEQ. ID NOS. 10 & 11]

DETAILED DESCRIPTION OF THE PREFERRED EMBODIMENTS OF THE INVENTION

Figure 1:
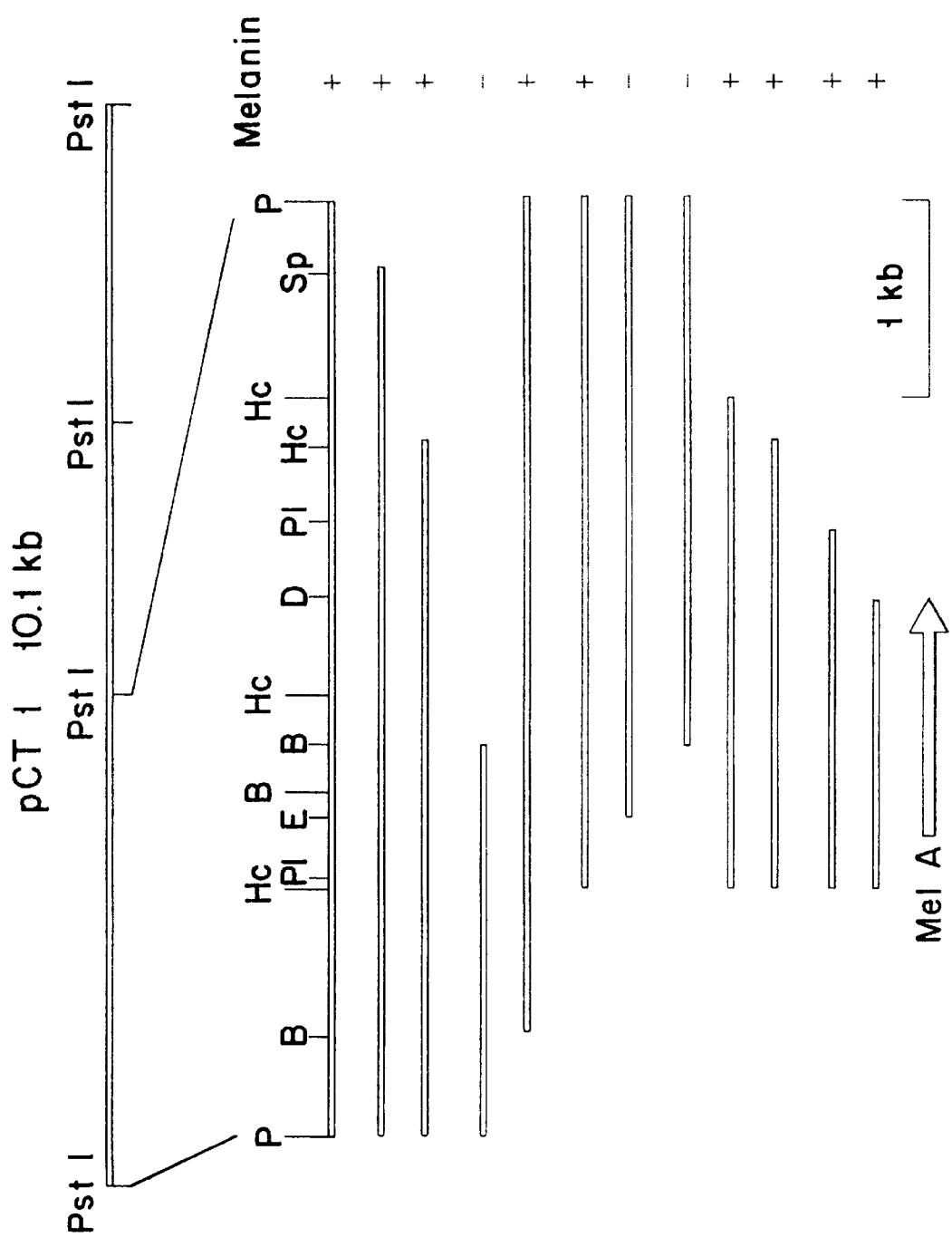
FIG. 1 depicts a restriction map of the 10.5-kb PstI insert in pCT and deletion analysis of pDC1, a plasmid containing a 4.2-kb PstI DNA fragment capable of directing melanin synthesis. The solid lines indicate the DNA fragment present each deletion subclone. The ability of subclones to direct melanin synthesis is indicated with (+), melanin produced, or (−), no melanin produced. Abbreviations: B, BglII; D, DraIII; E, EcoRI; H or Hc HincII; P, PstI; P1, PleI, S; SmaI; Sp, SphI.

The present invention is directed to a marine melA gene, from Vibrio cholerae, the genus Hyphomonas, and particularly the genus Shewanella. S. colwelliana synthesizes a tyrosinase, melB, and a p-hydroxyphenylpyruvate hydroxylase, melA. The melA gene has been cloned, sequenced and found to encode a unique enzyme that alone mediates melanogenesis via an intermediate, Tyr-P which has recently been identified as homogentisic acid (HGA).

The present invention is the first demonstration known to the present inventors that biosynthesis of pyomelanin occurs in the marine bacteria V. cholerae HTX-3 and Hyphomonas MHS-3 PIM, and that it occurs via the HGA pathway. In these two bacteria, as well as S. colwelliana D, the mechanism of pyomelanin synthesis appears to be the derepression of HPPH rather than a mutated downstream enzyme. HGA has commercial uses in dye compositions and as a metal chelator.

A number of functions have been ascribed to bacterial-melanins and their precursors including invertebrate induction (Yvin et al, J. Nat. Prod. 48:814–816 (1985)), invasiveness Soderhall et al, J. Invertebrate Path. 39:105–109 (1982)), virulence (Kwon-Chung et al, J. Bacteriol. 150:1414–1421 (1982)), biofilm adhesiveness (Labare et al, J. Adhes. Sci. Technol. 3:213–223 (1989)), resistance to metals (Nair et al, Wat. Res. 26:413–436 (1992)), and inhibition of biofilm-degrading polysaccharases (Bull, Arch. Biochem. Biophys. 137:345–356 (1970)).

In particular, the melA gene is provided as an isolated nucleic acid from the Shewanella species of S. colwelliana or derivative strain thereof, preferably from *S. colwelliana* strain D, and most preferably strain DYF. The isolated nucleic acid may be provided as a DNA, a cDNA, an RNA, an mRNA or a recombinant DNA.

To clone a Shewanella melA gene, chromosomal DNA from a culture of a Shewanella strain is isolated and subjected to partial digestion with one or more restriction enzymes, usually one. The partially digested DNA is then fractionated on an agarose gel (or by other suitable means, e.g., gel chromatography) and the desired size fragments are eluted from the gel, cloned into a suitable cloning vector, transformed into a host compatible with the selected vector, which host also does not exhibit melanin pigmentation, and plated on selective media to identify dark brown or brown-black colonies containing and expressing the desired melA clone. Once a clone is identified, it can be restriction mapped, sequenced and the coding region determined, for example, by deletion analysis, comparison to other melA genes, protein sequencing, etc. These procedures are suitable for cloning the melA gene from a cultured strain of any Shewanella species. In general, the procedures for isolating DNA, subjecting it to partial digestion, isolating DNA fragments, ligating the fragments into a cloning vector, and transforming a host are well known in recombinant DNA technology. Accordingly, one of ordinary skill in the art can use or adapt the detailed protocols for such procedures as found in Sambrook et al. (1989), *Molecular Cloning: A Laboratory Manual,* 2nd. Ed., Cold Spring Harbor Laboratory, Cold Spring Harbor, N.Y., 3 volumes, or in any of the myriad of manuals on recombinant DNA technology.

Specifically, since *E. coli* does not normally pigment, it is an ideal host for "expression" cloning of the melA gene. For *E. coli,* pigmented colonies are selected by visual inspection of colonies grown on rich agar, e.g., L broth, supplemented with tyrosine and copper. In other hosts, pigmentation (or lack of pigmentation) can be determined by visual inspection of cells or colonies growing on selective media.

When using *E. coli* as the host, an enormous number of cloning vectors are available including pBR322, pBR322-based and related plasmids, bacteriophages and cosmids. The restriction enzyme used for partial digestion should preferably generate a sticky end compatible with a cloning site in the selected vector and not cut in the melA gene. Restriction enzymes which generate blunt-ended fragments can also be used. If compatible ends are not generated or particular restriction sites are desired, linkers may be added to generate the desired compatible restriction site. Linkers are added either to existing sticky-ended fragments, existing blunt-ended fragments or to sticky ends made blunt by appropriate filling reactions.

Because the restriction sites present in the melA gene prior to cloning and analyzing the gene are unknown, a partial enzymatic digestion is performed to ensure production of a large DNA fragment encoding the entire gene. The partial digestion can be repeated one or more times with different enzymes, if difficulties arise in obtaining the necessary fragment. If large enough DNA fragments (10–40 kb) are isolated, there will be a strong probability that a fragment containing the whole melA gene is present in the collection of isolated fragments, especially if two or more partial digests are prepared. In practice, a single partial digestion has generally been sufficient to obtain the desired clone.

The species of the genus Shewanella from which a marine melA gene can be cloned is preferably *S. colwelliana,* however, the gene can also be cloned from other genera including *Vibrio cholera,* Hyphomonas, Pseudomonas and the like. The especially preferred species is *S. colwelliana.* Particular strains of these species which can be cultured to obtain chromosomal DNA include, but are not limited to, *S. colwelliana* strains LST, DYF and HYP accorded ATCC accession numbers 39565, 33887 and 33888, respectively.

The *S. colwelliana* strains, LST, DYF and HYP have been described, including growth conditions therefor, in U.S. Pat. No. 4,740,466 which is incorporated herein by reference. The various strains from the other Shewanella species can also be grown as described for *S. colwelliana* or other known conditions.

The melA gene from any species of the genus Shewanella may be isolated as described above, however, as an alternative, once one melA gene has been obtained, it can serve as a hybridization probe to isolate corresponding melA genes from the other Shewanella species by cross-hybridization under low to moderate stringency conditions. Such conditions are usually found empirically by determining the conditions wherein the probe specifically cross-hybridizes to its counterpart melA gene with a minimum of background hybridization. Nucleic acid hybridization is a well known technique and thoroughly detailed in Sambrook et al.

The *S. colwelliana* melA gene was cloned by the isolating chromosomal DNA from *S. colwelliana* strain LST-DYF, performing a partial digestion with PstI, isolating approximately 35 kb DNA fragments from an agarose gel and ligating them into the cosmid vector pHC79. The constructs were packaged in vitro into phage lambda heads and transduced into *E. coli* recipients. Transductants were transferred onto tyrosinase screening media consisting of L broth supplemented with 5 mg/ml tyrosine and 5 $\mu$g/ml copper and screened for pigmentation properties, i.e., for the appearance of dark brown or brown-black colonies. A single positive clone (out of 600) was selected for analysis by restriction mapping, deletion analysis and sequencing. The nucleotide sequence and translated amino acid sequence for the *S. colwelliana* melA gene is shown below (SEQ ID NO 1)):

10 20 30 40
TGA CTT TAT GAG TCG CAC AGG TAT CGA AGC GGG CTA CAT GAC CTT 50 60 70 80 90
ACA TCA AAA AGG CGT GCC GCA TGG ACC ACA ACC TGG TCG TAC TGA 100 110 120 130
AGC CTC AGT GGG CAA AAC TGA AAC CTA TGA GTA TGC AGT AAT GGT 140 150 160 170 180
GGA CAC CTT TGC ACC ACT GCA ACT GAC CCA GCA TGT CAA TCG TGC

-continued

```
      190            200            210            220
       |              |              |              |
ATG AGC AAA GAT TAC AAC CGT TCC TGG CTA GAA GAG TAA AAG CGT 230            240            250            260            270
       |              |              |              |              |
TCA GCC AGT GCT GAA CAT CTA ATA AAT ATA ACA CCA GAG GTG ACA 280            290            300            310
              |              |              |              |
CCG AAG AGT GCC CTT GGT TGC AAT AAG TTG AAA GAG GAT AAT TAC 320            330            340            350            360
       |              |              |              |              |
ATG GCA AGC GAA CAA AAC CCA CTG GGT CTA CTT GGT ATC GAA TTC
Met Ala Ser Glu Gln Asn Pro Leu Gly Leu Leu Gly Ile Glu Phe 370            380            390            400
              |              |              |              |
ACT GAA TTT GCT ACA CCA GAT CTA GAT TTT ATG CAT AAA GTT TTT
Thr Glu Phe Ala Thr Pro Asp Leu Asp Phe Met His Lys Val Phe 410            420            430            440            450
       |              |              |              |              |
ATC GAC TTT GGT TTC TCA AAA CTT AAA AAA CAC AAG CAG AAA GAT
Ile Asp Phe Gly Phe Ser Lys Leu Lys Lys His Lys Gln Lys Asp 460            470            480            490
              |              |              |              |
ATT GTT TAC TAT AAA CAA AAT GAT ATT AAC TTT TTA CTC AAC AAT
Ile Val Tyr Tyr Lys Gln Asn Asp Ile Asn Phe Leu Leu Asn Asn 500            510            520            530            540
       |              |              |              |              |
GAA AAA CAG GGC TTT TCA GCC CAG TTT GCC AAA ACG CAT GGC CCA
Glu Lys Gln Gly Phe Ser Ala Gln Phe Ala Lys Thr His Gly Pro 550            560            570            580
              |              |              |              |
GCC ATT AGT TCT ATG GGC TGG CGT GTA GAA GAT GCC AAC TTT GCC
Ala Ile Ser Ser Met Gly Trp Arg Val Glu Asp Ala Asn Phe Ala 590            600            610            620            630
       |              |              |              |              |
TTT GAA GGT GCT GTA GCC CGT GGG GCT AAA CCC GCA GCA GAT GAG
Phe Glu Gly Ala Val Ala Arg Gly Ala Lys Pro Ala Ala Asp Glu 640            650            660            670
              |              |              |              |
GTG AAA GAT CTT CCC TAT CCC GCT ATC TAT GGC ATT GGT GAC AGC
Val Lys Asp Leu Pro Tyr Pro Ala Ile Tyr Gly Ile Gly Asp Ser 680            690            700            710            720
       |              |              |              |              |
CTT ATC TAC TTT ATC GAT ACG TTT GGC GAT GAC AAC AAT ATC TAC
Leu Ile Tyr Phe Ile Asp Thr Phe Gly Asp Asp Asn Asn Ile Tyr 730            740            750            760
              |              |              |              |
ATC TCT GAT TTT GAA GCG TTA GAT GAG CCT ATC ATC ACC CAA GAG
Thr Ser Asp Phe Glu Ala Leu Asp Glu Pro Ile Ile Thr Gln Glu 770            780            790            800            810
       |              |              |              |              |
AAA GGC TTC ATT GAG GTC GAC CAT CTC ACC AAT AAT GTC CAT AAG
Lys Gly Phe Ile Glu Val Asp His Leu Thr Asn Asn Val His Lys 820            830            840            850
              |              |              |              |
GGC ACC ATG GAA TAT TGG TCA AAC TTC TAC AAA GAC ATT TTT GGC
Gly Thr Met Glu Tyr Trp Ser Asn Phe Tyr Lys Asp Ile Phe Gly 860            870            880            890            900
       |              |              |              |              |
TTT ACA GAA GTG CGT TAC TTC GAC ATT AAG GGC TCA CAA ACA GCT
Phe Thr Glu Val Arg Tyr Phe Asp Ile Lys Gly Ser Gln Thr Ala
```

```
            910                920                930                940
             |                  |                  |                  |
CTT  ATC  TCT  TAC  GCC  CTG  CGC  TCG  CCA  GAT  GGT  AGT  TTC  TGC  ATT
Leu  Ile  Ser  Tyr  Ala  Leu  Arg  Ser  Pro  Asp  Gly  Ser  Phe  Cys  Ile 950                960                970                980                990
       |                  |                  |                  |                  |
CCA  ATT  AAC  GAA  GGC  AAA  GGC  GAT  GAT  CGT  AAC  CAA  ATT  GAT  GAG
Pro  Ile  Asn  Glu  Gly  Lys  Gly  Asp  Asp  Arg  Asn  Gln  Ile  Asp  Glu 1000               1010               1020               1030
             |                  |                  |                  |
TAC  TTA  AAA  GAG  TAC  GAT  GGC  CCA  GGT  GTC  CAA  CAC  TTA  GCG  TTC
Tyr  Leu  Lys  Glu  Tyr  Asp  Gly  Pro  Gly  Val  Gln  His  Leu  Ala  Phe 1040               1050               1060               1070               1080
       |                  |                  |                  |                  |
CGT  AGC  CGC  GAC  ATA  GTT  GCC  TCA  CTG  GAT  GCC  ATG  GAA  GGA  AGC
Arg  Ser  Arg  Asp  Ile  Val  Ala  Ser  Leu  Asp  Ala  Met  Glu  Gly  Ser 1090               1100               1110               1120
             |                  |                  |                  |
TCC  ATT  CAA  ACC  TTG  GAC  ATA  ATT  CCA  GAG  TAT  TAC  GAC  ACT  ATC
Ser  Ile  Gln  Thr  Leu  Asp  Ile  Ile  Pro  Glu  Tyr  Tyr  Asp  Thr  Ile 1130               1140               1150               1160               1170
       |                  |                  |                  |                  |
TTT  GAA  AAG  CTG  CCT  CAA  GTC  ACT  GAA  GAC  AGA  GAT  CGC  ATC  AAG
Phe  Glu  Lys  Leu  Pro  Gln  Val  Thr  Glu  Asp  Arg  Asp  Arg  Ile  Lys 1180               1190               1200               1210
             |                  |                  |                  |
CAT  CAT  CAA  ATC  CTG  GTA  GAT  GGC  GAT  GAA  GAT  GGC  TAC  TTA  CTC
His  His  Gln  Ile  Leu  Val  Asp  Gly  Asp  Glu  Asp  Gly  Tyr  Leu  Leu 1220               1230               1240               1250               1260
       |                  |                  |                  |                  |
CAA  ATT  TTC  ACC  AAA  AAT  CTA  TTT  GGT  CCA  ATT  TTT  ATC  GAA  ATC
Gln  Ile  Phe  Thr  Lys  Asn  Leu  Phe  Gly  Pro  Ile  Phe  Ile  Glu  Ile 1270               1280               1290               1300
             |                  |                  |                  |
ATC  CAG  CGT  AAA  AAC  AAT  CTC  GGT  TTT  GGC  GAA  GGT  AAT  TTT  AAA
Ile  Gln  Arg  Lys  Asn  Asn  Leu  Gly  Phe  Gly  Glu  Gly  Asn  Phe  Lys 1310               1320               1330               1340               1350
       |                  |                  |                  |                  |
GCC  CTA  TTT  GAA  TCG  ATT  GAG  CGT  GAT  CAG  GTG  CGT  CGC  GGC  GTA
Ala  Leu  Phe  Glu  Ser  Ile  Glu  Arg  Asp  Gln  Val  Arg  Arg  Gly  Val 1360               1370               1380               1390
             |                  |                  |                  |
CTC  TAA  CAA  TCA  CCC  AGT  GAT  CCA  ACC  TCA  AAA  AAC  CAG  CAT  CGC
Leu  End 1400               1410               1420               1430
       |                  |                  |                  |
GCT  GGT  TTT  TTT  ATT  GCA  GCA  CAA  CAA  TAA  ACC  TCT  ACA  C
```

A further aspect of the present invention provides the nucleic acids encoding the subject melA genes in replicable expression vectors and transformed hosts containing these vectors. The replicable expression vectors may be used to obtain the polypeptides of the present invention by well known methods in recombinant DNA technology.

The instant replicable expression vectors comprise a nucleic acid encoding the subject melA gene, i.e., the melA coding sequence is operably linked to a nucleotide sequence element capable of effecting expression of the MelA. In particular, the nucleotide sequence elements can include a promoter, a transcription enhancer element, a termination signal, a translation signal, or a combination of two or more of these elements, generally including at least a promoter element.

Replicable expression vectors are generally DNA molecules engineered for controlled expression of a desired gene, especially where it is desirable to produce large quantities of a particular gene product, or polypeptide. The vectors comprise one or more nucleotide sequences operably linked to a gene to control expression of that gene, the gene being expressed, and an origin of replication which is operable in the contemplated host. Preferably the vector encodes a selectable marker, for example, antibiotic resistance. Replicable expression vectors can be plasmids, bacteriophages, cosmids and viruses. Any expression vector comprising RNA is also contemplated.

The replicable expression vectors of this invention can express MelA at high levels. These vectors may be derived from a prokaryotic source or a eukaryotic source but are preferably derived from a prokaryote or lower eukaryote, e.g., yeast or fungi.

Prokaryotic vectors include bacterial plasmids and bacteriophage vectors that can transform such hosts as *E. coli, B. subtilis, Streptomyces spp.* and other microorganisms. Many of these vectors are based on pBR322, M13 and lambda and are well known in the art and employ such promoters as trp, lac, $P_L$, T7 polymerase and the like. Likewise, suitable eukaryotic vectors that function in tissue culture are especially useful, with yeast vectors being contemplated. These vectors include yeast plasmids and minichromosomes, retrovirus vectors, bovine papilloma virus (BPV) vectors, baculovirus vectors, SV40-based vectors and other viral vectors. The cultured cells which serve as the transformed hosts to these vectors are well known in the art and a suitable host for a particular vector can be readily selected by one of ordinary skill in the art. Numerous texts on recombinant DNA techniques are available which describe expression vectors, the control sequences contained therein, and general methodology for making expression constructs. Hence, one skilled in the art has available many choices of replicable expression vectors, compatible hosts, and well-known methods for making and using the vectors.

Another aspect of this invention provides a homogeneous melA protein from the genus Shewanella, and especially as provided by the subject melA genes. Alternatively, melA protein may be derived from the genera Vibrio or Hyphomonas. Moreover, peptides and fragments as well as chemically modified derivatives of this protein are also contemplated.

Purification of the subject MelA proteins from natural or recombinant sources can be accomplished by conventional purification means such as ammonium sulfate precipitation, preferably in the 10–35% fraction, gel filtration chromatography, such as with a Biogel P-100 column, ion exchange chromatography, adsorption chromatography, affinity chromatography, chromatofocusing, HPLC, FPLC as a protein from 39.5 to 42 kD, Rotophor preparative focusing where the protein is predicted to run at 4.4, but runs at approximately 4.6, gel electrophoresis, where the proteins is predicted to run at 39.5 kD but actually runs at about 42.0 kD, and the like. Where appropriate purification steps can be done in batch or in columns. Fractions containing the MelA are identified by production of an enzymatic product, Tyr-P, now identified as homogentisic acid.

Peptide fragments can be prepared by proteolysis or by chemical degradation. Typical proteolytic enzymes are trypsin, chymotrypsin, V8 protease, subtilisin and the like; the enzymes are commercially available, and protocols for performing proteolytic digests are well known. Peptide fragments are purified by conventional means, as described above. Peptide fragments can often be identified by amino acid composition or sequence. Peptide fragments are useful as immunogens to obtain antibodies against the subject marine MelA.

The present invention relates to antibodies to marine MelA from the genera Shewanella, Vibrio, or Hyphomonas and the species described herein. In a preferred embodiment the antibodies are directed to Shewanella MelA, especially produced by *S. colwelliana*. Such antibodies may be monoclonal or polyclonal and are contemplated to be useful in developing detection assays (immunoassays) for marine MelA proteins, monitoring marine MelA and in purifying marine MelA. Thus, in accordance with this invention, an antibody to a marine MelA encompasses monoclonal or polyclonal antibodies to said MelA, especially a marine MelA from the genus Shewanella, or to antigenic parts thereof.

Both polyclonal and monoclonal antibodies to marine MelA are obtainable by immunization of an animal with purified MelA, purified recombinant MelA, fragments of these proteins, or purified fusion proteins of MelA with another protein. In the case of monoclonal antibodies, partially purified proteins or fragments may serve as immunogens. The methods of obtaining both types of antibodies are well known in the art with excellent protocols for antibody production being found in Harlow et al. (1988) *Antibodies: A Laboratory Manual,* Cold Spring Harbor Laboratory, Cold Spring Harbor, N.Y., 726 pp.

Polyclonal sera are relatively easily prepared by injection of a suitable laboratory animal with an effective amount of the purified MelA, or parts thereof, collecting serum from the animal, and isolating specific sera by any of the known immunoadsorbent techniques. Antibodies produced by this method are useful in virtually any type of immunoassay.

Monoclonal antibodies are particularly useful because they can be produced in large quantities and with a high degree of homogeneity. Hybridoma cell lines which produce monoclonal antibodies are prepared by fusing an immortal cell line with lymphocytes sensitized against the immunogenic preparation and is done by techniques which are well known to those who are skilled in the art. (See, for example, Douillard, I. Y. and Hoffman, T., "Basic Facts About Hybridomas", in *Compendium of Immunology,* Vol. II, L. Schwartz (Ed.) (1981); Kohler, G. and Milstein, C., *Nature* 256: 495–497 (1975) and *European Journal of Immunology* 6: 511–519 (1976); Harlow et al.; Koprowski, et al., U.S. Pat. No. 4,172,124; Koprowski et al., U.S. Pat. No. 4,196,265 and Wands, U.S. Pat. No. 4,271,145, the teachings of which are herein incorporated by reference.)

The presence of a marine MelA contemplated herein in a sample, such as a culture supernatant and the like, aquatic animals, in a microorganism, or in any other source suspected to contain the marine MelA, such as a microfouling film or a component of a mariculture operation, can be detected utilizing antibodies prepared as above, either monoclonal or polyclonal, in virtually any type of immunoassay. Likewise, the present antibodies can be used to identify marine microorganisms which have or produce MelA. Accordingly, the present invention provides a method of detecting a marine MelA by the steps of contacting a sample suspected of containing said MelA with an antibody of the invention for a time and under conditions sufficient to form a MelA-antibody complex and subjecting this complex to a detecting means. As well known to one skilled in the art, the time and conditions for immunodetection assays are variable and depend on the particular assay.

A wide range of detection techniques and conditions are available to one skilled in the art as can be seen by reference to U.S. Pat. Nos. 4,016,043, 4,424,279 and 4,018,653 and to Harlow et al. which provides extensive protocols for immunodetection of molecules. These techniques, of course, include both single-site and two-site, or "sandwich" assays, assays of the non-competitive types as well as competitive binding assays, ELISA, radioimmunoassays, immunoprecipitation and immunoblotting (Western blotting). Sandwich assays are commonly used, a number of variations of the technique exist, and all are intended to be encompassed by the present invention.

Direct and indirect immunoassays, i.e., ELISA, immunoblotting and the like, may employ reporter molecules linked to either a primary antibody (direct assay) or a second antibody or antibody-specific protein such as Protein A or Protein G (indirect assay). The primary antibody can be an antibody of the subject invention labelled with the desired reporter molecule.

By "reporter molecule," as used herein, is meant a molecule which, by its chemical nature, provides an identifiable signal to detect antigen-antibody complexes. Detection may be either qualitative or quantitative. The most commonly used reporter molecules are either enzymes, fluorophores, or radionuclide containing molecules (i.e., radioisotopes). In the case of an enzyme immunoassay, an enzyme is conjugated to the antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase, and alkaline phosphatase among others. The substrate to be used with a particular enzyme is generally chosen for the production of a detectable color change upon reaction. For example, p-nitrophenyl phosphate is suitable for use with alkaline phosphatase conjugates; for peroxidase conjugates, 1,2-phenylenediamine, 5-aminosalicyclic acid, or tolidine are commonly used. It is also possible to employ fluorogenic substrates, which yield a fluorescent product rather than the chromogenic substrates noted above. After binding an enzyme-labeled antibody to an antigen or antigen-antibody complex, as appropriate, the excess labeled antibody is washed away, and a solution containing the appropriate substrate is added. The substrate reacts with the enzyme, i.e., the reporter molecule, to give a qualitative visual signal or a quantitative signal which can be assessed to indicate the amount of antigen present in the sample.

Alternatively, fluorescent compounds, such as fluorescein and rhodamine, may be chemically coupled to antibodies without altering their binding capacity. As used in immunofluorescence, when activated by illumination with light of a specific wavelength, a fluorophore-labeled antibody absorbs the light energy, inducing the fluorophore into an excited stated which is followed by emission of light having a characteristic wavelength. Generally, the emitted light is a characteristic color in the visible range and is detectable with a light microscope equipped for immunofluorescence. Fluorescent antibodies are used in sandwich assays, direct and indirect immunoassays as described above, except after washing, the immune complex is exposed to light of the appropriate wavelength, and the fluorescence is observed. Immunofluorescence and enzyme-based immunoassay techniques are both well established in the art and are particularly preferred. However, other reporter molecules, such as radioisotopes, chemiluminescent or bioluminescent molecules, may also be employed. It will be readily apparent to the skilled technician how to vary the procedure to suit the required purpose.

Another aspect of the invention provides a means of purifying a marine MelA of the genera Shewanella, Vibrio, or Hyphomonas by affinity selection. This method involves contacting a sample containing the MelA with an antibody of the invention, and separating the antigen-antibody complex, e.g., the MelA-antibody complex from the remainder of the sample and recovering the MelA in a form free from the antibody. Typically the complex-containing sample is fractionated and the fraction(s) containing MelA are identified by a convenient biochemical, enzymatic, immunological or other detection means. To facilitate fractionation, the subject antibodies can be bound to a chromatography resin before or after binding to the MelA. This method can yield purified MelA in large amounts and in pure form.

Accordingly, the present invention is also directed to a kit for the rapid and convenient assay of a marine MelA, especially from *Shewanella sp., Vibrio sp.,* or *Hyphomonas sp.* in samples suspected of containing marine MelA. The kit is compartmentalized to receive a first container adapted to contain a molecule capable of detecting the antibody of the first container, wherein the molecule is Protein A, Protein G, an antibody against the antibody of the first container, or a second antibody against said MelA or to an antigenic component thereof, said molecule being labeled with a reporter molecule capable of giving a detectable signal as hereinbefore described. If the reporter molecule is an enzyme, then a third container adapted to contain a substrate for said enzyme is provided. In an exemplified use of the subject kit, a sample to be tested for a marine MelA is contacted with the contents of the first container for a time and under conditions for the MelA, if present, to bind to the antibodies in the first container. The time and conditions are determined by the particular immunoassay which is employed as described herein. After removal of unbound material (e.g., by washing with sterile phosphate buffered saline) the contents of the second container is contacted with the sample being tested. If the MelA has bound to the antibodies of the first container, the detecting molecule of the second container will bind to the secondary complex to form a tertiary complex, and since said the detecting molecule is labeled with a reporter molecule, when subjected to a detecting means, the tertiary complex is detected.

Another aspect of the present invention is directed to a method of detecting the subject marine MelA by nucleic acid hybridization techniques such as Southern blotting, Northern blotting and the like, or by the polymerase chain reaction (PCR). Accordingly, a method of detecting a marine MelA from the genus Shewanella is provided which comprises contacting a sample suspected of containing said melA with a first nucleic acid sufficiently complementary to hybridize to a second nucleic acid which encodes said MelA in said sample for a time and under conditions sufficient to effect said hybridization and thereby form a complex of said first and second nucleic acids and subjecting said complex to a detecting means. In this method, the first nucleic acid may have a reporter group attached thereto. Reporter groups can include radioisotopes, enzymatically detected groups such as biotin or fluorophores such as rhodamine and fluorescein. Detailed methods for hybridization and blotting are found in Sambrook et al.

For PCR, the present method of detecting a marine melA gene from the genus Shewanella comprises subjecting a sample suspected of containing said melA to a polymerase chain reaction (PCR) using at least two oligonucleotide primers sufficiently complementary to hybridize to a nucleic acid in said sample which encodes said MelA, and thereby producing at least one amplified melA nucleic acid segment and identifying said segment. PCR has been described in U.S. Pat. Nos. 4,683,195, 4,683,202, and 4,800,159 which are incorporated herein by reference as well as described extensively in the literature, see for example Saiki et al. (1988), *Science* 239: 487–491. The segment may be detected by gel electrophoresis or blotting, for example.

In the above PCR and hybridization methods, the sample in which the melA gene is to be detected may be a microorganism, a culture of microorganisms, a culture supernatant, a cell extract, seawater, a microfouling film, a component of a mariculture operation and the like.

This invention further provides a method of inducing larval oyster settlement which comprises exposing oyster larvae to a transformed microorganism or cell, in an aqueous environment wherein the microorganism or cell is expressing an active marine MelA from the genus Shewanella and thereby producing metabolites which induce said oyster settlement. MelA induces cementation in biofilms, and the other melanogenic gene in the bacterium, MelB, synthesizes DOPA which induces oyster search behavior.

In one particular embodiment of this invention, each of the transformed microorganisms, cells or their variants can be employed in a process for inducing the settlement and metamorphosis of *Crassostrea virginica* larvae. The Shewanella strain D may also be used alone. Accordingly, the transformants are cultured in a growth medium and provided with a suitable surface material to which they can affix due to the production of an acid polysaccharide exopolymer. Oyster larvae are simultaneously or thereafter exposed to the transformants or, alternatively, to their melanin or melanin precursor metabolic products including melanin, phaomelanin, DOPA, or mixtures thereof for a time and under conditions to effect larvae setting. Once settlement occurs, metamorphosis, i.e., maturation of the oyster larvae, naturally progresses in response to the microcolonies of transformants which can develop on the provided surface material. Oyster larvae settlement may be induced by a combination of microorganisms such as the subject transformants and a Shewanella species, e.g., *S. colwelliana*, preferably strain D.

This invention also relates to a method of improving adhesion of an exopolysaccharide comprising contacting said exopolysaccharide with a marine MelA from the genus Shewanella for a time and under conditions sufficient to impart greater adhesibility of said exopolysaccharide. For example, a purified preparation of exopolysaccharide or exopolysaccharide with altered and useful metal binding properties, especially purified polysaccharide adhesive viscous exopolymer (PAVE) from a marine microorganism, is contacted with a solution or other preparation containing the MelA until the desired viscosity is effected.

A marine melA gene from the genus Shewanella may readily serve as a selectable, phenotypic marker for cloning experiments because its expression imparts an easily recognized phenotype, darkly pigmented colonies. Cloning via insertional inactivation of melA results in loss of pigmentation. Accordingly, this invention provides the subject melA genes as selectable markers for prokaryotes and eukaryotes, preferably for prokaryotes and lower eukaryotes such as yeast and fungi. melA is efficiently expressed in Gram-negative bacteria from its own promoter, and can be used, therefore, under control of its own promoter in most prokaryotic organisms employed as cloning hosts.

Moreover, it is straightforward to determine whether the melA promoter functions in other prokaryotes or eukaryotes by a simple screening test (see below for details), allowing one skilled in the art to adapt the melA gene to different systems. If it is found that melA is not expressed in a particular host, then the gene is placed under control of another promoter capable of directing transcription in that host. Juxtaposition of the melA coding sequence with an appropriate promoter, preferably a constitutive promoter, is accomplished by standard recombinant DNA techniques, e.g., using convenient restriction sites, if available, or introducing needed sequences and sites via linkers, large oligonucleotides or by site-directed mutagenesis.

Insertional inactivation as used herein is disruption of gene expression by insertion of a DNA fragment into a gene present on a cloning vector. In general, the DNA fragment is inserted into the coding sequence of the gene product so that no functional gene product will be translated; however, transcriptional disruption also leads to loss of gene expression so that the DNA fragment could be inserted into the promoter or other upstream sequences required for gene expression. Thus, a selectable marker for insertional inactivation must have at least one unique restriction site, into which a DNA fragment can be inserted and that creates a concomitant loss of marker phenotype. It is advantageous though not absolutely essential that the restriction site be unique with respect to the cloning vector containing the selectable marker. For the melA gene this can be an existing restriction site, e.g., ScaI at nucleotide 989, or can be a genetically-engineered restriction site prepared by known methods such as site-directed mutagenesis. Unique restriction sites can generally be introduced into the coding sequence of a gene without changing amino acid sequence (because of degeneracy in the genetic code) or with a minor sequence change that does not effect activity. Cloning vectors can be constructed which contain melA alone or with one or more other selectable markers, typically one, such as genes encoding drug resistance, nutritional requirements or other selectable phenotype.

Detection of pigmentation (or loss of pigmentation) is simple and inexpensive, merely requiring visual inspection of colonies grown on a rich medium supplemented with tyrosine and copper. Pigmented colonies appear as dark brown-black or brown colonies, whereas unpigmented colonies have a normal appearance, for example, a creamy-whitish color for *E. coli* and many other microorganisms, yeast, and cultured cells.

This invention further relates to the use of MelA (homogentisic melanin) as a ultraviolet (UV) - blocking agent in sunscreens, pigments, dyes, and colorings. These products are useful in cosmetic applications, as tints for glass (e.g., eyeglasses, contact lenses, windows, etc.), and in paints and coatings for plastics, synthetic resins and fabrics, rubber, and wood.

Ultraviolet radiation has a wavelength of 290–400 nm (UV-A=320–400 nm; UV-B=290–320). Melanin is known to (a) scatter and degrade UV radiation to heat, (b) absorb UV radiation and promote immediate oxidation reaction, and (c) quench free radicals generated by UV radiation. Because of its polyquinoid structure melanin acts as an electron exchange polymer and therefore is capable of undergoing rapid photooxidation upon exposure to UV radiation.

The composition of the present invention comprises MelA in an amount needed to provide desired protection against the harmful effects of UV radiation. The concentration of MelA is regulated such that when the composition is topically applied, the desired protection is provided. Preferably MelA is incorporated in an amount ranging from 0.1%–50% w/w, more preferably 1.0–30% w/w, still more preferably 1.5%–15% w/w. Sunscreen compositions comprising MelA will typically have sun protective factors from 1 to 30.

MelA has an absorbance maximum of 263 nm; as such, it is primarily useful as a UV-B absorber. Accordingly, the MelA may be combined in the composition of the present invention with other sunscreen compounds, particularly UV-A absorbing agents. The most widely used chemical sunscreens contain para-aminobenzoic acid (PABA), PABA esters (amyldimethyl PABA and octyldimethyl PABA), benzophenones (oxybenzone and sulisobenzone), cinnamates (octylmethoxy cinnamate and cinoxate), salicylates (homomenthyl salicylate), and anthranilates. To date, more than 21 such chemicals have been declared by the U.S. FDA as safe, effective agents in protecting skin against sunburn (see Table 1), and are listed under Category I (safe and approved).

TABLE 1

SUNSCREEN AGENTS

| Compound | Dose limits, % |
| --- | --- |
| p-aminobenzoic acid | 5.0–15.0 |
| glyceryl aminobenzoate | 3.0–5.0 |
| amyl p-dimethylamino benzoate (Padimate A) | 1.0–5.0 |
| 2-ethylhexyl-p-dimethylamino benzoate (Padimate O) | 1.4–8.0 |
| 2-ethoxy-ethylhexyl-p-methoxy cinnamate (cinnoxate) | 1.0–3.0 |
| diethanolamine-p-methoxycinnamate | 8.0–10.0 |
| ethylhexyl-p-methoxycinnamate | 2.0–7.5 |
| 2,2-dihydroxy-4-methoxybenzophenone (dioxybenzone) | 3.0 |
| 2-hydroxy-4-methoxybenzophenone (oxybenzone) | 2.0–6.0 |
| 2-hydroxy-4-methoxybenzophenone-5-sulfonic acid (sulisobenzone) | 5.0–10.0 |
| 2-ethyl-hexyl-2-cyano-3,3-diphenylacrylate | 7.0–10.0 |
| ethyl-4-bis-(hydroxypropyl)-amino benzoate | 1.0–5.0 |
| digalloyl trioleate | 1.0–5.0 |
| 2-ethylhexyl-salicylate | 3.0–5.0 |
| lawsone + dihydroxyacetone | 0.25–3.0 |
| 3,3,5-trimethylcyclohexyl salicylate (homosalate) | 4.0–15.0 |
| methylanthranilate | 3.5–4.0 |
| 2-phenyl-benzimidazole-5-sulfonic acid | 1.0–4.0 |
| triethanolamine salicylate | 5.0–12.0 |
| red veterinary petrolatum | 30.0–100 |
| titanium dioxide | 2.0–25.0 |

Several European sunscreen manufacturers often use p-methoxy-2-ethylhexylcinnamate, 2-phenylbenzimidazole-5-sulfonic acid, 2-phenyl-5-methoxybenzophenone, and 4-tert-butyl-4'-methoxy-dibenzoylmethane as ultraviolet A and B absorbing filters. The recommended concentration for each chemical may vary and is based on not only the solubility of the chemical in a given vehicle, but also the anticipated use of the sunscreen product as a total or partial block for the prevention of sunburn or acquisition of suntan responses. The formulation base (vehicle) used include alcohol plus glycerol or glycol, oil-in-water or water-in-oil lotion, cream, or ointment. The vehicle in which the ultraviolet radiation absorbing chemical is incorporated can determine whether a sunscreen remains effective under the general use condition involving prolonged sunbathing, sweating (sporting activities), and swimming. This adherent property to skin, known as "substantivity," varies considerably among commercially available sunscreen formulations, some of which are retained on the skin and others of which are washed off easily after sweating or swimming.

Acceptable carriers include any vehicle or medium capable of incorporating the MelA in a manner permitting uniform topical application. The carrier may comprise a wax, oil, or cream base material in which the melanin may be held in a clear solution or a uniform dispersion, for example as submicron sized particles. Preferably the carrier comprises a suitable solvent or mixture of solvents capable of dissolving MelA to provide a concentration that is effective as a filtering agent when incorporated in the sunscreen formulation. For those not skilled in the art, reference is made to the text entitled *Remington's Pharmaceutical Sciences*, 17th edition, 1985, ed. Alfonso R. Gennaro, Mack Publishing Company, Easton, Pa. 18402.

Solvents for use in accordance with the invention include, for example, ethanol, isopropyl alcohol, benzyl alcohol, oils, distilled and/or deionized water, physiological saline solution and the like. The specific solvent chosen will depend on the method of application. Solvents are considered useful only if they do not permanently interact with the MelA to shift the total effective absorption outside the 290–420 nm range.

The primary uses of sunscreens are to prevent sunburn and aid in the development of a tan. Secondarily, they serve to protect exposed areas of the body in susceptible individuals from the long-term hazards of skin cancer and premature aging. In addition, sunscreens can be used to protect against drug-related ultraviolet-induced photosensitivity.

For purposes of the present invention, the term "sunscreen agent" shall refer to the use of MelA as a sunscreen-sunburn preventive agent, a sunscreen-suntanning agent and/or a sunscreen-opaque sunblock agent. Each of those type of agents has been defined by the FDA advisory review panel as nonprescription topical analgesic, antirheumatic, otic, burn and sunburn prevention and treatment drug products as follows:

A sunscreen-sunburn preventive agent contains an active ingredient that absorbs 95% or more of the radiation in the ultraviolet range at wavelengths from 290–320 nm and thereby removes the sunburning rays;

A sunscreen-suntanning agent contains an active ingredient that absorbs at least 85% of the radiation in the ultra-violet range at wavelengths from 290–320 nm, but transmits ultraviolet wavelengths longer than 320 nm (such agents permit tanning in the average individual and also permits some erythema without pain);

A sunscreen-opaque sunblock agent has an opaque agent that reflects or scatters all radiation in the ultraviolet and visible range from 290–777 nm and thereby prevents or minimizes suntan and sunburn.

The following pharmaceutically acceptable topical ingredients are present in commercial sunscreens or sunblocks:

titanium dioxide, petrolatum, red petrolatum, benzophenone-3, isopropyl myristate, aloe vera extract, synthetic beeswax, cetyl palmitate, ceresin, lanolin, cetyl alcohol, alcohol, oleth-3 phosphate, synthetic spermaceti, glycerin, mineral oil, lanolin alcohol, cetyl stearyl glycol, lanolin oil, triethanolamine, carbomer 934, benzyl alcohol, menthol, camphor, essential oils, acrylic-acrylate copolymer, ammonium hydroxide, carbomer 934P, dimethicone, quaternium-15, stearic acid, stearyl alcohol, water, xanthan gum, SD alcohol 40, animal protein derivative, hydroxyethyl cellulose, choleth-24, hydroxypropyl cellulose, PPG-15 stearyl ether, propylene glycol dioctanoate, stearic acid, ozokerite, PEG-4 dilaurate, propylparaben, dihydroxyacetone, hydrocarbon oil, ointment base zinc oxide, opaque base, water-repellent cream base, caramel, perfume and flavors.

It would be advantageous for the topical composition of the present invention to have sufficient substantivity to withstand exposure of the skin to swimming, high humidity and sweating.

Generally, sunscreens should be applied approximately 30 minutes before exposure to the sun. However, there are exceptions, for instance, aminobenzoic acid and its esters are more effective if applied two hours before exposure. Preapplication of the topical MelA composition prior to sun exposure to the skin is advantageous because it allows the MelA to penetrate and perhaps bind with the skin.

The sunscreening compositions may be applied as a clear liquid or a lotion comprising a water-in-oil, oil-in-water or a multiple emulsion. Either the oil or water base or both may be used as a carrier for the sunscreen composition. The oil base material and the water and oil base compositions will form a continuous film of MelA. The physiologically acceptable (i.e., dermatologically innocuous to mammals) compositions herein disclosed are included in a thin-layer protective coating on the skin of mammals, provide long lasting protection against erythema (i.e., sunburn) and do not appreciably decompose over practical periods of exposure to sunlight.

It may also be desirable to add a preservative to the inventive compositions if they are to be used for topical applications. The preferred mode of administration of the inventive compositions is topical administration. Still further, the MelA of the present invention may be combined with substances that stimulate the pigmentary system under conditions of low levels of UV light.

Further, the sunburn/sunscreen product of the present invention may include a burn or sunburn treatment component such as an anesthetic, antimicrobial or another ingredient.

The anesthetic component of commercial products may include, but is not limited to, benzocaine, lidocaine hydrochloride, butamben picrate, dibucaine, tetracaine hydrochloride, tripelennamine, and menthol benzocaine.

The antimicrobial component of commercial products may include, but is not limited to, benzethonium chloride, benzalkonium chloride, povidone-iodine, chloroxylenol, chlorobutanol, 8-hydroxyquinoline, phenol, 8-hydroxyquinoline sulfate, cresol-camphor complex, chlorothymol, methylbenzethonium chloride, triclosan, benzyl alcohol, and parahydracin.

When used in pigments, dyes and other industrial formulations, the color of the MelA-containing product can be varied between black, brown, red and yellow by varying the concentration of MelA (i.e., decreases in melanin concentration result in lightening of the color of the product), reacting the melanin with sulfhydryl-containing compounds, or various metals such as, but not limited to, $Cu^{2+}$, $Ni^{2+}$, and $Co^{2+}$ or by altering the pH of the pigment.

In the case that the MelA compositions are used as tinting agents for glass and plastic or as industrial product protecting agents, e.g., for protection against UV degradation, the compositions may be incorporated directly into the glass or plastic or industrial product. For such uses the carriers, diluents, or the like, would not have to be physiologically acceptable. Other conventional agents for such uses could be formulated therewith.

Having now generally described this invention, the same will be better understood by reference to certain specific examples, which are included herein for purposes of illustration only and are not intended to be limiting of the invention or any embodiment thereof, unless so specified.

EXAMPLE 1

Materials and Methods

A. Media: Selection medium for isolating melA positive clones in *E. coli* consisted of L broth agar supplemented with 5 mg/ml tyrosine and 5 µg/ml copper. *Shewanella sps.* were maintained on marine agar 2216 (Difco).

B. Recombinant DNA Techniques: Standard protocols for DNA cloning and analysis were employed (Sambrook et al.). Restriction enzymes, ligase and other enzymes were used according to manufacturer's instructions.

EXAMPLE 2

Cloning of the *S. colwelliana* melA Gene

*S. colwelliana* LST chromosomal DNA was partially digested with the restriction endonuclease PstI and fragments of approximately 35 kb were isolated. These fragments were annealed into the cosmid vector pHC79 which were packaged in vitro into phage lambda heads and transduced into *E. coli* recipients. Transductants were screened for MelA activity by assessing pigment properties. Out of 600 transductants, one clone was isolated which exhibited heavy pigment production, similar to pigment production in *S. colwelliana*. This clone was designated pCT and a 4.2-kb PstI fragment was subcloned into pUC19 to generate plasmid pDC1. To verify that the insert in clone pCT derived from *S. colwelliana* DNA, chromosomal *S. colwelliana* DNA was extracted from the cells and analyzed by Southern blotting using pDC1 or the pDC1 *S. colwelliana* insert as the hybridization probe.

The DNA insert in pCT encoding the melA gene was determined to be 10.5 kb and a restriction map of the insert was constructed (FIG. 1). Pigment production in pDC1 was not affected when the insert was cloned in either orientation, indicating that expression of the melA gene was initiated from an *S. colwelliana* promoter within the insert.

EXAMPLE 3

Analysis of the *S. colwelliana* melA Gene

The 10.5-kb PstI insert was subjected to deletion analysis to localize the region encoding the melanin gene (melA). Specific restriction fragments were deleted and the resulting plasmids were tested for pigment production on agar plates. A 4.2-kb PstI fragment in plasmid pDC1 directed melanin synthesis and was subjected to still further analysis (FIG. 1). One of the smaller restriction fragment directing melanin synthesis was a 1.9-kb HincII fragment from the plasmid designated pMC3A. The location of the melA open reading frame is indicated at the bottom of FIG. 1; SEQ ID NO.2 provides the nucleotide sequence of approximately 1.4 kb of the pMC3A HincII fragment and the translated melA amino acid sequence which lies between nucleotide 316 and nucleotide 1425.

To further characterize the gene product encoded by these plasmids, proteins were synthesized using a DNA directed translation system. The *S. colwelliana* MelA has an apparent molecular weight ($M_r$) of 42,000 as determined by SDS-PAGE analysis and a calculated molecular weight of 39,453 daltons. Interruption of the coding sequence at restriction sites which caused loss of pigmentation also caused the loss of this protein.

EXAMPLE 4

Production of MelA Antibodies

Figure 2:
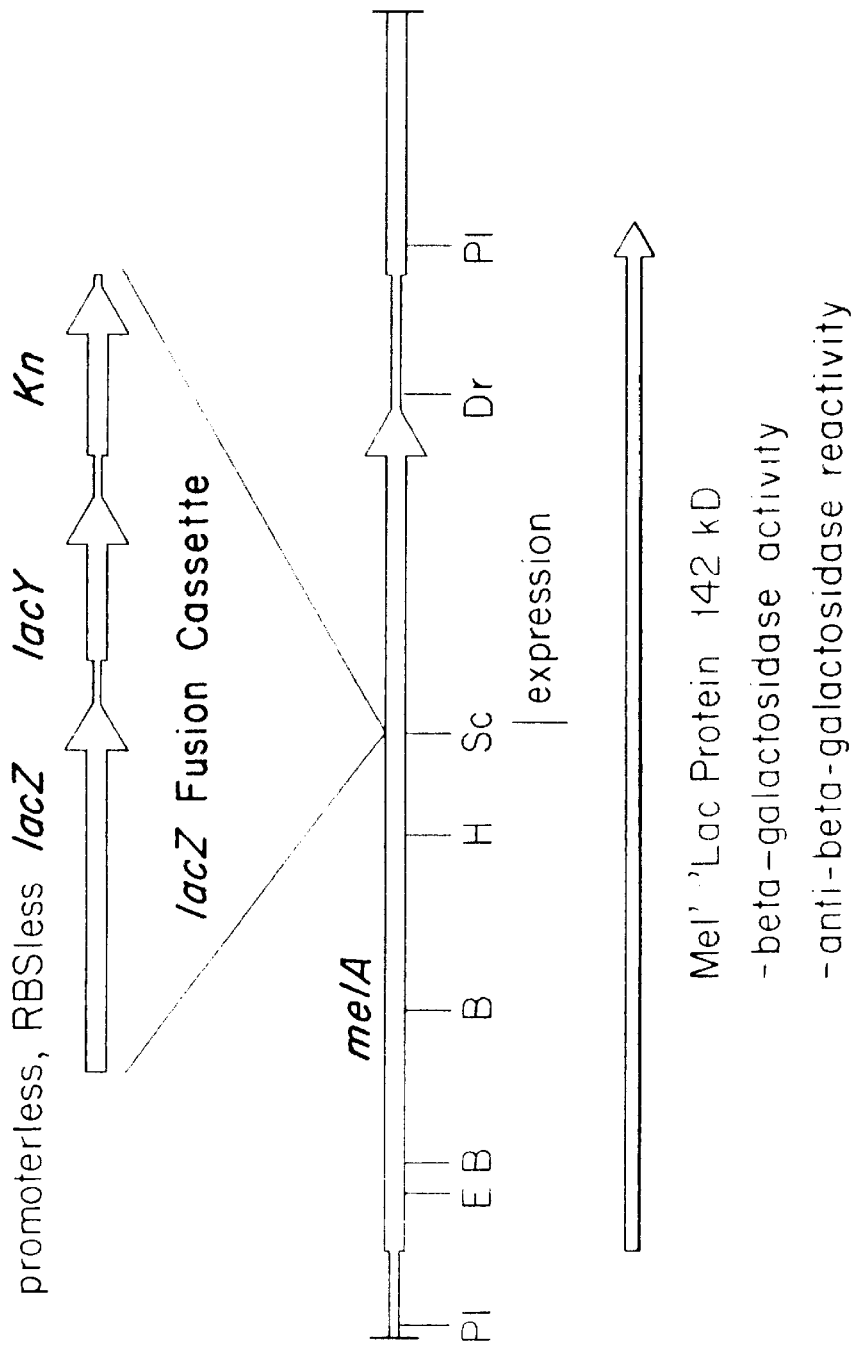
FIG. 2 depicts the pertinent region of the melA'::lacZ protein fusion construct, pMAC3. Abbreviations are the same as FIG. 1.

A melA-lacZ gene fusion was constructed as depicted in FIG. 2 by joining a lacZ fusion cassette to the 3' end of the melA gene to create a 142 kD fusion protein designated MeI'::'Lac.

The plasmids pLKC480–482, contain a lacZY cassette encoded on a single 6.3 kb SmaI restriction fragment. Each cassette is composed of a promoterless, RBS-less lacZ gene truncated for the first 22 bases, an intact lacY gene, and a kanamycin resistance ($KM^R$) marker (163). The plasmids, pLKC480, pLKC481, and pLKC482, when digested with SmaI, release a 6.3 kb fragment, but for each individual construct, the SmaI site is shifted by a single base. Thus, the three SmaI cassettes represent all three possible reading frames, and when inserted in the appropriate orientation into the coding region of a gene, one of the cassettes will result in a functional gene fusion.

Figure 4A:
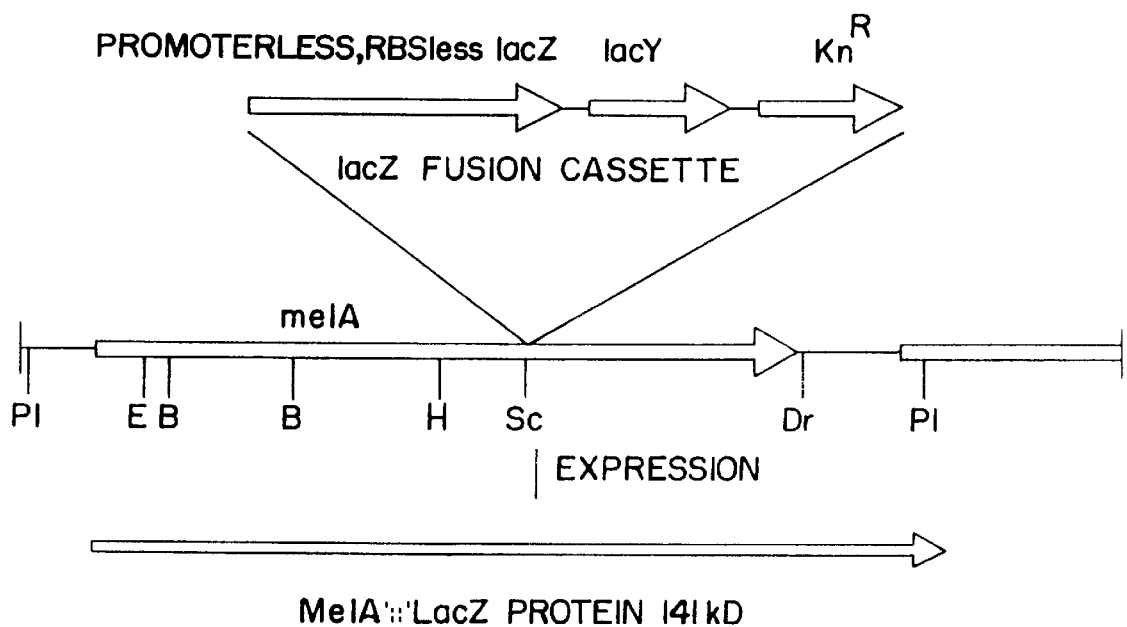
FIG. 4 shows the MelA'-'lacZ fusion construct. (A) The 6.3 kb SmaI fragment of pLKC482 (not to scale) was blunt-end ligated with ScaI-cleaved pMC3A (partial digestion, pUC19 has a single ScaI site), and this ligation mix was transformed into E. coli JM101. Transformations were plated on LB agar with Kn, Ap, and X-gal, and Lac+ transformants were isolated for further characterization. The predicted translation product of this fusion construct was 141 kD. (B) The fusion construct pMAC3 was sequenced using a primer specific for the 5' end of the truncated lacZ gene, and the sequence of the fusion junction is shown with the reading frame indicated below the sequence. [SEQ. ID NOS. 4 & 5]

The pLKC system was utilized to create melA'::'lacZ gene fusions for several purposes: (i) to verify that the reading frame indicated by sequence analysis of melA was correct; (ii) to generate Lac fusions of MelA for use as a reporter gene; and (iii) to produce a Mel Lac protein fusion to affinity purify. Two separate melA'::'lacZ fusions were generated with the pLKC cassettes. The Mel⁺ pMC3A plasmid was cleaved with BglII, blunt-ended with Klenow fragment, the 258 bp BglII fragment removed, and the large BglII fragment ligated with a SmaI-cleaved, gel-purified fusion cassette. This ligation was used to transform E. coli JM101, and the transformants were selected on LB agar containing Km, Ap, and X-gal. Although all three fusion cassettes were ligated to the BglII-cleaved pMC3A in separate reactions, only the pLKC482 cassette resulted in active β-galactosidase fusions as determined by X-gal cleavage. In addition, only cassettes inserted in the left-to-right orientation (relative to the melA sequence, FIG. 4A) resulted in lacZ+ phenotypes. The plasmid encoding this gene fusion was designated pMAC2. The same experiment was conducted with ScaI-cleaved pMC3A. All three fusion cassettes were again ligated with this fragment in separate reactions, and these were plated on the Ap, Km, X-gal-containing LB media (FIG. 4A). Only the ligation with the pLKC482-derived cassette, in the left-to right orientation resulted in Lac+ transformants. The plasmid encoding the B-galactosidase activity was designated pMAC3.

As a control experiment, the 4.2 kb RI fragment of pMC3A, deleted for 356 bp containing the melA promoter, RBS, and translational start, was ligated with all three pLKC fusion cassettes. None of these constructs, in either orientation, resulted in Lac+ transformants. In addition, pMC3A cleaved and blunt-ended at the DraIII site, just downstream of the predicted translational stop codon, was also ligated to all three SmaI cassettes. Again, none of the constructs in either orientation were Lac+, but all constructs were Mel⁺.

Figure 5:
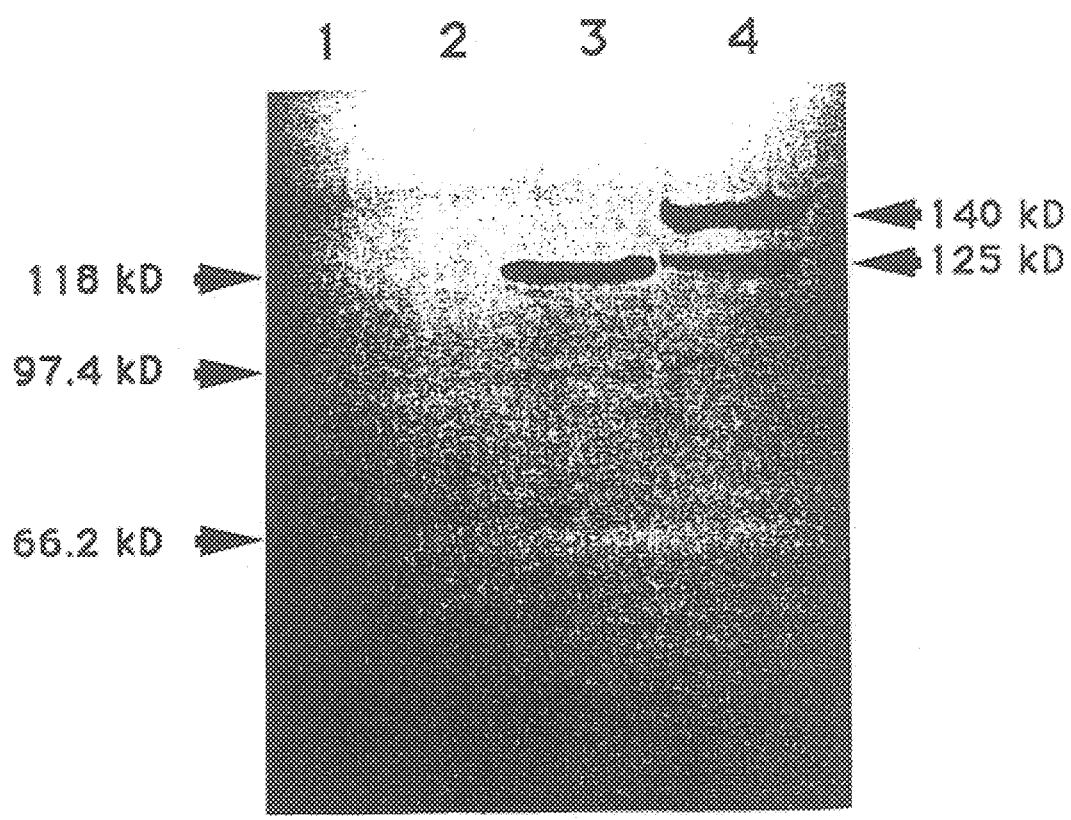
FIG. 5 shows immunostaining of fusion products with monoclonal anti-β-galactosidase. Crude extracts of several E. coil AB705 derivatives were electrophoresed on SDS-PAGE (7%), electrotransferred to nitrocellulose, and immunostained with anti-β-galactosidase. The extracts included E. coli AB705 (lane 1), and E. coli AB705 with PMC3A (lane-2), PMAC2 (lane 3), and PMAC3 (lane 4). Left arrows indicate the mobility of high molecular weight standards and right arrows point out the fusion products.
Figure 6:
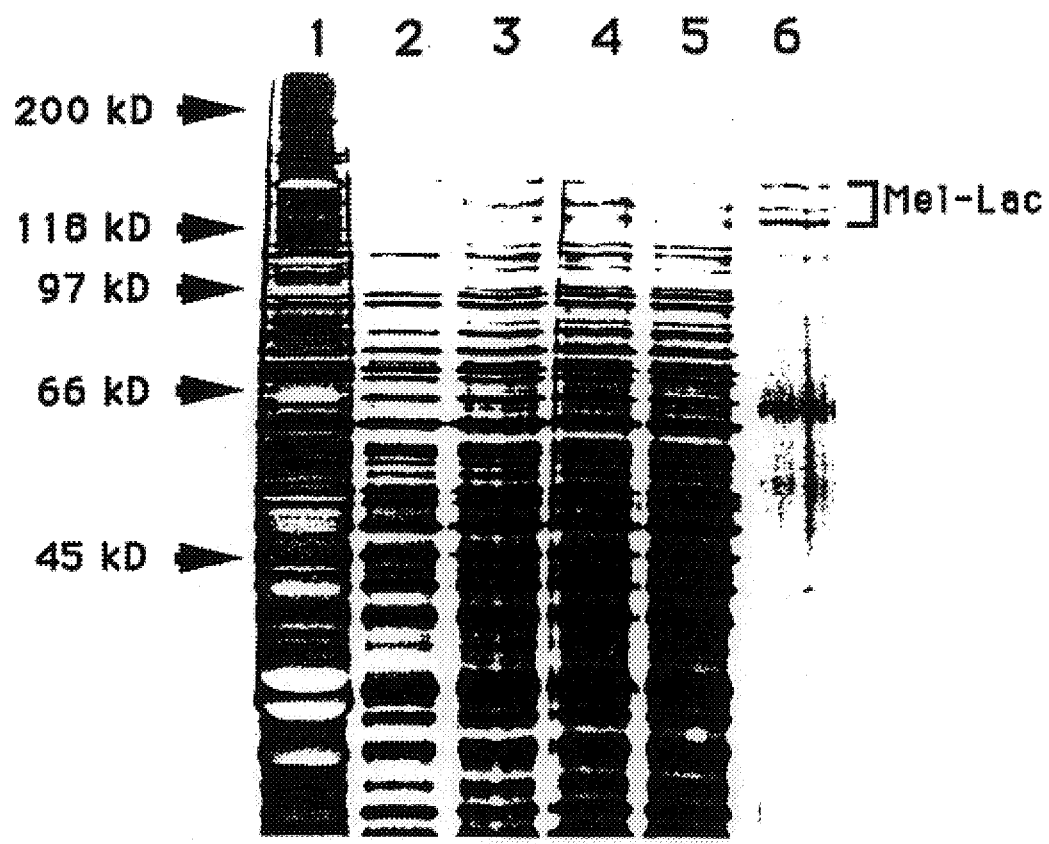
FIG. 6 shows the purification of pMAC3 fusion proteins. The fusion products of pMAC3 were purified using an anti-β-galactosidase affinity column. Aliquots of each step of the purification were collected and analyzed by SDS-PAGE and silver staining, including S. colwelliana D crude lysate (lane 1), $(NH_4)_2$ precipitate of this lysate (lane 2), three fractions of the unbound eluent collected during the loading of column (lanes 3–5), and the alkali-eluted, anti-β-galactosidase bound material (lane 6). Left arrows illustrate the mobility of high molecular weight standards, and the right bracket marks the fusion proteins. The photographic exposure was 2X longer for lane 6 than other lanes.

The pMAC2 and pMAC3 constructs were transformed into E. coli AB705, a lac deletion strain, that does not produce any detectable β-galactosidase (the M15 deletion of E. coli JM101 synthesizes an inactive β-galactosidase). To verify that the observed X-gal cleavage was due to the activity of the MelA-LacZ fusion protein, extracts of E. coli AB705 with pUC19, pMC3A, pMAC2, or pMAC3 plasmids were electrophoresed on SDS-PAGE, electrotransferred to nitrocellulose, and immunostained using monoclonal antibody against E. coli β-galactosidase (Promega Biotech, Madison, Wis.). The predicted molecular masses of the fusion proteins encoded by pMAC2 and pMAC3, were 127.7 kD and 141 kD, respectively. The immunoblot revealed that E. coli AB705 with or without pMC3A, did not produce any proteins that bound the anti-β-galactosidase antibody (FIG. 5, lanes 1 and 2). In contrast, the pMAC2 extract synthesized a strongly staining protein of approximately 125 kD (FIG. 6, lane 3). The pMAC3 extract synthesized a pair of strongly reactive proteins, a 140 kD and a 125 kD protein (FIG. 5, lane 4). Large β-galactosidase fusion proteins are typically unstable in the area of the fusion junction (157), and this protein probably corresponded to such a breakdown product. Both pMAC2 and pMAC3 also produced several smaller immunoreactive proteins, that probably corresponded to proteolytic cleavage products.

Figure 4B:
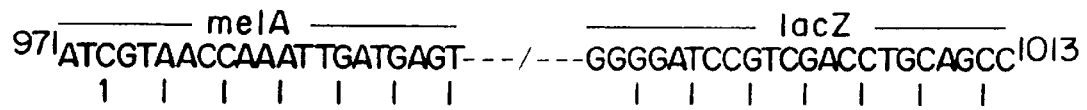

The fusion protein encoded by pMAC3 was selected for use in generating anti-MelA antibodies. The pMAC3 fusion protein is composed of the amino terminal 25.5 kD) of melA fused to 115 kD of lacZ. Sequencing of pMAC3 with a primer complementary to the 5' coding region of lacZ verified that the Mela-LacZ fusion protein was expressed in the predicted reading frame (FIG. 4B).

Affinity purification of the pMAC3-encoded Mela-LacZ fusion protein. Aliquots of affinity column fractions were electrophoresed on an SDS-PAGE gel and silver stained. The bound material was shown to constitute a small fraction of the cellular protein (FIG. 6, lane 6), when compared to crude sonicate (FIG. 6, lane 1), ammonium sulfate precipitate (FIG. 7, lane 2), and the three unbound fractions (FIG. 7, lanes 3–5). Specifically, these were a set of large 120–145 kD proteins (FIG. 7, lane 6, brackets). This included bands corresponding to the two reactive proteins detected in the immunoblots with anti-β-galactosidase (125 kD and 140 kD), as well as a number of smaller proteins, probably products of proteolytic cleavage during purification. The other fractions also contained these large bands, indicating that during chromatography the affinity column did not bind all of the β-galactosidase fusion proteins (FIG. 6, lanes 2–5). Even so, the column did significantly purify the large fusion protein products from the total protein suspensions, as evidenced by the relative purity of the preparation (FIG. 6, lane 6). The eluted material contained 150 mg/ml protein. The affinity-purified preparation was used to immunize three Balb/C mice and generate polyclonal antisera to the fusion protein products as described in Materials and Methods.

Figures 7A, 7B:
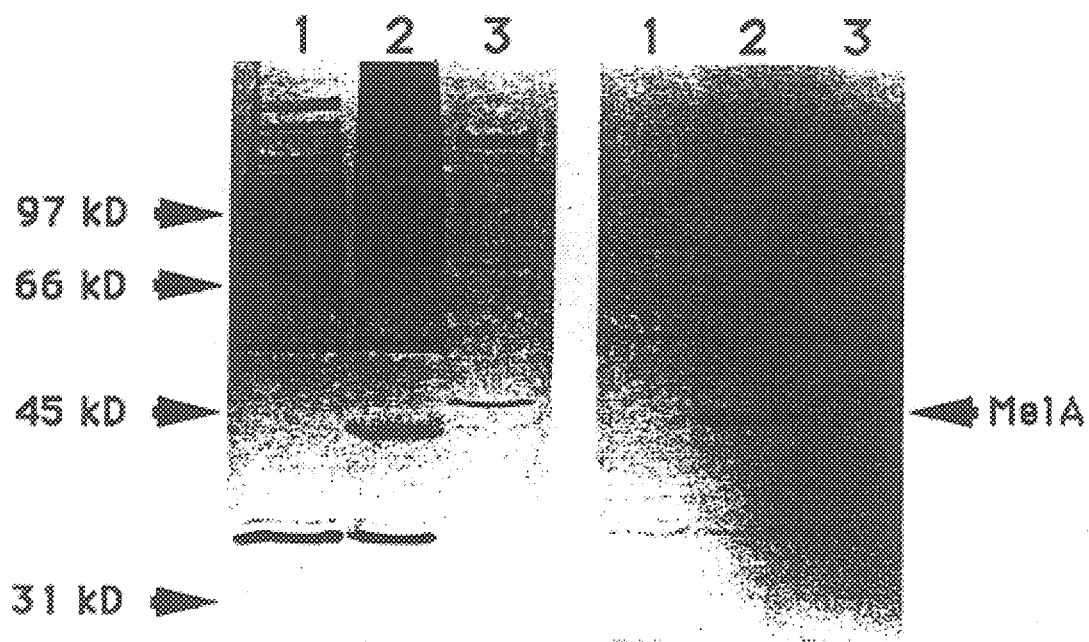
FIG. 7 is the analysis of E. coil and S. colwelliana D extracts with anti-MelA-LacZ serum. (A) crude extracts of E. coil JM101 pUC19 (lane 1), E. coil JM101 pMC3A (lane 2), and S. colwelliana D (lane 3) were electrophoresed on SDS-PAGE, electrotransferred to nitrocellulose, and immunostained with the anti-MelA-LacZ serum. (B) The same extracts as in A, were immunostained with anti-MelA-LacZ sera that was pre-adsorbed with E. coli β-galactosidase and E. coil JM101 pUC19 whole cell extracts. Left arrows show mobilization of size standards and the right arrow points out the mobility of MelA for both blots.

Analysis of anti-MelA-LacZ serum. The polyclonal antisera was used to immunostain electrotransfers of extracts from E. coli JM101 carrying pUC19 or pMC3A, and S. colwelliana D. The E. coli extracts contained a number of immunoreactive proteins, with varying degrees of staining (FIG. 7A, lanes 1 and 2). The single difference between extracts of E. coli carrying pUC19 and E. coli carrying pMC3A was a broad, lightly staining 41 kD protein. This corresponded to a lightly staining protein of the same estimated size from the S. colwelliana extracts (FIG. 7A, lane 3). This extract also contained a number of more strongly staining proteins in addition to the 41 kD protein. The antisera was extensively adsorbed with E. coli β-galactosidase and a lysate of E. coli carrying pUC19, and used to immunostain electrotransfers of the same three extracts. It was observed that the majority of E. coli proteins that had reacted strongly to the crude antisera, were either not visible, or significantly reduced in intensity, while the pMC3A-specific 41 kD protein stained more intensely (FIG. 7B, lanes 1 and 2). This pattern was also repeated with the S. colwelliana D extract, where the 41 kD protein remained at equal or increased intensity (FIG. 7B, lane 3). A second, larger band was not removed by the adsorption, but the nature of this protein is unknown. The antiserum was tested with dilutions of a whole cell extract from E. coli JM101 carrying pMC3B and was sensitive to changes in concentration over a one hundred-fold range (1 µg–100 µg) of total protein concentration (data not shown).

Figure 8:
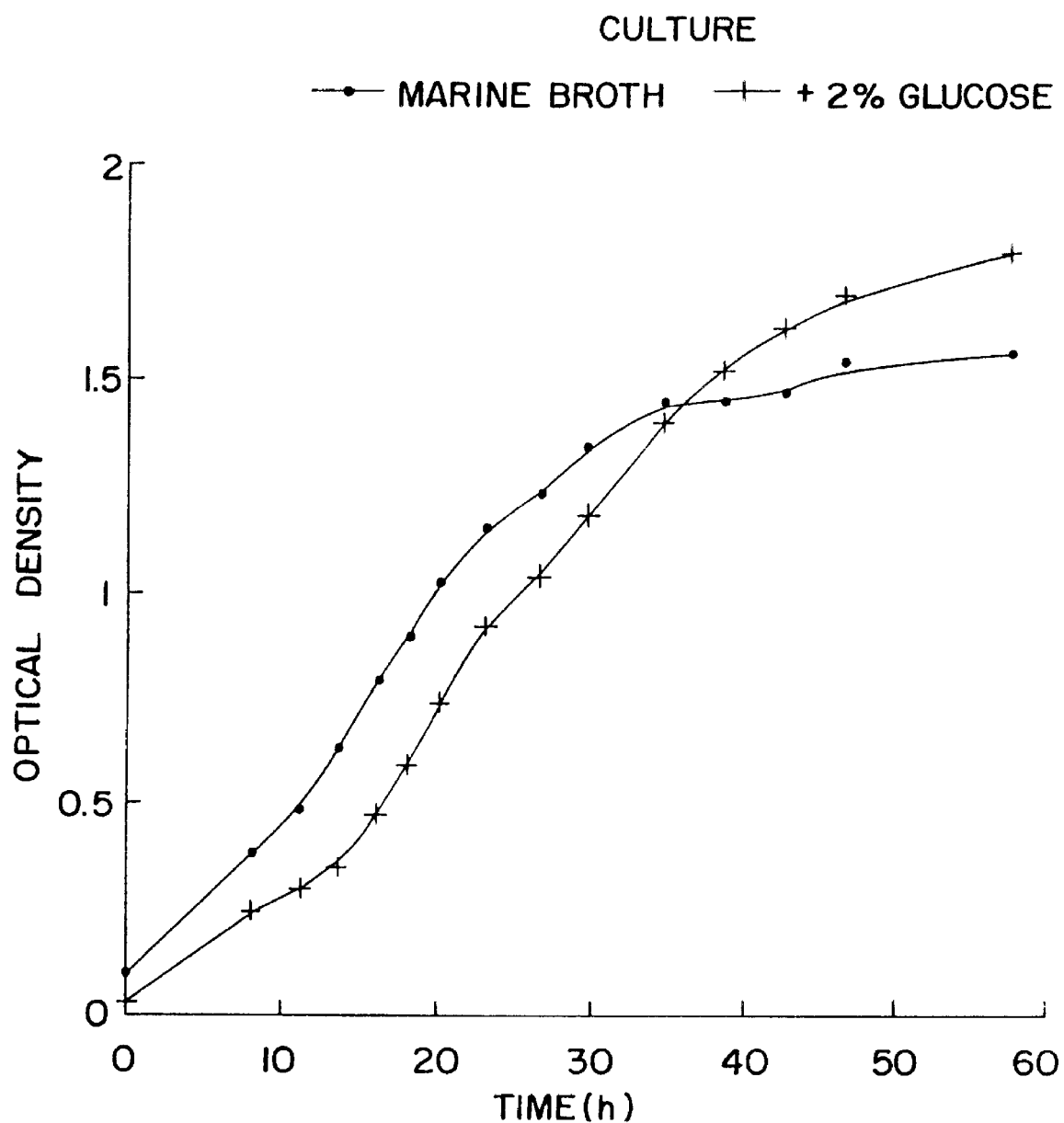
FIG. 8 shows growth curves of S. colwelliana D. Aliquots of S. colwelliana D grown with shaking at 200 RPM in 1 L of Marine Broth 2216, and 1 L of MB supplemented with 2% glucose, were removed at specific time points and analyzed for optical density at a wavelength of 650.

To determine if the appearance of melanin correlated with the presence of MelA, the anti-Mela-LacZ serum was used to monitor the levels of the protein during growth in batch culture. A pair of cultures, one in MB and the other in the same media supplemented with 2% glucose, were inoculated with 10 ml of a confluent S. colwelliana D culture. Aliquots were removed from the cultures over the course of growth, optical densities (O.D.) were measured, and cell pellets were frozen. O.D. readings showed that the unsupplemented culture was in logarithmic growth by 8 h post-inoculation and in stationary phase by 30–35 h (O.D. 1.5) (FIG. 8). In contrast, the culture supplemented with 2% glucose did not begin logarithmic growth until 15 h post-inoculation and was in stationary phase by 50 h (O.D. 1.7–1.8) (FIG. 8). The time of pigment formation was also significantly different for each of the two cultures, 30 and 40 h postinoculation for Marine Broth 2216 and Marine Broth plus glucose, respectively.

Figure 9A:
FIG. 9 is a time course for the immunodetection of MelA during batch growth. (A) Aliquots of the same MB culture (FIG. 9) were standardized for protein, separated on SDS-PAGE, electrotransferred to nitrocellulose and immunostained with the anti-MelA-LacZ sera. E. coli carrying pMC3B (lane 1) and 100 μg aliquots taken at 11 h (lane 2), 16 h (lane 3), 20 h (lane 4), 26 h (lane 5), 34.5 h (lane 6), 42 h (lane 7), and 57 h (lane 8), were analyzed. (B) Analysis was of a culture grown in MB plus 2% glucose. Identical concentrations and time points as A were used, except for lanes 1 and 2 (66 and 69 μg, respectively), due to low cell densities. Left arrows indicate mobility of size standards and the right arrow marks MelA.
Figure 9B:
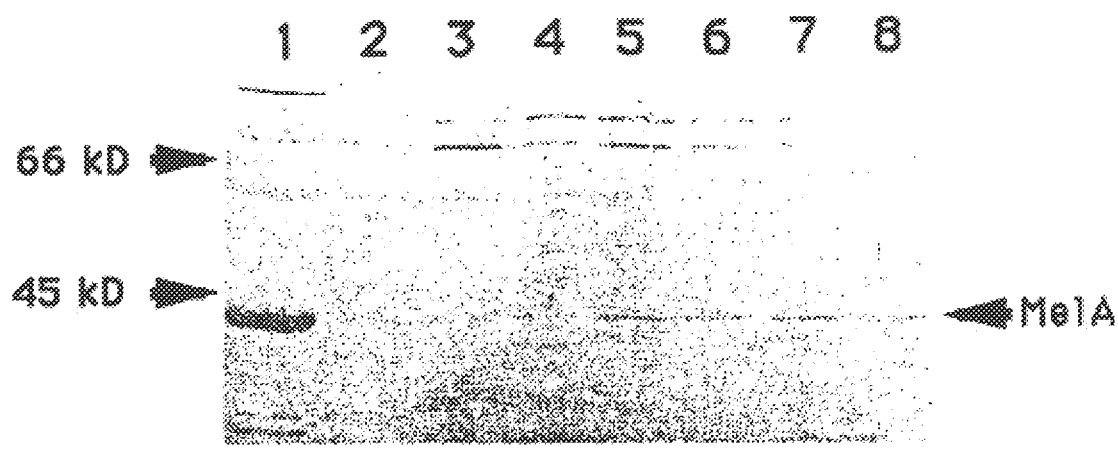

The frozen cell pellets were standardized for protein concentration, separated electrophoretically on SDS-PAGE, electrotransferred to nitrocellulose, and immunostained with the anti-MelA-LacZ serum. This revealed that the 41 kD protein was present throughout the growth cycle in the unsupplemented Marine Broth and the 2% glucose-supplemented cultures (FIG. 9A and 9B, lanes 1–8). Furthermore, there was no significant difference between the steady state level of melA in the two cultures.

Figure 10:
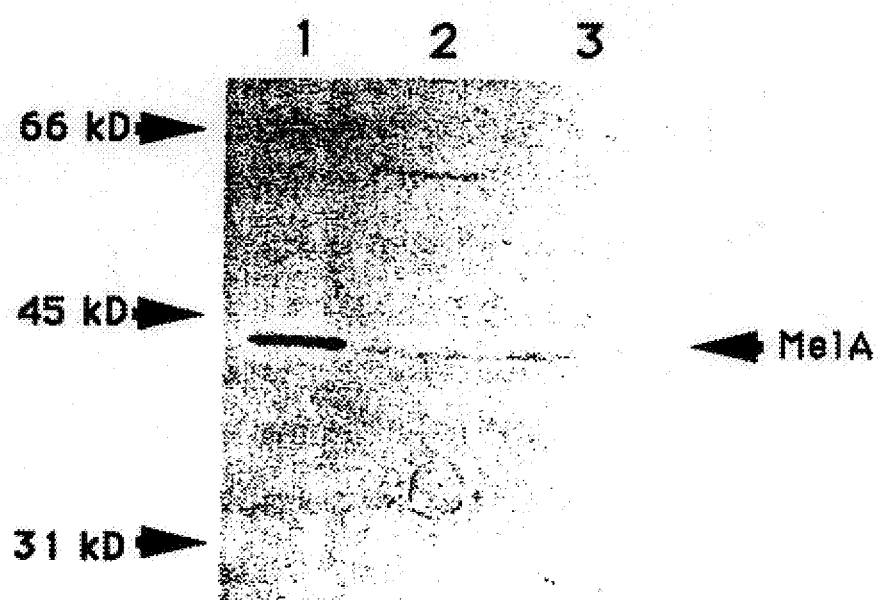
FIG. 10 shows MelA synthesis in media supplemented with tyrosine and copper. Whole cell extracts of two parallel cultures of S. colwelliana D, one grown in Marine Broth 2216 and the other in Marine Broth 2216 plus 5 mM tyrosine and 5 μg/ml $CuSO_4$, shaken at 200 RPM, were prepared. 10 μg of E. coli JM101 carrying pMC3B (lane 1) and 100 mg of the unsupplemented culture extract (lane 2) and the tyrosine-copper supplemented culture extract (lane 3) were separated by SDS-PAGE, electrotransferred to nitrocellulose and immunostained with the anti-MelA-lacZ antibodies. Left arrows indicate mobilization of size standards and the right arrow marks MelA.

Enhancement of pigmentation with tyrosine and copper. To determine whether the enhanced pigmentation observed in the presence of tyrosine and $CuSO_4$ was due to an induction of melA synthesis, parallel cultures of *S. colwelliana* D were grown, one unsupplemented and one with added tyrosine (5 mM) and $CuSO_4$ (5 µg/ml). Cells were harvested from these cultures in late logarithmic stage, washed, resuspended and frozen. Equal amounts of protein were electrophoresed on SDS-PAGE, electrotransferred, and immunostained with anti-MelA-LacZ serum. Comparison of the two extracts suggested at most a two-fold induction of MelA synthesis in the tyrosine-$CuSO_4$ supplemented culture (FIG. 10, lanes 2 and 3).

Figure 12:
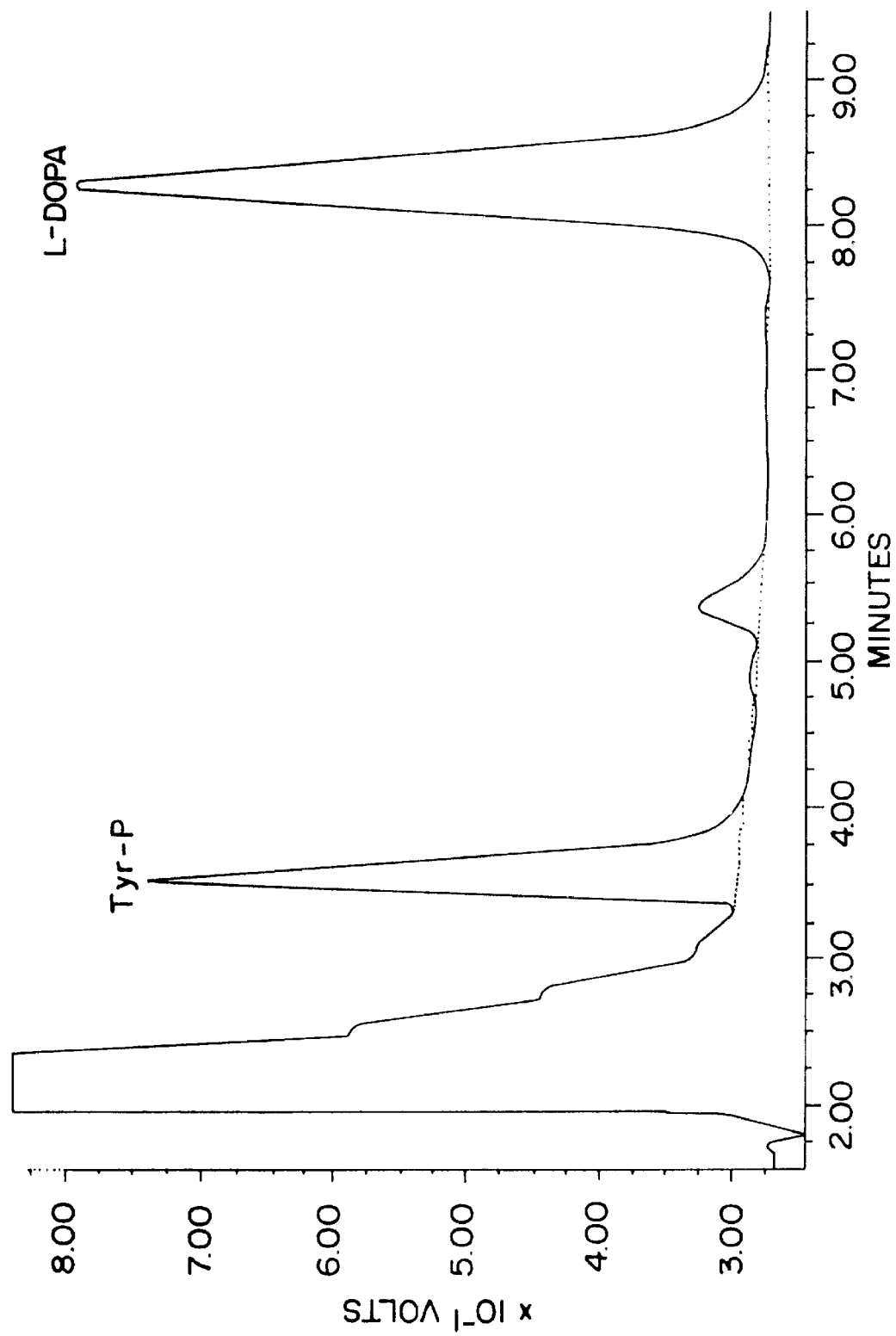
FIG. 12 is an HPLC elution profile of S. colwelliana D assay products. Assays were conducted with whole cell extracts as described in Materials and Methods.

*S. colwelliana* D melanin production occurs late in logarithmic growth, but the synthesis of MelA appears to be constitutive (FIG. 9A and 9B). Catecholamines or hydroxyquinones will spontaneously polymerize to melanin under oxidative and/or basic conditions (Bell et al, Ann. Rev. Phytopathol. 24:411–451 (1986)). Supernatants of *S. colwelliana* D from early or mid-logarithmic, pre-pigmentation cultures were observed to pigment when oxygenated. This suggested that the melanin precursors were being synthesized significantly earlier than the onset of melanin polymerization. To determine how early melanin precursors were accumulating, 10 ml aliquots of an actively growing *S. colwelliana* D culture were removed at various times, treated with 0.5 g of solid NaOH, shaken vigorously, and monitored for pigment formation. This revealed that melanin precursors were present even in the early stage of growth in MB (FIG. 12A). MB treated in the same manner was used as a negative control and consistently remained unpigmented.

Figure 11A:
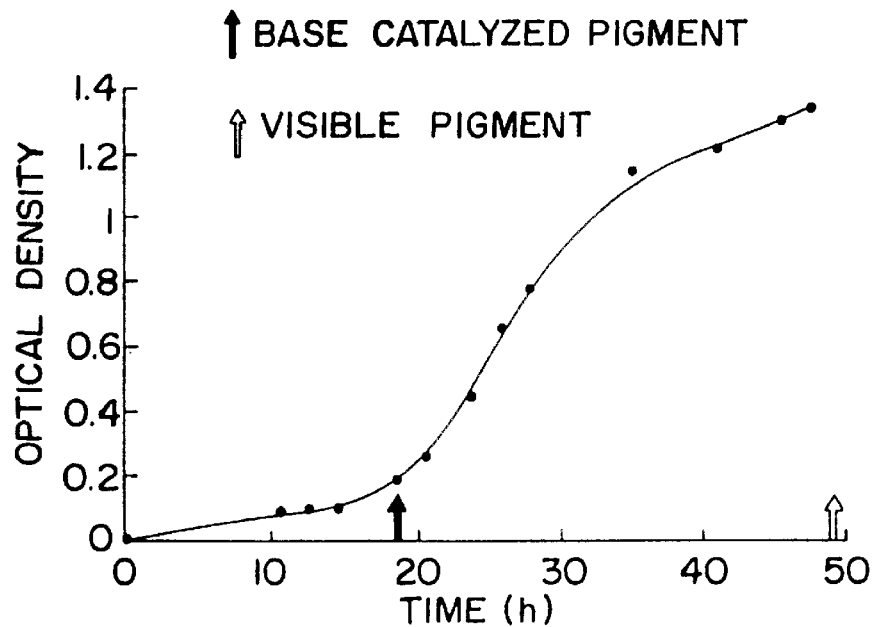
FIG. 11 shows melanin precursors and dissolved oxygen in S. colwelliana D culture. (A) 10 ml aliquots of a MB shaken at 200 RPM were removed at specific times during growth. Melanin in culture was also recorded at each time point. The optical density of each extract was measured, the sample was treated with 0.5 g of solid NaOH, and scored for melanin formation. (B) Aliquots of cultures in MB shaken at 300 RPM were removed at specific time points and analyzed for optical density (+) and dissolved oxygen levels (•).
Figure 11B:
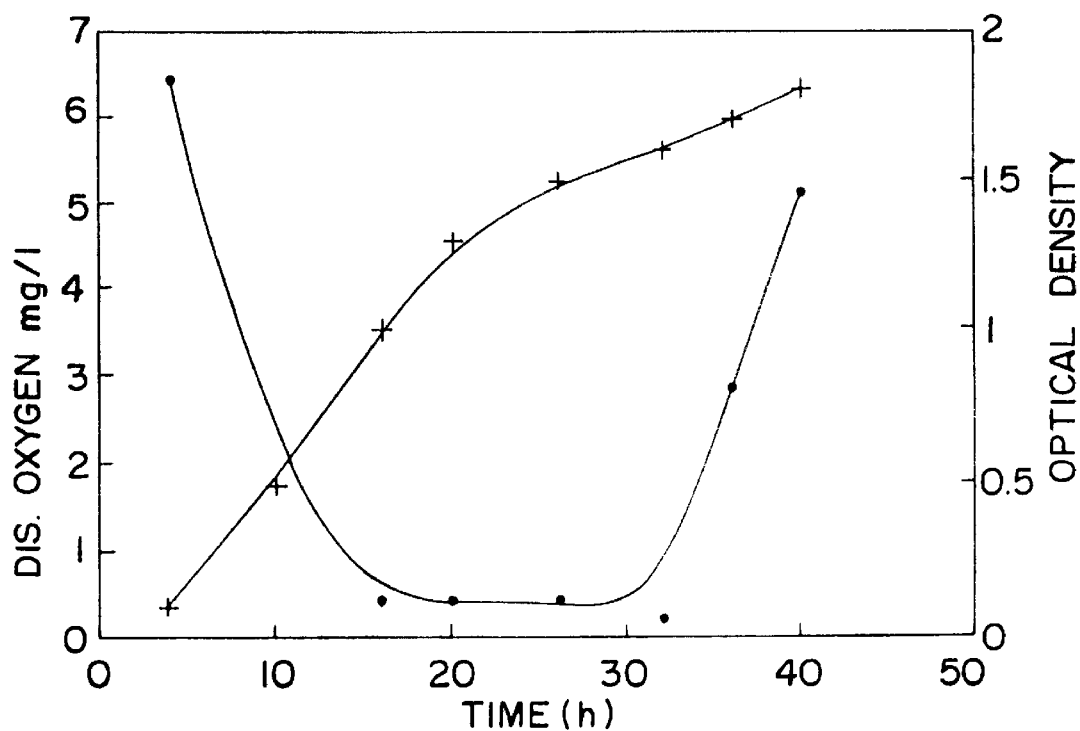

Previous work had shown that actively growing cultures of *S. colwelliana* D were depleted of dissolved oxygen. Surprisingly, this was observed even for *S. colwelliana* D cultures grown at the highest obtainable aeration in culture flasks (i.e. with a wrist action shaker at its maximum setting). A time course experiment where dissolved oxygen was measured in cultures of *S. colwelliana* D over the growth cycle showed that oxygen levels were close to saturation at the time of inoculation, as low as detectable during logarithmic growth, and returned to high levels during stationary phase (FIG. 11B). By 15 h post-inoculation, the levels of dissolved oxygen were lower than the oxygen electrode sensitivity (0–5 mg/L), and remained so until 32 h had elapsed. Increases of dissolved oxygen coincided with the slowing of culture growth, and also the first signs of visible pigmentation.

This protein exhibited β-galactosidase activity and reacted with anti-β-galactosidase antibodies. To overexpress Mel'::'Lac, the vector containing the gene fusion was introduced into *E. coli*, a transformant selected and cultured under normal conditions to express the fusion protein. After confluent growth, the cells were harvested, lysed, and the fusion protein was affinity purified using anti-β-galactosidase antibodies.

To prepare polyclonal antibodies against MelA, the affinity purified fusion protein was injected into mice using standard procedures [Harlow et al. (1988), Antibodies: A Laboratory Manual, Cold Spring Harbor Laboratory, Cold Spring Harbor, N.Y., pp. 726.] The antiserum was tested by immunoblotting whole cell extracts of *E. coli* strains producing the melA gene product and whole cell extracts of *S. colwelliana*. An *E. coli* strain lacking the melA gene served as a control. The immunoblots revealed that the antiserum reacted specifically with an $M_r$ 42,000 protein present in *S. colwelliana* and in *E. coli* expressing the melA gene, but not in *E. coli* lacking the melA gene.

Monoclonal antibodies are prepared by removing the spleens from mice injected for polyclonal antibodies (after determining that the mice are producing anti-MelA antibodies). The splenocytes are then isolated and used in cell fusions with murine myeloma cells to generate antibody-producing hybridomas (Harlow et al.). The hybridoma supernatants are subsequently screened by immunoblotting as above to identify hybridomas which produce antibodies against MelA.

EXAMPLE 5

Overexpression of the melA Gene

Figure 3:
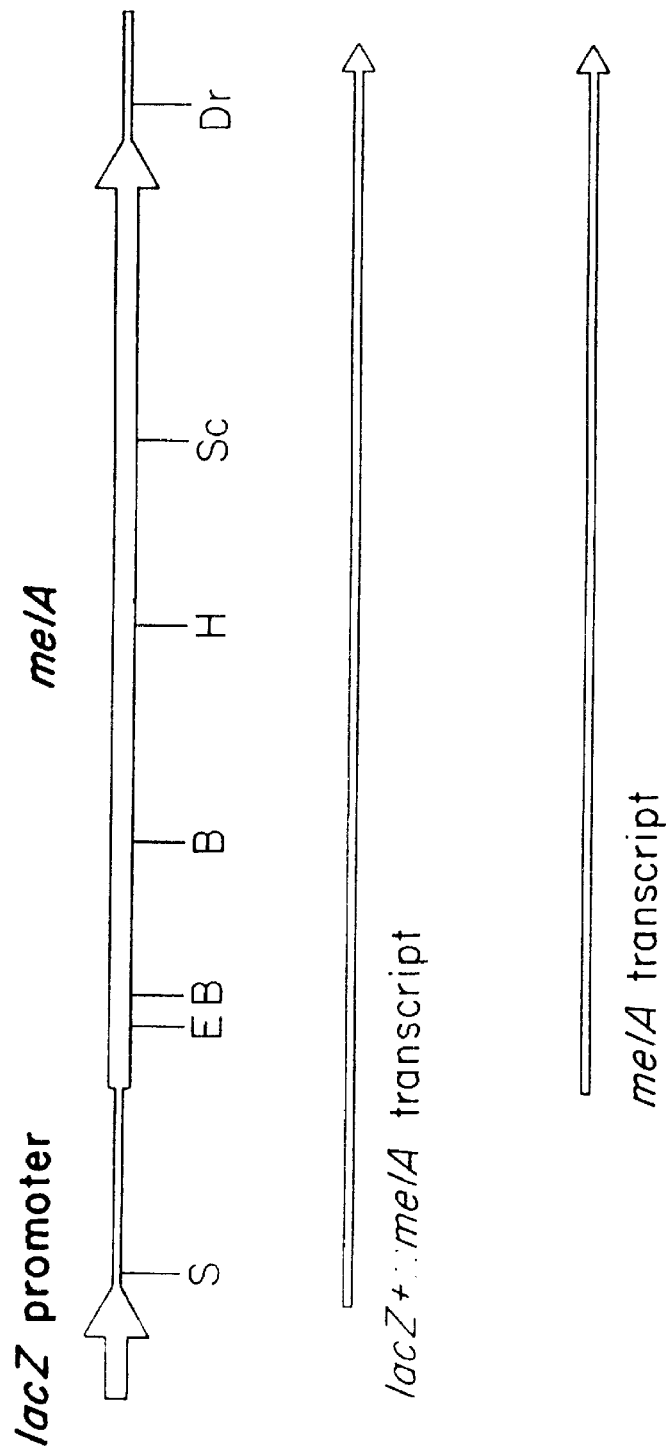
FIG. 3 depicts the pertinent region of the overexpression plasmid pMC3B designed to overproduce S. colwelliana MelA. Abbreviations are the same as FIG. 1.

A replicable expression vector to overproduce the *S. colwelliana* MelA under control of the lacZ promoter was constructed. Briefly, a DNA restriction fragment from pUC19 containing the lacZ promoter was ligated to the 1.9-kb HincII fragment containing the melA coding sequence to generate plasmid pMC3B as depicted in FIG. 3. pMC3A and pMC3B have the HincII fragment in opposite orientations, such that in pMC3B transcriptional readthrough occurs from the lac promoter into the melA gene. *E. coli* containing pMC3B produces MelA at elevated levels relative to pDC1 as evidenced by darker pigmentation of the colonies and 10-fold or higher RNA levels.

EXAMPLE 6

RNA Isolation, Blotting and Hybridization

RNA was extracted by the technique of Summers (W. C. Summers (1970) *Anal. Biochem.* 33:459–463) from 50 ml cultures of *S. colwelliana* D or *E. coli* JM101 carrying the plasmids of interest. All buffers and solutions used for this protocol were made RNAse-free by treatment with diethylpyrocarbonate (DEPC). Cells were collected by centrifugation (12,000×g, 10 min, 4° C.) and the pellet was resuspended in 10 ml of Protoplasting buffer. Lysozyme chloride was added (80 µl of a 50 mg/ml stock), and incubated for 15 min on ice. Protoplasts were collected by centrifugation (5900×g, 5 min, 4° C.). The pellet was resuspended in 1 ml of lysis buffer, 30 µl of DEPC was added, and the mixture was incubated at 37° C. for 5 min followed by addition of 500 µl of a saturated NaCl solution on ice, and incubation for 10 min. The precipitated protein was removed by centrifugation (6,400×g, 10 min in a microfuge), and the nucleic acid in the supernatant ethanol precipitated. The nucleic acid was collected by centrifugation (6,400×g, 15 min in a microfuge), followed by a 70% ethanol rinse, recentrifugation, and air drying of the pellet. The pellet was resuspended on ice [400 µl of 1X DNAse I buffer, 80 U RNAsin (Promega Biotech, Madison, Wis.)], and DNA was removed by digestion with 75 U of RNAse-free DNAse I (Boehringer-Mannheim Biochemicals, Indianapolis, Ind.) for 2 h at 25° C. Following digestion, the RNA was extracted with phenol/chloroform, and ethanol precipitated. The RNA pellet was resuspended on ice (100 µl 1X DNAse I buffer, 20

U of RNAsin) and digested with 15 U of DNAse I for 30 min at 25° C. The RNA was phenol/chloroform extracted, ethanol precipitated, and collected by centrifugation (6,400×g, 15 min). The pellet was resuspended in 30 μl of H$_2$O and stored at –70° C.

RNA was separated electrophoretically on 1.3% formaldehyde-agarose gels as described elsewhere (J. Sambrook, E. Fritsch, and T. Maniatis (eds). (1989) Molecular Cloning: A Laboratory Manual. Second Edition. Cold Spring Harbor Laboratory Press, New York). Typically, 30–50 μg RNA was incubated in sample treatment buffer (15 min, 65° C.). Gel-loading buffer was added to the treated sample prior to loading onto a 1.3% formaldehyde-agarose gel (1.3% agarose, 6.6% formaldehyde, 1X MOPS running buffer). This was electrophoresed (4 volts/cm$^2$) in 1X MOPS running buffer approximately ¾ the length of the gel as judged by migration of bromophenol blue tracking dye. Size estimation of the separated RNA was achieved by electrophoresing ethidium bromide-stained RNA size standards (Bethesda Research Laboratories, Gaithersburg, Md.) alongside the RNA samples.

Separated RNA was transferred to Zeta-Probe nylon membranes by an alkaline, capillary blotting procedure (D. A. Mann and K. C. Reed (1987) *Biorad Molecular Biology Reports* 1:1–4) using 50 mM NaOH as the transfer solution. The gel was rinsed four times in DEPC-treated H$_2$O to remove excess formaldehyde before transferring overnight as described by Sambrook et al (J. Sambrook, E. Fritsch, and T. Maniatis (eds) (1989) *Cold Spring Harbor Laboratory Press,* New York). Following transfer, the membrane was marked for orientation, rinsed in 2X SSPE, and allowed to air dry.

For hybridization, the dried membrane was rehydrated by soaking in 6X SSPE. The membrane was placed in a heat-sealable plastic bag with RNA prehybridization solution (0.2 ml/cm$^2$ of membrane), and incubated at least 1 hr at 65° C. Following this, the RNA prehybridization solution was poured off and replaced with DNA/RNA hybridization solution (0.05 ml/cm$^2$ of membrane). The radiolabeled oligonucleotide was added, the bag resealed, and the hybridization was allowed to proceed with shaking for at least 16 hr at 65° C. After this incubation, the hybridization solution was poured off, the membrane removed, and washed twice for 5 min at 25° C. (5X SSPE, 0.01% SDS) and twice for 5 min in the same wash solution at 37° C. If high background remained (as judged by Geiger counting), additional washes were performed for 5 min at 37° C. (4X SSPE, 0.01% SDS). The membrane was enclosed in a single layer of plastic wrap and autoradiographed on X-ray film.

Northern blotting. Total RNA from several *E. coli* JM101 strains carrying pUC19 or melA plasmids, and RNA from *S. colwelliana* D was separated electrophoretically on formaldehyde-agarose gels. The RNA in these gels was transferred to nylon membranes and probed with a melA-specific radiolabeled oligonucleotide probe, complementary to the 5' (nts 304–333) coding sequence of the melA gene. RNA derived from *E. coli* carrying pUC19 did not bind the probe. Surprisingly, RNA from a melanin-synthesizing *E. coli* carrying pMC3A (Table 2), also did not bind detectable levels of probe. In addition, *S. colwelliana* D RNA also failed to show detectable hybridization to the probe (data not shown). In contrast, RNA from *E. coli* JM101 carrying pMC3B, hybridized strongly with the probe, as two distinct transcripts of 1.6 and 1.3 kb. This construct contains the identical DNA insert as pMC3A, but in the opposite orientation in pUC19 (Table 2). The upstream regions of pMC3A and pMC3b were resequenced and again shown to be identical. In pMC3B, the melA coding region begins 316 bp downstream of the pUC19 lacZ promoter. It is most likely that this orientation resulted in a fortuitous operon fusion between the pUC19 lacZ promoter and the melA gene, and that transcription of melA initiates from the lacZ promoter in addition to the melA promoter. The sizes of the two transcripts (1.6 and 12.3 kb) match well with the transcript sizes predicted from such a configuration. Interestingly, this suggests that expression from the lacZ promoter has also increased transcription initiation from the melA promoter.

TABLE 2

BACTERIAL STRAINS, PLASMID AND PHAGE

| Strain, plasmid or phage | Relevant characteristics |
|---|---|
| *S. colwelliana* | |
| strain D | diffusable pigment |
| strain V | viscous exopolysaccharide |
| *E. coli* | |
| HB101 | host strain, recA13 |
| JM101 | host strain, α-complementation strain |
| SE5000 | Maxicell strain, recA56 |
| Plasmids | |
| pHC79 | cosmid cloning vector, AP$^R$, TC$^R$ |
| pUC19 | cloning vector for α-complementation systems, AP$^R$, Lac+ |
| pCT1 | original Mel+ clone, 10.1 kb *S. colwelliana* insert, AP$^R$ |
| pDC1 | 4.2 kb PstI fragment of pCT1 in pUC19, AP$^R$, Mel+ |
| pDC2 | same as pDC1, opposite orientation in pUC19, AP$^R$, Mel+ |
| pDC3 | 4.0 kb PstI-NcoI fragment of pDC1 in pUC19, AP$^R$, Mel+ |
| pDC4 | 3.3 kb PstI-HincII fragment of pDC1 in pUCl9, AP$^R$, Mel+ |
| pMC1 | 3.7 kb BglII-NcoI fragment of pDC3 in pUC19, AP$^R$, Mel+ |
| pMC2 | 3.3 kb BglII-SphI fragment of pMC1 in pUC19, AP$^R$, Mel+ |
| pMC3A | 1.9 kb HincII-HincII fragment of pMC2 in pUC19, AP$^R$, Mel+ |
| pMC3B | same as pMC3A, opposite orientation in pUC19, AP$^R$, mel+ |
| pMC4B | 1.6 kb PleI-PleI fragment of pMC3A, opposite orientation in pUC19, AP$^R$, Mel+ |
| pMC5A | 1.3 kb HincII-DraIII fragment of pMC3A in pUC19, AP$^R$, Mel+ |
| pMC6A | 1.3 kb NspI-NspI fragment of pMC3A in pUC19, AP$^R$, Mel– |
| pNC1 | 3.2 kb EcoRI-PstI fragment of pDC1 in pUCl9, AP$^R$, Mel– |
| pNC2 | 300 bp. BglII-BglII deletion of pMC3A, AP$^R$, Mel– |
| pNC3 | 784 bp HincII-HincII fragment of pMC3A in pUC19, AP$^R$, Mel– |
| PNC4 | 1.1 kb HincII-HincII fragment of pMC3A in pUC19, AP$^R$, Mel– |
| pNC5 | 1.5 kb PstI-BglII fragment of pDC1 in pUC19, AP$^R$, Mel– |
| Phage | |
| M13mp19 | single-stranded DNA phage for DNA sequencing, AP$^R$, Lac+ |
| M13mpMCA | 729 bp BglII-DraIII fragment of pMC3A in M13mpl9 |

EXAMPLE 7

Isolation of mlgh Gene

The 5' end of a second ORF, directly downstream and in the same orientation as melA was identified, and designated mlgA (mel-linked gene). The entire sequence of mlgA was obtained and is depicted in FIG. 13. This ORF contained an internal HincII recognition site and corresponded to the 17 kD protein revealed during the in vitro expression analysis. The ORF had two potential translational initiation sites, an ATG codon at position 95, and an ATG codon at position 177, the translation products of which were predicted to be 19.3 kD (176 amino acids) and 16.6 kD (153 amino acids), respectively. The most likely start site was at position 177 since the size of this translation product was closest to that observed in the in vitro expression experiments. Furthermore, there is a consensus ribosome binding site (RBS) upstream of the ATG (7 nts) at position 177, while there is no RBS consensus sequence upstream of the ATG at position 95. The role of this protein in melanogenesis is unclear because deletion subcloning in E. coli demonstrated that only melA was required for the observed pigment synthesis.

EXAMPLE 8

Sequence Analysis and Homology Studies

Figure 14:
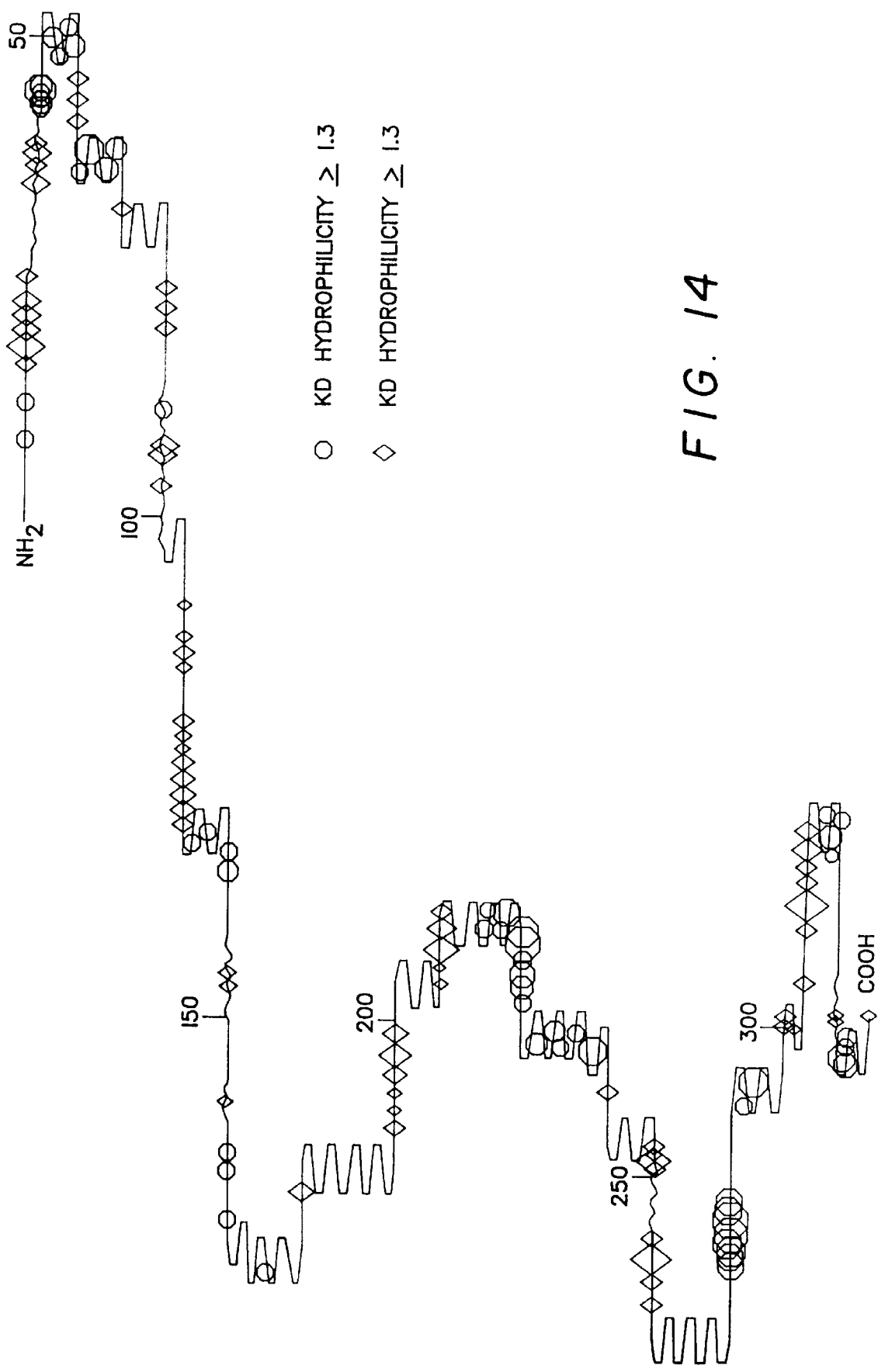
FIG. 14 is the predicted secondary structure of melA gene product. This secondary structure plot was generated using the Kyte-Doolittle hydropathy index (J. Mol. Biol. 157:105–132) and running the algorithm of Garnier-Osguthorpe-Robson (J. Mol. Biol. 120:97–120) to predict the structure. The Wisconsin Package from the Genetics Computer Group was used to run the algorithms and generate the figure. Large sine-wave represents α-helices; the more shallow sine-wave represents βpleated sheets; 90° turns represent β-bends, and straight lines represent random coil. The overstruck diamonds and octagons represent hydrophobic and hydrophilic regions of the polypeptide, respectively.

The predicted amino acid sequence for the melA gene product was deduced and analyzed for any recognizable structural motifs. Net charge and hydropathy plots of MelA revealed an acidic protein with no strong tendencies towards hydrophobicity or hydrophilicity. No potential membrane-spanning helices or hydrophobic signal sequences were identified, as determined by the methods of Eisenberg et al (D. Eisenberg, E. Schwartz, M. Komarony and R. Wall (1984) *J. Mol. Biol.* 179:125–142) and von Heijne (G. von Heijne (1986) *EMBO J.* 5:3021–3027), respectively. The sequence of this protein predicts a polypeptide possessing a relatively even distribution of α-helical and β-pleated sheet regions (J. Garnier, D. J. Osguthorpe, and B. Robson (1978) *J. Mol. Biol.* 120:97–120), with no significant bias towards either structural motif. A predictive secondary structure plot summarizing this information is shown in FIG. 14.

Sequence alignments between MelA and the tyrosinases from human, mouse, *Neurospora crassa,* and *Streptomyces spp.* (PIR, Swiss-Prot and NBRF protein sequence databases) revealed no stretches of significant homology. Furthermore, there were no recognizable copper-binding sites in the MelA sequence (K. Lerch, M. Huber, H. Schneider, R. Drexel, and B. Linzen (1986) *J. Inorg. Biochem.* 26:213–217). Global searches of these databases also failed to identify any protein sequences with significant similarity to MelA.

The predicted amino acid sequence for the mlgA gene product (starting at position 167, FIG. 13) was also analyzed for structural tendencies or motifs. The hydropathic plot of mlgA revealed a protein that is highly hydrophobic, suggesting the possibility of membrane-association. Furthermore, using the same algorithms as above (D. Eisenberg, E. Schwartz, M. Komarony and R. Wall (1984) *J. Mol. Biol.* 179:125–142; G. von Heijne (1986a) *Nucl. Acids Res* 14:4683–4690), 4 potential membrane-spanning regions and 2 potential signal sequences for membrane insertion were predicted.

In addition to a functional promoter, sequence analysis of melA revealed a stem and loop structure, beginning at position 1380, immediately downstream of the 3' end of the melA coding sequence. This structure has the attributes of a factor-independent transcriptional terminator, namely a GC dyad stem immediately preceding a stretch of AT rich sequence (T. Platt (1986a) *Ann. Rev. Biochem.* 55:339–372). The presence of an upstream promoter and a transcriptional terminator directly downstream suggests that melA is monocistronic, and expressed as a unique transcript. Northern blotting of total RNA did not reveal significant levels of the melA transcript when initiation only occurred from the melA promoter. Nevertheless, the proposal that the melA transcript is monocistronic is consistent with the Northern blots of RNA derived from *E. coli* carrying pMC3B, a construct encoding a fortuitous lacZ'::mela operon fusion (Table 2). The sizes of the two transcripts, 1.6 kb and 1.3 kb, were consistent with those predicted from transcriptional initiation at the lacZ and melA promoters and termination at the putative factor-independent terminator downstream of melA.

There are 114 bp of leader sequence between the putative melA promoter and the start codon, and in this region there are two mutually exclusive stem and loop structures. The free energies for the upstream (−6.8 dG) and the downstream (−8.2 dG) stem and loops suggest a significant, yet plastic, structure (I. Tinoco, P. N. Borer, B. Dengler, M. D. Levine, O. C. Uhlenbeck, D. M. Crothers, and J. Gralla (1973) *Nature New Biology* 264:40–41). The occurrence of sequencing artifacts (termination with all four dideoxynucleotides) indicative of secondary structure, at several nucleotides directly involved in these putative stem-loop structures, provides in vitro evidence to support these predictions (data not shown).

The sequences are also rich in glycine (8.4% and 14.7%), alanine (9.2% and 15.4%), and arginine (9.2% and 5.6%, respectively). In comparison, the MelA sequence predicts an acidic, protein which is neither highly hydrophobic or hydrophilic. The enzyme is probably cytoplasmic and there is no evidence that it is secreted. The amino acid composition reveals a similar bias against sulfur-containing amino acids, with 1 (0.3%) cysteine and 5 (1.4%) methionine residues. The MelA amino acid sequence is rich in the acidic amino acids glutamate (7.2%) and aspartate (9.2%) as well as isoleucine (9.2%), glycine (8.1%) and phenylalanine (8.1%). Although MelA shares some general structural and compositional tendencies with the Streptomyces enzymes, it shows no significant sequence homology with these proteins. In particular it does not have a distinguishable Type III copper-binding site (J. A. Fee (1978) p.1–60, in J. d. Dunitz, P. Hemmerich, R. H. Holm, J. A. Ibers, C. K. Jorgensen, J. B. Neilands, D. Reinen, and R. J. P. Williams (eds) Vol. 23 *Structure and bonding.* Springer-Verlag, New York) conserved in tyrosinases and hemocyanins (K. Lerch, M. Huber, H. Schneider, R. Drexel, and B. Linzen (1986) *J. Inorg. Biochem.* 26:213–217). In addition, MelA is distinctly different from, and shows no sequence homology to laccase (U. A. Germann, G. Muller, P. E. Hunziker, and K. Lerch (1988) *J. Biol. Chem.* 263:885–896), as well as all of the Type I "blue" copper proteins (J. A. Fee (1978) p.1–60, in J. d. Dunitz, P. Hemmerich, R. H. Holm, J. A. Ibers, C. K. Jorgensen, J. B. Neilands, D. Reinen, and R. J. P. Williams (eds) vol. 23 *Structure and bonding.* Springer-Verlag, New York).

There is preliminary evidence that melanogenesis in *S. colwelliana* is inhibited by the copper-specific chelator diethyldithiocarbanate (DDC) (Dagasan et al, unpublished results). MelA contains 8 histidine residues, the ligand in Type III copper-binding sites of tyrosinases and hemocyanins, and these may be involved in metal ligation via a previously undefined coordination chemistry. Alternatively, in the blue copper proteins such as laccase, the copper is bound via four ligands, a cysteine, a methionine, and two histidines (P. M. Colman, H. c. Freeman, J. M. Guss, M. Murata, V. A. Norris, J. A. M. Ramshaw, and M. D. Venkatappa (1978) *Nature* 272:319–324). A similar multiligand binding site may be functioning in MelA. The inhibition studies described above were conducted with crude or partially purified S. colwelliana D extracts.

Sequence analysis of mlgA. In addition to melA, a second gene, designated mlgA, was cloned and sequenced. Deletion analysis of the region flanking melA indicated that mlgA is not required for melanin synthesis in E. coli, but did not eliminate the possibility that mlgA is involved in melanogenesis in S. colwelliana. Computer analysis of the predicted MlgA amino acid sequence revealed that the protein is predominantly hydrophobic, and is likely to be integrally membrane-associated. Results from in vitro expression and maxicell analyses with constructs encoding MlgA support this prediction. The in vitro expression, in agreement with the sequence, suggested that the protein was 17 kD. However in maxicell analysis, the 17 kD protein was not observed, even for constructs that were verified to encode MlgA by DNA-directed expression and sequence analysis. Rather, a large aggregate that barely entered the gel, was consistently observed in SDS-PAGE analysis of maxicell extracts that encoded intact MlgA, and was absent from those that did not. Maxicells possess membranes, and most cellular processes are still functional, specifically those involved in insertion of proteins into membranes. In contrast, the DNA-directed expression system is truly in vitro, lacking any intact membranes. Considering this, it is likely that MlgA expressed in maxicells, was inserted into membranes, aggregated with itself, and/or with other membrane components, and did not enter the SDS-PAGE gel.

Figure 15:
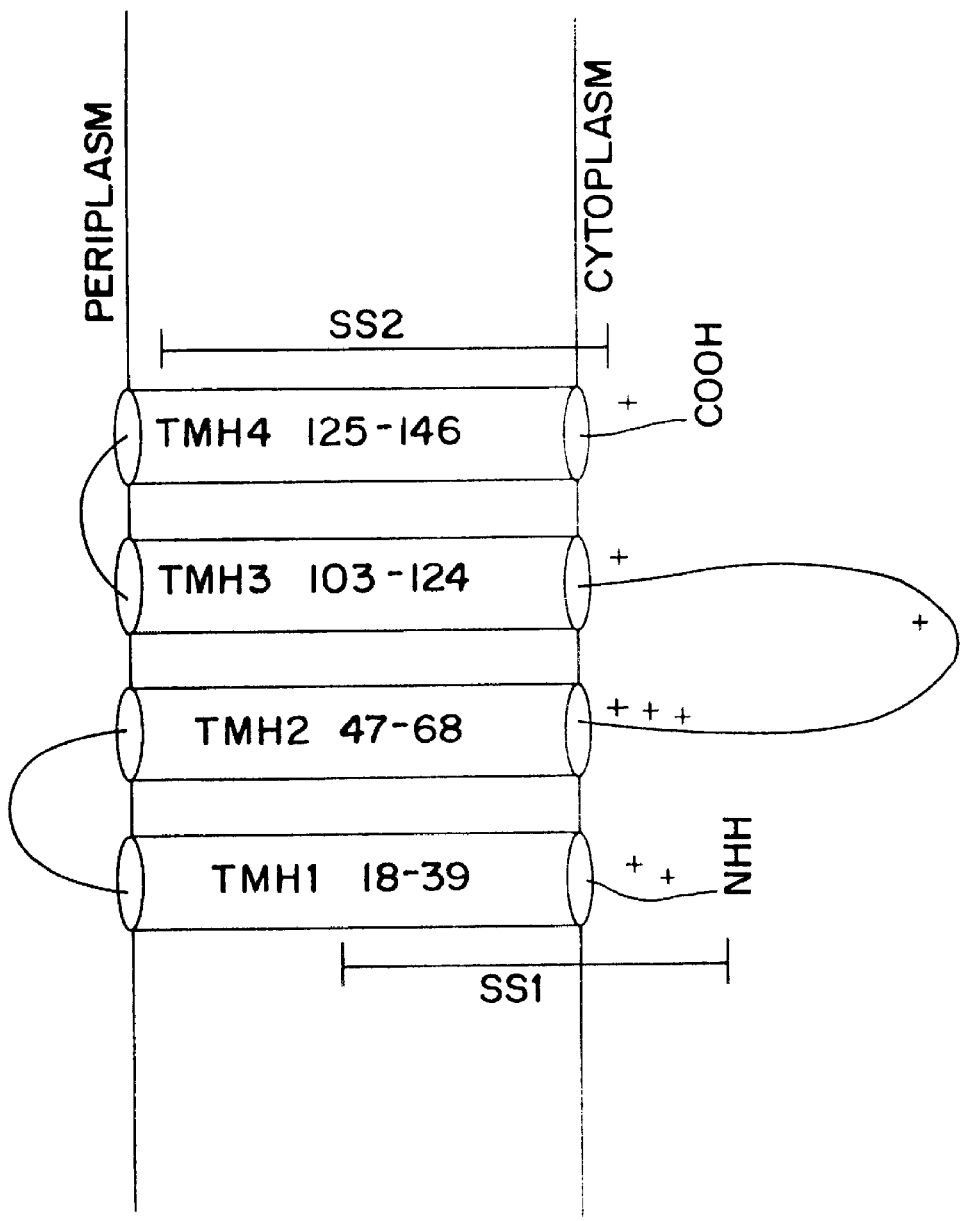
FIG. 15 is the potential membrane orientation of MlgA. Transmembrane helices and potential signal sequences were predicted using the programs of Eisenberg et al (J. Mol. Biol. 179:125–142) and von Heijne (Nucl. Acids Res. 14:4683–4690), and are shown here as rods and bracketed lines, respectively. Both of these programs were accessed using the Intelligenetics PC Gene program. Positively charged amino acid residues are denoted with +signs.
Figure 16:
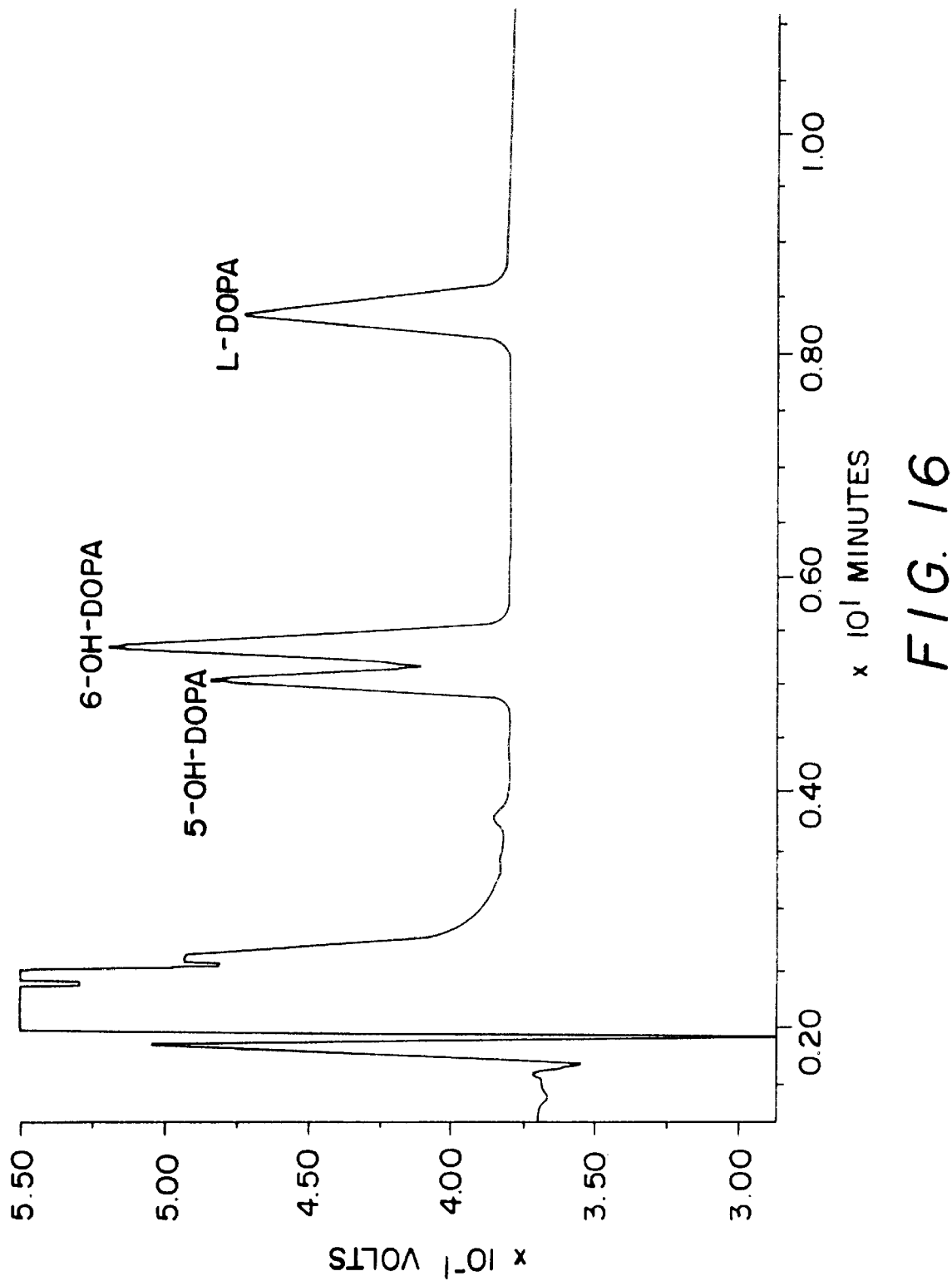
FIG. 16 as an HPLC elution profile of a catecholamine standard set, containing 200 pmole each of 5-OH-DOPA, 6-OH-DOPA, and DOPA. The Waters 460 Electrochemical Detector was set at a potential of 0.7 V and a 20 nA range of sensitivity. The x-axis is elution time and the y-axis is the electrochemical response.

The predicted mlgA gene product is composed of 4 potential membrane-spanning helices and 2 potential signal sequences. Compilation of sequence data from integral membrane proteins reveals a trend in the membrane orientation of these proteins. Interhelical loops of membrane proteins tend to be oriented as a function of the net charge of the region; with positively charged interhelical loops on the cytoplasmic side of the membrane, and neutral or negatively charged regions exposed to the medium (or periplasmic space) (G. von Heijne (1986b) EMBO J. 5:3021:3027; G. von Heijne and Y. Gavel (1988) Eur. J. Biochem. 174:671–678). In light of the placement of membrane-spanning helices and signal sequences one can predict the orientation of a protein relative to the membrane by its charge distribution. The illustration in FIG. 15 is such a prediction, and summarizes the information on the secondary structure of MlgA, offering one potential orientation for the protein in the membrane. In this interpretation, the protein crosses the membrane 4 times with a pair of short segments exposed to the medium or periplasm, and one relatively large interhelical segment on the cytoplasmic side of the membrane. Although this membrane orientation model of MlgA conforms with the above generalizations, it remains hypothetical.

EXAMPLE 9

Determination of the Transcriptional Start Point

Primer extension analysis. For primer extension experiments, a synthetic 30 mer (5'GTTTTGTTCGCTTGCCATGTAAT-TATCCTC-3') (SEQ. ID NO. 3) complementary to the 5' end of melA (nucleotides 304–333) was end-labeled with T4 polynucleotide kinase. The labeled primer (2 pmole) was coprecipitated with total RNA (150 $\mu$g or 6 $\mu$g). The mixture was resuspended in aqueous hybridization buffer and allowed to anneal overnight at 32° C. This mixture was ethanol precipitated and redissolved in 2X reverse transcriptase buffer prior to addition of 50 U of reverse transcriptase and incubation for 2 h at 37° C. The reaction was terminated by addition of 1 $\mu$l 0.5M EDTA, and RNA was removed by RNase A digestion (1 $\mu$l of 6 $\mu$g/ml stock) at 37° C. for 30 min. Following incubation the reaction mixture was diluted to 200 $\mu$l with 1X TE buffer, phenol/chloroform extracted, and ethanol precipitated. The pellet was resuspended in 4 $\mu$l of 1X TE prior to addition of 3.5 $\mu$l of gel loading buffer and heating (5 min at 85° C.). The extension products were electrophoresed on a 6% denaturing polyacrylamide gel (2 $\mu$l/lane) alongside a dideoxy sequence ladder generated with the same primer. The site of transcriptional initiation indicated in FIG. 4 is supported by several lines of evidence. Primer extensions were performed using the melA-specific 30 mer and total RNA isolated from S. colwelliana D, E. coli JM101 carrying pUC19, and E. coli JM101 carrying pMC3A or pMC3B. pMC3A and pMC3B contain the same 1.9 kb insert ligated in opposite orientations in pUC19 (Table 2). The pMC3B-derived RNA produced readily detectable melA extension products. The size of the major extension product predicted transcriptional initiation from a thymidine residue at position 201. The melA gene in pMC3B is likely to be transcribed from the pUC19 lacZ promoter and the melA promoter as evidenced by the Northern blot analyses. Thus, the larger extension products observed in this reaction probably correspond to premature termination of transcripts initiating from the lacZ promoter. At significantly higher RNA concentrations E. coli JM101 pMC3A and S. colwelliana-derived RNAs, produced visible extension products that although faint, also predicted initiation at position 201. No extension products were produced from E. coli pUC19-derived RNA. Interestingly, the S. colwelliana D-derived RNA directed synthesis of several larger bands in addition to the primary extension product.

In support of this prediction, construct pMC6A, only initiating transcription from the melA promoter, and deleted for all sequence upstream of cytosine 166, was capable of directing melanin formation in E. coli. This establishes that all of the required sequences are within 200 nts of the translational start site. Furthermore, the promoter predicted from the primer extensions is the best overall sigma $^{70}$ consensus sequence within this region. These results supported the primer extension data and were consistent with the prediction of transcription initiation at position 201 in E. coli and S. colwelliana D.

EXAMPLE 10

Enzymatic Assay for Tyrosinase Activity

Crude lysates and Bio-Gel P100 chromatographic fractions were prepared as described above, and made 1 mM for EDTA. All reagents were dissolved in 10 mM $PO_4$ buffer (pH-6.8 in HPLC grade $H_2O$) and passed through a 0.2 $\mu$m filter. 80 $\mu$l of 4 mM tyrosine, 9.0 $\mu$l of 10 mM $PO_4$ buffer (pH 6.8), and 1 $\mu$m of 20 mM ascorbic acid were mixed in an Eppendorf microfuge tube. 10 $\mu$l of the enzyme fraction or lysate was added to this, mixed thoroughly, and incubated for 10 min at 25° C. Following incubation, 90 $\mu$l of the reaction mixture were withdrawn and mixed with 10 $\mu$l of 1N perchloric acid to terminate the reaction and precipitate total protein. This was centrifuged in an Eppendorf microfuge (6,400×g) for 3 min, 70 $\mu$l of the supernatant was withdrawn, passed through a 0.2 $\mu$m microfilter, and placed on ice.

The reaction products were separated on isocratic reverse phase HPLC by loading 20 $\mu$l of the acidified filtrate onto a Econosphere C18 reverse phase column (250 mm×4.6 mm)

(Alltech Associates Inc., State College, Pa.). The mobile phase was run at a flow rate of 1.5 ml/min (app. 2,500 psi) with a Waters 501 HPLC Pump (Millipore Corp., Waters Division, Milford, Mass.). The column eluant was analyzed with a Waters 460 Electrochemical Detector set at a 0.7 V potential against the reference electrode and a sensitivity range of 20 nA. The electrochemical response data was stored and peaks integrated via direct interface of the detector with the Waters Baseline 810 Chromatography Workstation program installed on an NEC APC IV personal computer (Boxborough, Mass.). Standards of DOPA, 6-OH-DOPA, 5-OH-DOPA were run daily. All standards were obtained from Sigma, except for the 5-OH-DOPA, that was a gift from Dr. Peter Sorter of Hoffman-La Roche Pharmaceuticals. Enzyme activity was defined as the peak area (microvolt-sec response)/mg total protein/min.

Figure 18A:
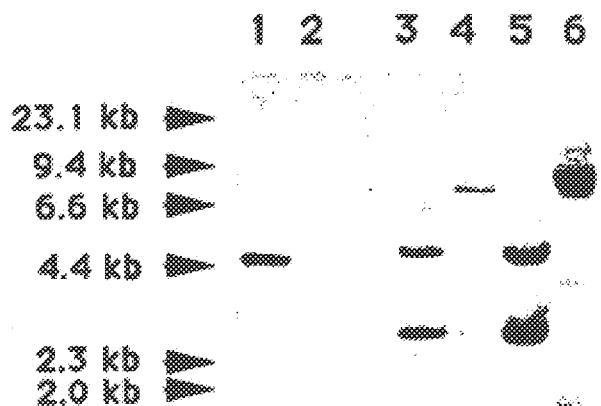
FIG. 18 shows hybridizations with melA-specific and CAC-7 specific probes. (A) Southern blot of HindIII-digested pMC3A (lane 1), PstI-digested genomic DNA from S. colwelliana D (lane 2), S. colwelliana C72 (lane 6). The blot was hybridized with the melA-specific probe (see Materials and Methods). (B) Southern blot of HindIII-digested pCAC7 and identical genomic DNA digests as in A. The blot was hybridized with the CAC7-specific probe (see Materials and Methods). For both blots, right arrows indicate mobilization of HindIII-digested phage lambda size markers.
Figure 18B:
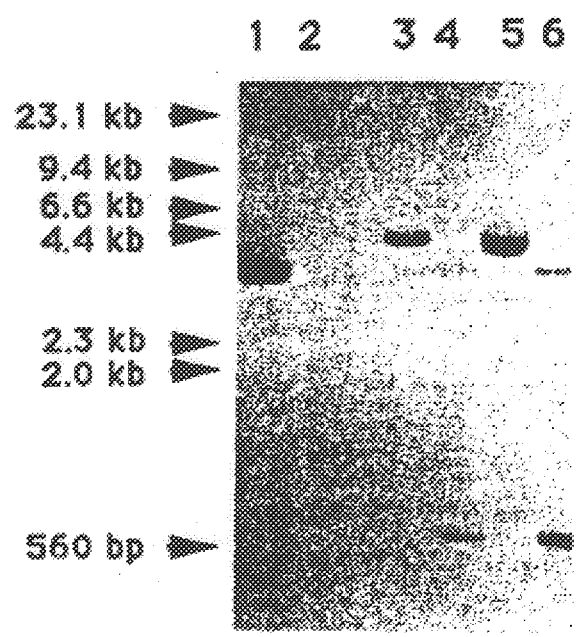

Due to small daily variations in elution times standards were run with all assays. A typical standard set containing 200 picomoles of DOPA, 6-OH-DOPA, and 5-OH-DOPA with elution times of 8.4, 5.4, and 4.5 min (respectively) is shown in FIG. 18 (The large out of range peak observed at 2–3 min is ascorbic acid).

Analysis of a S. colwelliana D lysate revealed the production of two distinct peaks from incubation with L-tyrosine. One peak eluted at 8.4 min and based on its retention time was presumed to be DOPA. The second peak, eluted at 3.6 min and clearly did not match the elution profiles of either 5-OH-DOPA or 6-OH-DOPA. This compound was designated Tyr-P. The peak that did elute at approximately the same time as 6-OH-DOPA (5.5 min), was much smaller and not always apparent. This may be trihydroxylated product reported to be produced in low levels during enzymatic conversion of tyrosine to DOPA (G. Agrup, H. Rorsman, and E. Rosengren (1982) *Acta Dermato* (Stockholm) 62:371–376); C. Hansson, H. Rorsman, and E. Rosengren (1980) *Acta Dermato Vener.* (Stockholm) 60:281–286; M. E. Morrison, and G. Cohen (1983) *Biochemistry* 22:5465–5467).

In negative controls of the assays, incubated without substrate, DOPA was not detected. However, a substantial amount of Tyr-P was present in the lysate prior to addition of substrate, possibly because Tyr-P has higher stability than DOPA. To verify that this product was being synthesized from tyrosine, and not an alternate substrate prior to lysis of the cells, a time course experiment was designed. In this experiment control assays without tyrosine were incubated in parallel with assays without tyrosine were incubated in parallel with assays containing tyrosine. Aliquots were removed every 10 min and the level ($\mu$volt-sec) of DOPA and Tyr-P were measured. No DOPA peak was detected in negative controls, but it was observed to increase with incubation time in the tyrosine-containing assay. Although present in the negative controls, the amount of Tyr-P did not increase with assay time, but did increase steadily in the tyrosine-containing assay.

Lysates of S. colwelliana D converted tyrosine to at least 2 products, DOPA and Tyr-P, a faster eluting compound of unknown composition. E. coli JM101 carrying the S. colwelliana melA gene, synthesized melanin, and produced Tyr-P but no DOPA. This correlated Tyr-P with the melA gene product and melanin formation in E. coli, but failed to establish that Tyr-P was also a melanin precursor in S. colwelliana D. Conceivably, S. colwelliana D utilizes Tyr-P for alternate purposes, and its intracellular or excreted concentration does not accumulate to sufficient levels for melanin formation.

EXAMPLE 11

Isolation and Characterization of S. colwelliana PIM1, a Spontaneous Pigmentation Mutant A spontaneous pigmentation mutant of S. colwelliana D was isolated. Comparison of this mutant to S. colwelliana D showed it to be deficient in tyrosine-induced pigmentation. The mutant and wild type both produced light brown pigment on MB agar. However, while S. colwelliana D showed the normal enhancement to dense pigmentation when plated on MG agar supplemented with tyrosine and $CuSO_4$, the mutant showed no such increase. This mutant was designated PIM1 (pigmentation mutant 1).

HPLC assays of S. colwelliana PIM1 extracts produced DOPA levels roughly equivalent to strain D, but synthesized only trace levels of Tyr-P. This trace amount was a small peak observed eluting with the same retention time as Tyr-P. This peak did not increase with increasing assay time (data not shown). The results from HPLC assays of extracts prepared from S. colwelliana D, E. coli JM101 carrying pUC19 or pMC3B, and S. colwelliana PIM1 are summarized in Table 3. The S. colwelliana PIM1 extracts appeared to synthesize less DOPA than S. colwelliana D, but whether this variation reflects a true difference in DOPA-synthesizing activity between the strains is not known.

TABLE 3

Correlation of MelA with Tyr—P production

| Strain[b] | MelA[c] | DOPA | Tyr—P |
|---|---|---|---|
| S. col. D | + | $7.8 \times 10^6$ | $1.7 \times 10^6$ |
| S. col. PIM1 | − | $2.8 \times 10^6$ | trace[d] |
| E. coli JM101 [PUC19][e] | − | 0 | 0 |
| E. coli JM101 [pMC3B], 1PTG[f] | + | 0 | $7.3 \times 10^5$ |

[a]Obtained from calculating peak area minus peak area in negative controls
[b]French-pressed, 0.22 $\mu$m filtered crude lysates
[c]Presence of MelA as determined by immunostaining electrotransfers of SDS-PAGE gels with anti-MelA-Lacz
[d]A small peak that did not increase with assay time was detected for this lysate
[e][ ] denotes plasmid-carrier state
[f]Induced with IPTG (100 $\mu$g/ml)

Equal amounts of total protein from S. colwelliana D and S. colwelliana PIM1 were separated by SDS-PAGE, electrotransferred to nitrocellulose, and immunostained with the anti-MelA-LacZ serum. This revealed that S. colwelliana D synthesized the expected low amount of MelA, but PIM1 synthesized no detectable MelA.

The spontaneous pigmentation mutant S. colwelliana PIM1, does not produce the dense brown pigment characteristic of S. colwelliana D on tyrosine/$CuSO_4$ supplemented media. Extracts from this mutant convert tyrosine to DOPA, as in S. colwelliana D, but do not produce detectable levels of Tyr-P. Furthermore, there is no detectable MelA in PIM1 extracts. These results also correlated MelA activity in S. colwelliana with the synthesis of Tyr-P and with a distinct pigmentation phenotype, thus lending convincing evidence for the direct role of MelA in melanin synthesis.

The nature of the PIM1 mutation. The mutation leading to the PIM1 phenotype dramatically reduces tyrosine-stimulated melanin biosynthesis in S. colwelliana. It also disrupts MelA and Tyr-P synthesis. The simplest explanation is that the mutant has a lesion in the melA gene, thus no Tyr-P is synthesized. However, several observations suggest that the PIM1 phenotype may be one manifestation of a more complex deficiency. The mutant is somewhat less robust than S. colwelliana D, as judged by growth on plates as well as cell densities in liquid culture. In addition, the protein profile of PIM1 whole cell extracts (silver stained gel) had several notable differences in addition to the lack of MelA. For example, several low molecular weight PIM1 bands are not seen in S. colwelliana D, and vice versa. This may reflect a lesion in an S. colwelliana gene that is affecting the synthesis of several proteins including MelA.

Alternatively, MelA itself may mediate this affect, either directly or indirectly by affecting cellular metabolism. The generation of two distinct reaction products, DOPA and Tyr-P, suggests that more than one melanin synthesis mechanism is functioning in S. colwelliana D.

EXAMPLE 12

Construction of the Chloramphenicol Mutagenesis Cassette CAC7

Efficient antibiotic resistance markers are required for marker replacement mutagenesis. Preferably, this marker should impart high level resistance to an antibiotic to which the target organism is particularly susceptible. Testing of various MICs on MB agar revealed that S. colwelliana D was relatively resistant to many of the more commonly used antibiotics. However, S. colwelliana D exhibited high sensitivity to chloramphenicol, which inhibited growth on MG agar at concentrations as low as 1 $\mu$g/ml. Resistance to chloramphenicol is derived from the activity of chloramphenicol acetyltransferase (CAT), an enzyme that inactivates the antibiotic via acetylation. In Gram-negative bacteria, several different elements carry and express the CAT gene (T. J. Foster (1983) *Microbiol. Rev.* 47:361–409). One of the most common of these CAT elements is the Tn9 transposon, carried on the cloning vector pBR325 (F. Bolivar (1978) *Gene* 4:121–136).

Figure 17A:
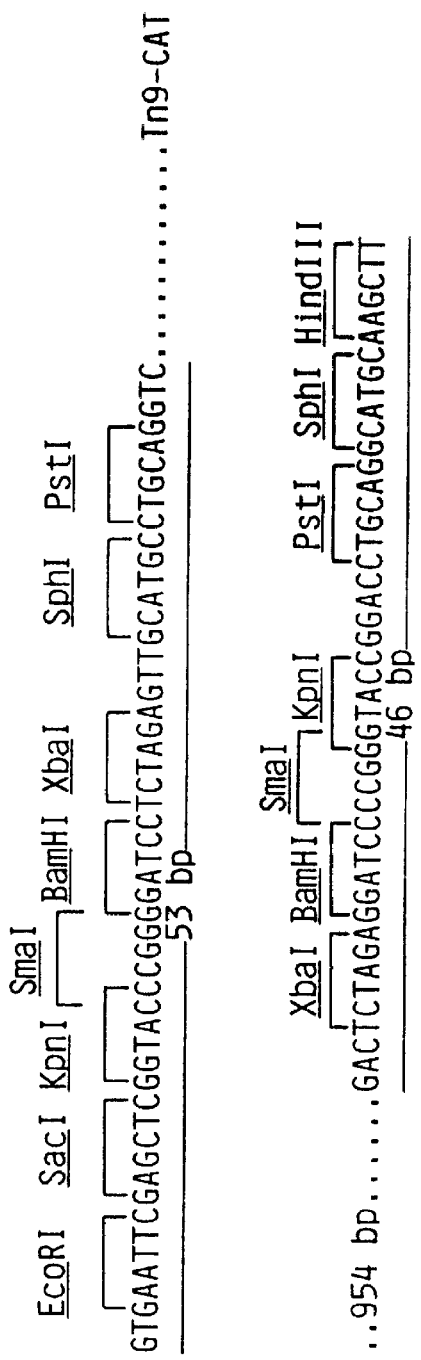
FIG. 17 (A) is the sequence of multiple cloning site polylinkers; (B) is a diagrammatic representation of CAC7 and DNA Restriction sites: B-BamHI, Bs-BstBI, E-EcoRI, H-HindIII, Hc-HincII, K-KpnI, P-PstI, S-SacI, Sm-SmaI, Sp-SphI, X-XbaI. [SEQ. ID NOS. 8 & 9]
Figure 17B:
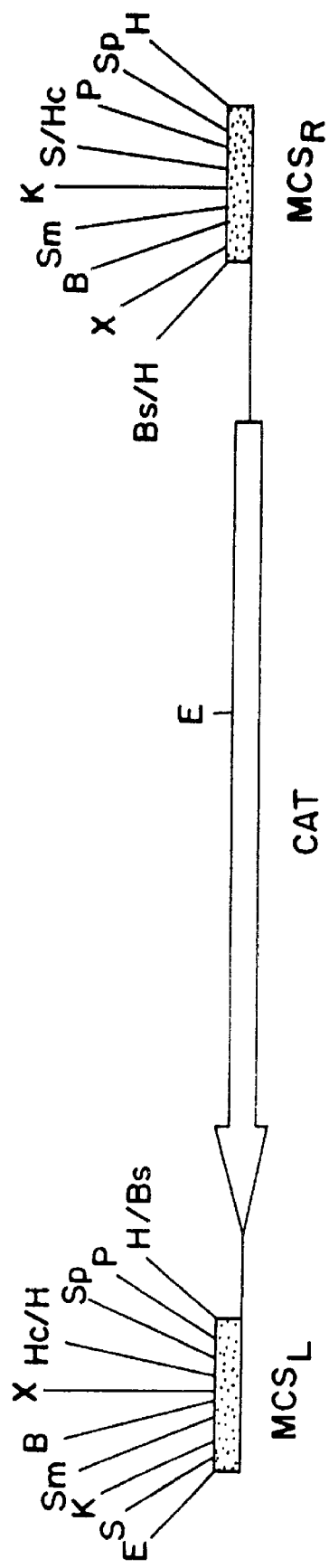

A $Cm^R$ cassette derived from the pBR325 Tn9 CAT gene was constructed for use in marker replacement mutagenesis among other purposes (Fuqua, in review). The 952 bp BstBI fragment of pBR325 was blunt-ended with Klenow fragment, and ligated into HincII-cleaved pUC19. This ligation transformed into *E. coli* JM101, and $AP^R Cm^R$ transformants were selected. The inserts of these recombinant plasmids were restriction endonuclease mapped and a construct oriented with the CAT gene reading away from the EcoRI site of the pUC19 multiple cloning site was used for further manipulation. This construct was double-digested with SacI and HindIII to generate two cleavage products, of which the smaller fragment carried the intact CAT gene with half of the HincII-split multiple cloning site on each end. The extensions generated from this digestion were digested with Mung Bean Nuclease and this fragment was ligated into the HincII site of pUC19. The ligation mixture was transformed into *E. coli* JM101, and $Ap^R Cm^R$ transformants were selected. Two possible orientations were generated, one with a tandem half of the multiple cloning site on each end, and the other with reconstructed multiple cloning sites on each end. The plasmids carried in these transformants were screened by restriction endonuclease cleavage to isolate the latter, desired configuration. One such plasmid agreed with the predictions, and double-stranded sequencing of the polylinker at each end of the cassette confirmed the sequence for these regions of the construct. The plasmid was designated pCAC7, and the CAT cassette it contains, CAC7, is illustrated in FIG. 17. The CAC7 cassette is extremely versatile, and proved to a useful tool in later manipulations.

EXAMPLE 13

In vitro Insertional Mutagenesis of melA and Generation of a Mobilizable Construct The CAC7 cassette was utilized to inactivate the melA gene in vitro. A 300 bp BglII fragment in the 5' coding region of melA was excised and replaced with the BamHI-cleaved CAC7 cassette. This ligation was transformed into *E. coli* JM101, and plated on LB agar supplemented with Ap, Cm, tyrosine, and $CuSO_4$. All of the resulting $Ap^R Cm^R$ transformants were Mel$^-$. The plasmids carried by these transformants were mapped using restriction endonucleases and one recombinant plasmid (pB3A7) with the CAT gene inserted in the opposite orientation to melA was chosen for further manipulation.

For insertion into pGP704, a 2.5 kb fragment carrying all of the melA coding sequence, interrupted by the CAC7 cassette, was liberated from pB3A7 by double digestion with BamHI and NheI. Cleavage of pGP704 with BglII and XbaI produced compatible extensions for ligation with BamHI and NheI extensions, respectively. These two fragments were ligated together and the reaction was transformed into *E. coli* SY327/lambda pir (Table 4), a host with a lysogenically encoded pir gene that transforms at higher efficiencies than *E. coli* SM10/lambda pir. All transformants were $Ap^R Cm^R$ Mel$^-$ and successful insertion of the melA::CAC7 fragment into pGP704 was verified with restriction endonuclease mapping. A 6.2 kb recombinant plasmid designated pGB3A7 was purified from *E. coli* SY327/lambda pir and retransformed into *E. coli* SM10/lambda pir.

TABLE 4

BACTERIAL STRAINS AND PLASMIDS

| Strain or plasmid | Relevant characteristics |
|---|---|
| *S. colwelliana* | |
| D | diffusable pigment |
| DR5 | spontaneous Rif$^R$ mutant of strain D |
| PIM1 | spontaneous pigmentation mutant, MelA- |
| PIM1R | spontaneous Rif$^R$ mutant of strain PIM1 |
| DR5::C71 | melA::CAC7, pB3A7 plasmid insertion, pigment-, MelA-, Cm$^R$ |
| DR5::C72 | melA::CAC7, pB3A7 plasmid insertion, PIM1-like, MelA-, Cm$^R$ |
| *E. coli* | |
| JM101 | host strain, α-complemen-tation strain |
| SY327/λpir | λpir, recA56, high efficiency transformation host for pGP704 cloning |
| SM10/λpir | λpir, recA:RP4-2-Rc::Mu Km, mating strain for pGP704 conjugal transfer |
| Plasmids | |
| pUC19 | cloning vector for α-complementation systems, AP$^R$, Lac+ |
| pBR325 | cloning vector, AP$^R$, Cm$^R$, Tc$^R$ |
| pRK290 | broad host range mobilizable vector, Tc$^R$ |
| pGP704 | oriR6K, mobRP4 mobilizable cloning vector, AP$^R$ |
| pMC3A | 1.9 kb HincII-HincII fragment of pMC2 in pUC19, AP$^R$, Mel+ |
| pMC6A | 1.3 kb NspI-NspI fragment of pMC3A in pUC19, AP$^R$, Mel+ |
| pCAC7 | 954 bp BstBI-BstBI fragment of pBR325 in pUC19 plus multiple cloning sites, contains CAC7 cassette, AP$^R$, Cm$^R$ |
| pB3A7 | melA::CAC7, BamHI-cleaved CAC7 cassette inserted in pMC3A deleted for 300 bp BglII-BglII, AP$^R$, Cm$^R$, Mel- |
| pM6A7 | mlgA::CAC7, SmaI-cleaved CAC7 cassette inserted in the MscI site of pMC6A, AP$^R$, Cm$^R$, Mel+ |
| pGB3A7 | 2.5 kb BamHI-NheI fragrnent of pB3A7 inserted in Bg/II-cleaved pGP704, mobilizable, AP$^R$, Cm$^R$, Mel- (melA::CAC7) |
| pRKmel | 2.5 kb BamHI-NheI fragment of pM6A7 inserted in pRK290, broad host range, mobilizable Tc$^R$, Cm$^R$, Mel+ |

The same in vitro mutagenesis strategy was attempted for mlgA, the small gene downstream of melA, but the construct carrying the insertionally mutated gene would not transform into *E. coli* SM10/lambda pir, possibly due to a toxic effect of the truncated mlgA gene product.

Conjugation and insertion mutagenesis of the *S. colwelliana* D melA gene. The mobilizable, broad host range RP4 derivative pRK290 (G. Ditta, S. Stanfield, D. Corgin and R. R. Helenski (1980) *Proc. Natl. Acad. Sci., USA* 77:7347–7351) was altered by the insertion of the CAC7 cassette into the single BglII site to generate pRCAM2 (21 kb), a plasmid imparting $Tc^R$ and $Cm^R$ and capable of replication in a wide variety of Gram-negative bacteria (Fuqua, unpublished results, Quintero et al, manuscript in preparation). Rough estimations of conjugal efficiencies of the *E. coli* SM10/lambda pir mating system with *S. colwelliana* D were determined with pRCAM2. *E. coli* SM10/lambda pir carrying pRCAM2 was mated with *S. colwelliana* DR5 (Table 5), a $Rif^R$ derivative of *S. colwelliana* D generated for this study (Table 4). *S. colwelliana* DR5 $Cm^R$ transconjugants were observed after 3 days of incubation with a conjugal efficiency of approximately $1 \times 10^{-6}$. Low plating dilution of the mating mixture ($>10^{-1}$) resulted in the growth of a lawn of cells, but at the higher dilutions ($10^{-3}$–$10^{-4}$) isolated colonies grew at reasonable densities. Plasmid purifications from randomly selected colonies showed that the $Rif^R$ $Cm^R$ conjugants carried pRCAM2 and that the conjugation was proceeding at an efficiency sufficiently high for marker-driven mutagenesis of *S. colwelliana* D.

TABLE 5

SUMMARY OF MATINGS

| Plasmid[a] | Recipient[b] | Selection[c] |
|---|---|---|
| pUC19 | DR5 | Rif, Cm |
| pRCAM2 | DR5 | Rif, Cm |
| pGB3A7 | DR5 | Rif, Cm |
| pRK290 | DR5 | Rif, Tc |
| pRK290 | PIM1R | Rif, Tc |
| pRK290 | C71 | Rif, Tc |
| pRK290 | C72 | Rif, Tc |
| pRKmel | DR5 | Rif, Cm |
| pRKmel | PIM1R | Rif, Cm |
| pRKmel | C71 | Rif, Tc |
| pRKmel | C72 | Rif, Tc |

[a]*E. coli* SM10/lambda pir was used as the donor strain for all matings
[b]All recipient strains were $Rif^R$
[c]Antibiotic concentrations are given in Table 14

The *S. colwelliana* D melA gene was mutagenized by mating *E. coli* SM10/lambda pir carrying pGB3A7 with *S. colwelliana* DR5. Because pGP704-derived plasmids will not replicate outside of their specific *E. coli* hosts, when pGB3A7 was conjugated into *S. colwelliana* DR5d and the transconjugants were placed under Cm selection, only recipients that had gained a chromosomal version of the marker would grow. A region of melA homology flanks both sides of the CAC7 cassette on pGB3A7, thus targeting the recombinational event to the chromosomal melA gene. Conjugation of *E. coli* SM10/lambda pir carrying pUC19 with *S. colwelliana* DR5 served as a negative control (Table 6). Visible colonies grew 3 days after the pGB3A7 mating. Several small, slowly growing colonies were also observed after 1 week of incubation in pUC19 matings. Replica plating of the pGB3A7 and pUC19 transconjugants onto MB agar with Cm, 5 mg/ml tyrosine, and 5 μg/ml $CuSO_4$ revealed that the majority (90%) of pGB3A7-derived transconjugants showed variation in melanin synthesis. Of these, approximately 905 pigmented identically to *S. colwelliana* PIM1 (Mel⁻), while 10% appeared pigmentless (Pig⁻). None of the slower growing colonies from the pUC19 mating varied in pigmentation. Each class of pGB3A7 mutant, Pig⁻ and Mel⁻, was notably different from *S. colwelliana* DR5. To verify that these colonies were not simply spontaneous rifampicin resistant *E. coli* donors, they were replica plated on LB agar and incubated at 37° C. and 25° C. *S. colwelliana* has a strict requirement for at least 1.5% NaCl and does not grow about 30° C. (R. M. Weiner, A. M. Segall and R. R. Colwell (1985) *Appl. Environ. Microbiol.* 49:83–90). Consequently, these transconjugants, being salt limited, did not grow at either temperature. In addition, transconjugants plated on MG agar grew readily at 25° C., but did not grow at 37° C. The mutants, Mel⁻ and Pig⁻, were designated *S. colwelliana* C72 and *S. colwelliana* C71, respectively.

TABLE 6

MEDIA AND BUFFERS

| Name | Composition |
|---|---|
| MEDIA | |
| LB (Luria-Bertani) | 10 g/L Bacto-Tryptone |
| | 5 g/l yeast extract |
| | 5 g/L NaCl |
| M63 minimal media | 10 μg/L Thiamine |
| | 0.1 mM $MgSO_4$ |
| | 0.4% glucose |
| | 100 ml/L 10X M63 salts |
| 10X M63 salts | |
| | 0.22M $KH_2PO_4$ |
| | 0.4M $K_2HPO_4$ |
| | 0.15M $(NH_4)SO_4$ |
| | 18 μM $FeSO_4$ |
| MB (Marine Broth 2216 | 37.4 g/L dried Marine Broth |
| TB (Teriffic Broth) | 24 g/L yeast extract |
| | 12 g/L Bacto-Tryptone |
| | 4 ml/L glycerol |
| | 100 ml/L $K_2HPO_4$ buffer |
| $K_2HPO_4$ buffer | |
| | 0.17M $KH_2PO_4$ |
| | 0.72M $K_2HOP_4$ |
| BUFFERS | |
| Aqueous Hybridization Buffer | 40 mM piperazine-N-N'-bis[2-ethanesulfonic acid] (PIPES) |
| | 1 mM EDTA |
| | 400 mM NaCl |
| | 80% deionized formamide |
| DNA/RNA Hybridization Solution | 6X SSPE |
| | 100 μg/ml denatured salmon sperm DNA |
| DNA Prehybridization Solution | 6X SSPE |
| | 0.5% skim milk |
| | 100 μg/ml denatured salmon sperm DNA |
| DNAse I Buffer | 100 mM sodium acetate |
| | 5 mM $MgSO_4$ |
| | pH-5.0 |
| Denaturation Solution | 0.2 N NaOH |
| | 2 mM EDTA |
| Denaturing Gel Loading Buffer | 905 formamide |
| | 20 mM EDTA |
| | 0.05% bromophenol blue |
| | 0.05% xylene cyanol |
| Klenow Buffer | 40 mM $KPO_4$, pH-7.5 |
| | 6.6 mM $MgCl_2$ |
| | 1 mM 2-mercaptoethanol |
| Ligation Buffer | 3 mM Tris-HCl, pH-7.8 |
| | 10 mM $MgCl_2$ |
| | 10 mM dithiothreitol |
| | 0.5 mM ATP |
| Lysis Buffer | 2% sodium dodecylsulfate (SDS) |
| | 10 mM EDTA |
| 1X MOPS Buffer | 20 mM (morpholino)propane-sulfonic acid (MOPS) |
| | 8 mM sodium acetate |

TABLE 6-continued

MEDIA AND BUFFERS

| Name | Composition |
| --- | --- |
| Mung Bean Nuclease Buffer | 1 mM EDTA<br>pH-7.0<br>50 mM sodium acetate<br>30 mM NaCl<br>1 mM ZnSO$_4$<br>pH-5.0 |
| Protoplasting Buffer | 15 mM Tris-Cl, pH-8.O<br>0.45 M sucrose<br>8 mM EDTA |
| Protoplast Lysis Buffer | 10 mM Tris-Cl, pH-8.0<br>10 mM NaCl<br>1.5% SDS |
| RNA Gel Loading Buffer | 50% glycerol<br>1 mM EDTA<br>0.25% bromophenol blue<br>0.25% xylene cyanol |
| RNA Prehybridization Solution | 6X SSPE<br>5X Denhardt's solution<br>100 μg/ml denatured salmon sperm DNA |
| 50X Denhardt's solution | |
| RNA Sample Treatment Buffer | 2.5 g/L BSA (Pentax Frac. V)<br>2.5 g/L Ficoll type 400<br>2.5 g/L polyvinylpyrolidine<br>6.6% formaldehyde<br>50% formamide<br>1X MOPS buffer |
| 2X Reverse Transcriptase Buffer | 100 mM Tris-Cl, pH-7.6<br>120 mM KCl<br>20 mM MgCl$_2$<br>10 mM each deoxyribonucleo-side triphosphates (dNTPS)<br>2 mM dithiothreitol<br>2U/μl RNAsin<br>100 μg/ml actinomycin D |
| SSPE (saturated saline-phosphate-EDTA) | 150 mM NaCl<br>10 mM NaH$_2$PO$_4$<br>10 mM EDTA<br>pH-7.4 |
| T4 Polynucleotide Kinase | 70 mM Tris-Cl, pH-7.6<br>10 mM MgCl$_2$<br>5 mM dithiothreitol |
| TAE (Tris-Acetate-EDTA) Buffer | 40 mM Tris-acetate<br>1 mM EDTA |
| TE (Tris-EDTA) Buffer | 10 mM Tris-Cl, pH-7.4<br>1 mM EDTA |
| TBE (Tris-Borate-EDTA) | 100 mM Tris-Cl<br>83 mM boric acid<br>1 mM EDTA |
| Tris-buffered sucrose | 10 mM Tris-Cl, pH-8.0<br>25% sucrose |
| Tris-saturated phenol/chloroform | 50% phenol (0.1M Tris sat.)<br>50% chloroform |
| Wash Buffer I | 2X SSPE<br>0.01% SDS |
| Wash Buffer II | 0.2X SSPE<br>0.01% SDS |

EXAMPLE 14

Hybridization of Genomic Blots from *S. colwelliana* C71 and C72 DNA to melA and CAC7 Specific Probes Chromosomal DNA was isolated from *S. colwelliana* C71 and *S. colwelliana* C72. These DNA preparations were digested in separate reactions with EcoRI and PstI restriction endonucleases. Following digestion, two identical agarose gels were loaded with half of each digest, separated electrophoretically, and capillary transferred to Zeta-Probe activated nylon membranes under alkaline conditions (K. C. Reed and D. A. Mann (1985) *Nucl. Acids Res.* 13:7207–7221). Two gene probes, one specific for the larger of the two EcoRI fragments of CAC7 (FIG. 17) and the other specific for the carboxy terminal coding region of melA, were generated using the Polymerase Chain Reaction and specific oligonucleotide primers. These were radiolabeled with $^{32}$P and hybridized to the genomic blots at high stringency. Previous hybridizations of the cloned melA gene to PstI-digested *S. colwelliana* genomic DNA and a positive control of the same digest (FIG. 18, Lane 2; the 4.2 kb band in this blot is light due to degradation of the control DNA) identified the predicted 4.2 kb fragment. In contrast to this, for both the C71 and C72 digests, the melA-specific probe hybridized with two PstI fragments, 5.0 kb and 3.0 kb. The same probe also hybridized with two EcoRI fragments, 8. kb and 1.4 kb. The presence of two hybridizing PstI fragments and their combined size (8.0 kb, approximately 3.8 kb larger than the *S. colwelliana* D PstI fragment) indicated that the site-specific mutagenesis of the *S. colwelliana* D melA gene had successfully inactivated the gene by insertion of the entire pGB3A7 plasmid via a single crossover event (a double crossover event would result in a single hybridizing fragment of approximately 4.0 kb). It also demonstrated that the melA genes of each mutant, C71 (Pig$^-$) and C72 (Mel$^-$) were identical at the gross structural level.

Hybridization with the CAC7-specific probe identified one PstI fragment, identical in size (5.0 kb) to the larger of the two PstI fragments identified with the melA-specific probe. The EcoRI digests revealed the predicted short CAC7 fragment of approximately 600 bp, and a larger, faintly hybridizing fragment of 4.1 kb. As expected, genomic PstI digests of *S. colwelliana* D DNA did not hybridize with the CAC7-specific probe. Recombination initiation downstream of the inserted CAC7 cassette of pGB3A7 predicted that hybridizations of PstI-digested DNA with the CAC7 and melA probes would share the smallest of two MelA-reactive bands. Instead, these hybridizations shared the 5.0 kb fragment, the larger of the two, indicating recombination initiation had occurred upstream of the CAC7 cassette. Furthermore, the results also suggest that the integration occurred upstream of the chromosomal EcoRI site. The CAC7 cassette shares a short stretch of identity with the pGP704 multiple cloning site, thus in addition to hybridizing to the short 0.6 kb EcoRI fragment, it also weakly hybridizes with a larger EcoRI fragment. If the pGB3A7 plasmid had integrated at a site downstream, the EcoRI site would have been undisturbed and a fragment at least 3.5 kb larger than the largest MelA-reaction PstI fragment would have hybridized to the CAC7 probe. Instead, the CAC7 probe identified a fragment of 4.1 kb and indicated that the chromosomal EcoRI site was displaced to directly downstream of the integrated plasmid.

EXAMPLE 15

Immunostaining and HPLC Activity of Site-Specific Mutants

Cell extracts from *S. colwelliana* C71 (Pig$^-$) and C72 (Mel–) and a *S. colwelliana* DR5 (Mel$^+$) control were separated electrophoretically on SDS-PAGE, electrotransferred to a nitrocellulose membrane, and immunostained with the anti MelA-LacZ serum. No 41 kD protein was detected, demonstrating the absence of melA from both of these mutants, while *S. colwelliana* DR5 stained as expected. HPLC assays of these extracts revealed that C71 and C72 produced expected amounts of DOPA, but neither synthesized Tyr-P.

EXAMPLE 16

Complementation Analysis of melA Mutants

In order to conduct complementation analysis of the mutants, the melA gene was cloned into the broad host range plasmid pRK290. A SmaI-cleaved CAC7 cassette was ligated into the single MscI site of pMC6A. This inserted CAC7 1 codon downstream of the start site of mlgA and thus did not show the toxic effect of insertion into mlgA observed in earlier experiments, and also did not interfere with melA expression as evidenced by the Mel[+] phenotype in E. coli carrying this construct (pM6A7). The plasmid pM6A7 was digested with SmaI and HindIII to liberate a 2.3 kb fragment prior to treatment with Klenow fragment to generate blunt ends. The pRK290 vector was cleaved at the BglII site, treated with Klenow fragment, and ligated with the pM6A7 fragment. This ligation was transformed into E. coli JM101 and Tc[R]Cm[R] Mel[+] colonies were isolated. Plasmid purified from these transformants verified that the pM6A7 SmaI-HindIII fragment had been successfully inserted into pRK290, and this new plasmid was designated pRKmel. This plasmid carries an RP4 origin of replication, functional mob sequences, and a tetracycline resistance marker as well as the CAT and melA genes.

For conjugal transfer of the wild type melA gene into the insertion mutants C71 and C72 as well as S. colwelliana D and S. colwelliana PIM1, pRKmel was transformed into E. coli SM10/lambda pir. E. coli SM10/lambda pir derivatives carrying pRKmel or pRK290 (negative control) were conjugated, in separate matings, with S. colwelliana DR5, S. colwelliana PlMlR, S. colwelliana C71 and S. colwelliana C72.

Transfer of pRKmel into S. colwelliana DR5 had no visible effect on the Mel[+] phenotype, which was identical to S. colwelliana dr5 WITH Prk290. In contrast, transfer of pRKmel into S. colwelliana PlMlR resulted in restoration of the Mel[+] phenotype, while transfer of pRK290 had no effect.

Transfer of pRKmel into S. colwelliana C72 restored the Mel[+] phenotype, while pRK290 had no effect. Interestingly, melanin formation was increased even on MB agar without supplemented tyrosine or copper, implying that melA also contributes to total pigmentation under "normal" conditions.

Transconjugants of S. colwelliana C71 that received pRKmel remained non-pigmented, identical to those that received pRK290. The results of this complementation experiment are summarized in Table 7.

TABLE 7

LACCASE COMPARISON

| Organism | Enzyme[a] Mass | Subunit[b] Mass | Copper[c] subunit |
|---|---|---|---|
| Neurospora crassa strain OR | 68.2 | 68.2 | 4 |
| Neurospora crassa strain TS | 68.1 | 68.1 | 4 |
| Aspergillus nidulans | — | 67.9 | 4 |
| Botrytis | 56 | 56 | 4 |
| Lactarius | 67 | 67 | 4 |
| Podospora | 390 | 71[d] | 4 |
| Peach | 73.5 | — | 2 |

[a]Molecular mass of native protein in kilodaltons (kD)
[b]Molecular mass of subunit(s) in kiladaltons (kD)
[c]Copper ions bound per subunit
[d]Isozymic forms reported

EXAMPLE 17

Identification of the Tyr-P Product

Bacterial cultures. Shewanella colwelliana strains were cultured in Marine Broth 2216 (MG; Difco Laboratories, Detroit, Mich.) at 25° C. with vigorous aeration. E. coli, transformed with the plasmid pMC3B, containing the cloned melA gene from S. colwelliana, was grown at 37° C. in Luria Broth (LB).

An unidentified bacterium was isolated as a contaminant in our laboratory. This fortuitous organism grew on 4 mM tyrosine in 10 mM phosphate buffer (pH=6.8) as the sole medium. This bacterium metabolized tyrosine and slowly accumulated high concentrations of Tyr-P. These cultures eventually turned pink and the deep maroon. This strain is designated SLC-PT1.

Assays for melA activity. Crude lysates (10 μl) from the French Press were incubated in a 100 μl reaction volume containing 3.2 mM tyrosine and 0.2 mM ascorbic acid in 10 mM phosphate buffer (pH=6.8). After 15 min, 11 μl of 1N perchloric acid was added, and following centrifugation, an aliquot was injected onto the HPLC.

Sample preparation. Culture supernatants were sampled at the indicated times and immediately acidified with 0.1 volumes of 1.0N perchloric acid (PCA). Following centrifugation at 15,000×g for 5 min, the samples were injected directly onto the HPLC system.

Bacterial lysates were prepared by processing harvested cells through a French Press. Cells were harvested by centrifugation of cultures at 16,000×g for 10 min at 4° C. After washing with sodium phosphate buffer, 10 ml of washed cells were disrupted using the French Press at 15,000 psi (40 ml cell). The lysate was cleaned (16,000×g, 10 min, 4° C., filtered through a 0.2 μm filter and stored at −20° C.

Electrochemical detection of Tyr-P. Samples were analyzed with a Waters HPLC system fitted with a 4.6×250 mm, $C_{18}$, reverse-phase column (Alltech, State College, Pa.). The mobile phase consisted of 5% acetonitrile (v/v) in 10 mM monochloroacetic acid, 1.3 mM EDTA and 1.3 mM sodium octyl sulfate (pH=2.6). Peaks eluting from the column were detected with a Waters 460 electrochemical detector set at an oxidizing potential of 700 mV. Data were analyzed using the Waters Baseline 810 software. This method was also useful for detecting Mason-Raper intermediates.

Purification of Homogentisic Acid (HGA: formerly Tyr-P). To purify enough HGA for analysis by NMR and mass spectroscopy, the bacterium SLC-PT1 was cultured in 500 ml volumes. Cultures of S. colwelliana were unsatisfactory because HGA was not stable enough in the MB media.

Cultures of SLC-PT1 were monitored until sufficient HGA had accumulated (10–15 d). The cultures were then centrifuged at 16,000×g for 10 min, and the supernatant filtered through a 0.2 μm filter. The filtrate was lyophilized and stored at −20° C. until used.

A sample of the lyophilized material (about 400 mg) was triturated with 3×8 ml of cold (0°–5° C.) methanol and filtered. The filtrate was taken to dryness by rotary evaporation and the residue was taken up in 0.5 ml of 80% methanol. For all subsequent purification steps, HPLC analyses were carried out on an Altex model 332 and eluted peaks were monitored with a Gilson Holochrome UV detector set at 282 nm. The solubilized material was put through a disposable $C_{18}$ extraction column (0.5 g; Baker) and eluted with water. After removal of the solvent, the residue (25 mg) was partially purified on another $C_{18}$ column (10×250 nm; Chromanetics) and eluted with 5% methanol in water at a flow rate of 3 ml/min. Final purification was carried out on yet another $C_{18}$ column (4.6×250 mm; Rainin) and eluted with 2% acetonitrile in water at a flow rate of 1 ml/min. The eluant from the collected peak was removed by vacuum centrifugation.

Figure 20:
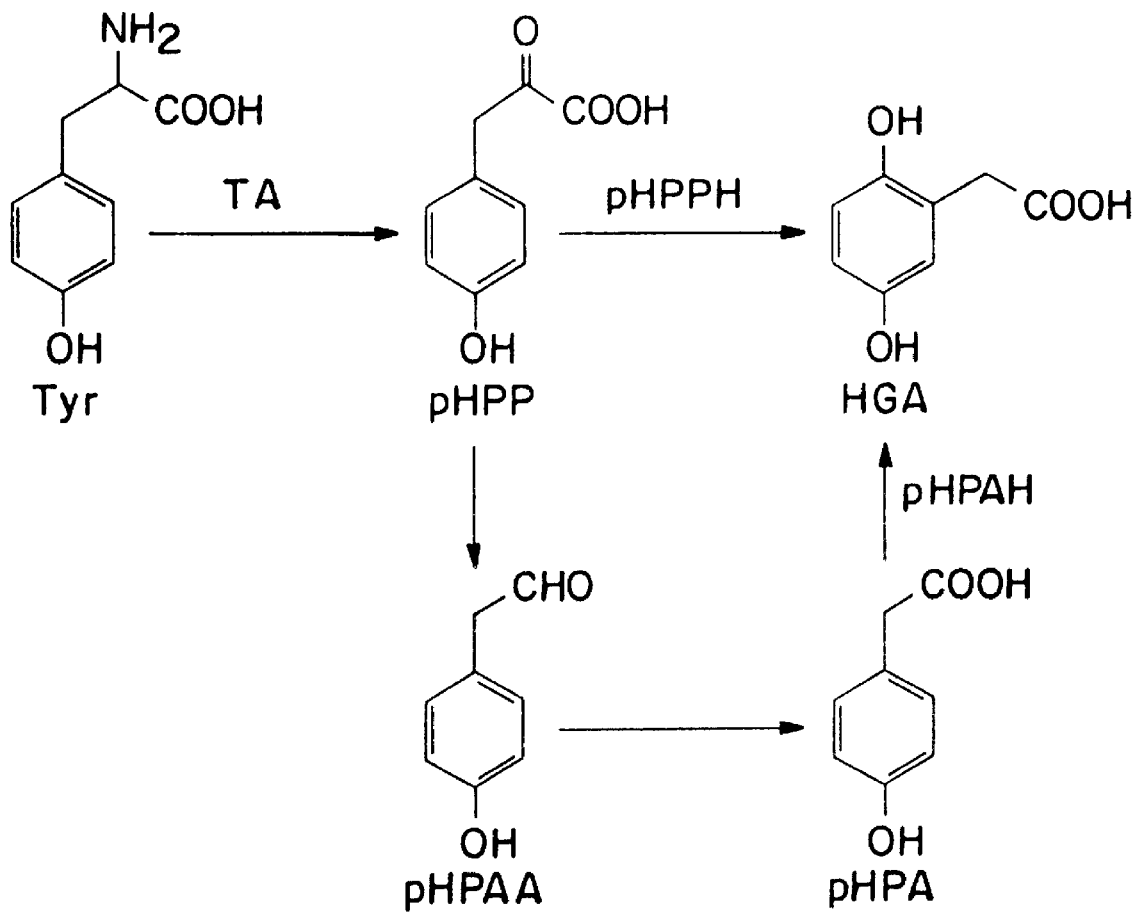
FIG. 20 shows two alternative pathways for the production of homogentisic acid from tyrosine. Substrates: Tyr, tyrosine; pHPP, p-hydroxyphenylpyruvate; pHPAA, p-hydroxyphenylacetaldehyde; pHPA, p-hydroxyphenylacetate; HGA, homogentisic acid. Enzymes: TA, transaminase; pHPPH, pHPP hydroxylase; pHPAH, pHPA hydroxylase.

Production of HGA. Lysates of S. colwelliana cells produced HGA when incubated with tyrosine (FIG. 20). In addition S. colwelliana was found to produce HGA in the culture medium (data not shown). HGA accumulated to a maximum just prior to pigmentation, after which it could no longer be detected. HGA was only a minor component of the complex MB medium. To facilitate production and characterization of HGA, the melA gene was cloned and overexpressed in E. coli. Cultures of transformed E. coli became pigmented and lysates also produced HGA (FIG. 20). Untransformed E. coli did not pigment or produce HGA (data not shown). Lysates of transformed E. coli assayed without tyrosine showed a low basal level of HGA (data not shown). The unknown contaminant SLC-PT1 also accumulated large amounts of HGA in the tyrosine/phosphate medium (FIG. 20). Maximum accumulation of HGA occurred after 10–15 days. In this media, HGA was stable for several weeks. The peaks designated as HGA from these three source were found to co-elute the mobile phase composition was modified over a range of acetonitrile. These HPLC conditions resolved HGA from many anticipated interfering compounds such as known precursors and intermediates in melanin pathways. For large-scale production of HGA, SLC-PT1 was used because of the high concentrations of HGA (up to 2 mM) which accumulated in a simple defined medium.

NMR and mass spectrometry. Analysis of the purified material by NMR spectroscopy and mass spectrometry showed it to be identical to authentic homogentisic acid: NMR $^{13}$C (100 MHz in DMSO-d$_6$) δ 36.6, 115.6, 116.8, 118.6, 123.6, 149,6, 151.0, and 176.1; $^1$H (400 MHz in DMSO-d$_6$) δ 3.51 (2H, s), 6.53 (1 H, dd, J=3.1 and 8.6 Hz), 6.60 (1H, d J=3.1 Hz), and 6.62 (1H, d, J=8.6 Hz); MS (EI-DCI, 70 eV) m/e 168 (M$^+$), 150, 122 (100%), 94.

Additional corroboration of HGA as homogentisic acid. Co-injections of the purified material with homogentisic acid showed a single peak on HPLC under two different combinations of columns and mobile phase composition. The first was a C$_{18}$ column (4.6×250 mm, Rainin) eluted with 2% acetic acid in water at 1 ml/min (retention time= 13.0 min). The second combination was a phenyl column eluted with 5% methanol in 2% acetic acid-water at 1 ml/min (retention time=7.7 min).

As shown in FIG. 21, p-OH-phenylpyruvate (pHPP) is the immediate precursor for HGA in tyrosine metabolism. Lysates of E. coli transformed with melA produced HGA when pHPP was substituted for tyrosine in the melA assay.

EXAMPLE 18

IDENTIFICATION OF HGA ACTIVITY IN Vibrio cholerae, Hyphomonas sp., AND Shewanella colwelliana Marine bacteria of the strains indicated in Table 8 were grown in Marine Broth (MB) or MB supplemented with 4 mM tyrosine (MBT) at 25° C. with vigorous aeration. Escherichia coli JM101 carrying the S. colwelliana melA gene (pMC3B) was grown at 37° C. in Luria Bertani medium supplemented with isopropylthio-β-galactoside (IPTG, 100 μg/ml) ampicillin (100 μg/ml), and 4 mM tyrosine.

TABLE 8

STRAINS

| Type[a] | Strain | Characteristics | Reference/Source |
|---|---|---|---|
| CP | V. cholerae HTX-3 | Pigmented; mutant | Ivins and Holmes (1981) |
| | S. colwelliana D | Diffusible pigment; mutant | Weiner et al. (1989) |
| | Hyphomonas MHS-3PIM | Pigmented; spontaneous mutant | Weiner et al. (1985) |
| | E. coli JM101 [pMC3B] | Pigmented; Ap$^R$ mel$^+$, melA in pUC19; clone | Fuqua et al. (1991) |
| NP | V. cholerae 569B | Non-pigmented | ATCC 25871 |
| | S. colwelliana C75 | Non-pigmented; Cm$^R$ Mel$^-$ melA::CAT19 marker replacement | Fuqua et al. (1993) |
| | Hyphomonas MHS-3 | Non-pigmented | Weiner et al. (1989) |
| | E. coli JM1O1 [pUC19] | Non-pigmented - Complementation Strain | Fuqua et al. (1991) |

[a]CP, constitutively pigmenting strains; NP, no pigment detected when grown in optimal lab media.

Pyomelanin production, estimated visually, and HGA synthesis determined electrochemically using HPLC (as described in Example 17, above), were ascertained at various times during culture on either MB or MBT media; V. cholerae 569B was also examined for pyomelanin and HGA synthesis under nutrient-limited conditions (0.125% trypton, 2.5% salt, and pH 6.4).

The presence of HPPH activity was determined from cell lysates and spent media using tyrosine as a substrate, as described in Example 17, above. In some cases, tyrosine was replaced with p-hydroxyphenylpyruvate (HPP) or p-hydroxyphenylacetate (HPA) as substrate for HPPH, with the lysates of S. colwelliana D and E. coli carrying melA.

Parallel aliquots of cell lysates were also analyzed using SDS-PAGE and Western blots on nitrocellulose. Blots were probed with a MelA-specific polyclonal antiserum generated against a MelA-LacZ, affinity-purified fusion protein, using standard methods (Fuqua, Ph.D. Thesis, University of Maryland, College Park (1991); Fuqua et al, J. Gen. Microbiol. 139:1105–1114 (1993); Fuqua et al, Gene 109:131–136 (1991)). This antibody preparation was partially purified by absorbing antibodies with Lac Z.

During growth, the constitutively hyperpigmenting variants, V. cholerae (HTX-3), S. colwelliana D, and Hyphomonas sp. (MHS-3 PIM), produced increasing amounts of red-brown water-soluble melanin with time; pigmentation was augmented by the addition of tyrosine (data not shown). E. coli JM101[pMC3B] produced pigment of similar appearance. In contrast, V. cholerae 569B, S. colwelliana C75 melA mutant, S. colwelliana W, and Hyphomonas MHS-3 E. coli JM101 [pUC 19] did not produce visible pigment at any time, consistent with previous observations (Fuqua, Ph.D. Thesis, University of Maryland, College Park (1991); Fuqua et al, J. Gen. Microbiol. 139:1105–1114 (1993); Fuqua et al, Gene 109:131–136 (1991); see Table 9).

TABLE 9

HOMOGENTISIC ACID IN THE SPENT MEDIUM OR LYSATES OF BACTERIA GROWN IN MARINE BROTH (MB) OR SUPPLEMENTED WITH TYROSINE (MBT)

| | | Homogentisic acid (HGA)[b] | | |
|---|---|---|---|---|
| | | Spent medium | | Lysate |
| Type[a] | Strains | MB | MBT | MBT |
| CP | V. cholerae HTX-3 (37° C.) | + | + | +/− |
| | V. cholerae HTX-3 (25° C.) | + | + | +/− |
| | S. colwelliana D | + | + | + |
| | Hyphomonas MHS-3 PIM | + | + | +/− |
| | E. coli JM101, IPTG [pMC3B], clone | + | + | + |
| NP | V. cholerae 569B (37° C.) | − | − | − |
| | V. cholerae 569B (25° C.) | − | − | − |
| | S. colwelliana W | − | − | − |
| | S. colwelliana C75 | − | − | − |
| | Hyphomonas MHS-3 | − | − | − |
| | E. coli JM101 [pUC19], host strain | − | − | − |

[a]CP, constitutively pigmenting strains; NP, no pigment detected when grown in optimal lab media.
[b]The presence of HGA was determined by HPLC: +, HGA detected; −, HGA not detected.

Of the non-constitutively pigmenting strains, only V. cholerae 569B produced pigment and only under nutrient-limited conditions (Coyne and Al-Harthi, Appl Environ. Microbiol. 58:2861–2865 (1992); Table 10). Both V. cholerae HTX-3 and V. cholerae 569B produced red water-soluble pigment, not phaomelanin- or eumelanin-type pigments, as previously reported.

TABLE 10

INDUCTION OF HOMOGENTISIC ACID SYNTHESIS IN V. cholerae 569B IN LIMITING NUTRIENT MEDIUM SUPPLEMENTED WITH TYROSINE[a]

| | Time | Amount of pigment produced[b] | | HGA in spent medium | |
|---|---|---|---|---|---|
| Temp. | (hrs) | −tyr | +tyr | −tyr | +tyr |
| 25° C. | 48 | − | − | − | − |
| | 72 | − | − | − | − |
| | 144 | − | + | − | + |
| 37° C. | 48 | − | ++ | − | + |
| | 72 | − | ++ | − | + |
| | 144 | − | ++ | − | + |

[a]Induction conditions (.125% trypton, 2.5% salt and pH of 6.4) were adapted from Coyne and Al-Harthi (1992).
[b]Pigment production was observed visually and scored: −, no visible pigment; +, light pink; ++, red.

Figure 22A:
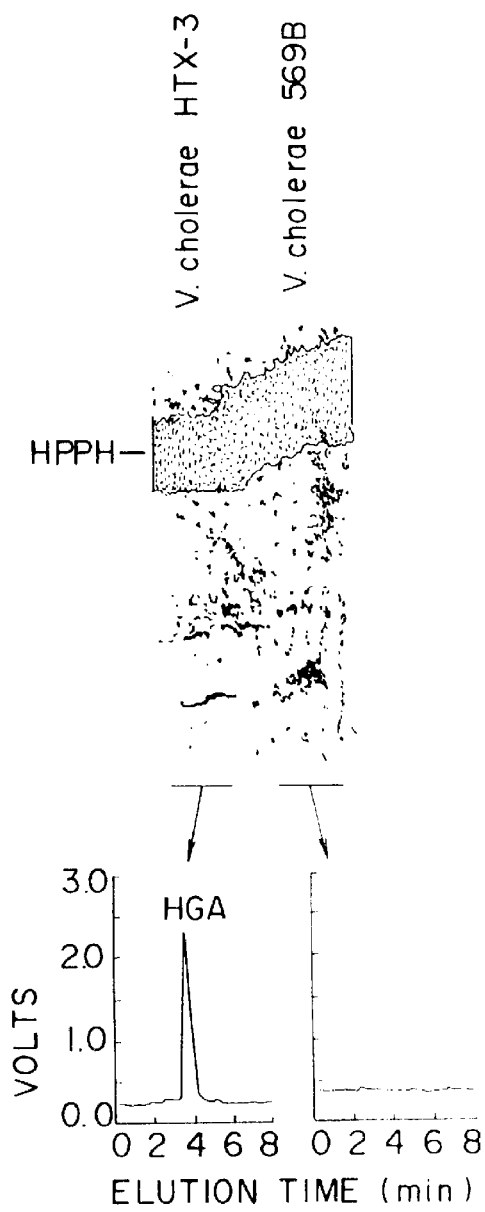
FIG. 22 shows an immunoblot for HPPH. Samples were electrophoresed in 12% SDS-PAGE, electroblotted onto Trion cellulose, and immunoblotted using purified antibody to MelA-LacZ fusion protein from S. colwelliana D. Lanes A1, B1, and C1 are hyper-pigmenting variants and Lanes A2, B2, and C2 are the corresponding non-pigmenting strains. Lanes: A1: V. cholerae HTX-3; A2: V. cholerae 569B; B1: S. colwelliana D; B2: S. colwelliana W; C1: Hyphomonas MHS-3; C2: Hyphomonas MHS-3-PIM.
Figure 22B:
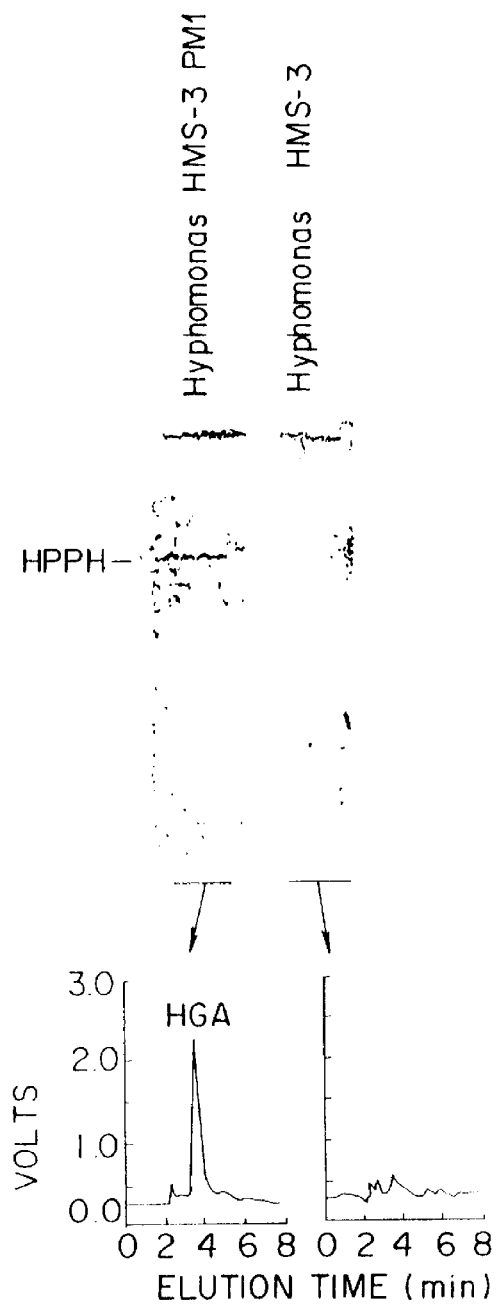
Figure 22C:
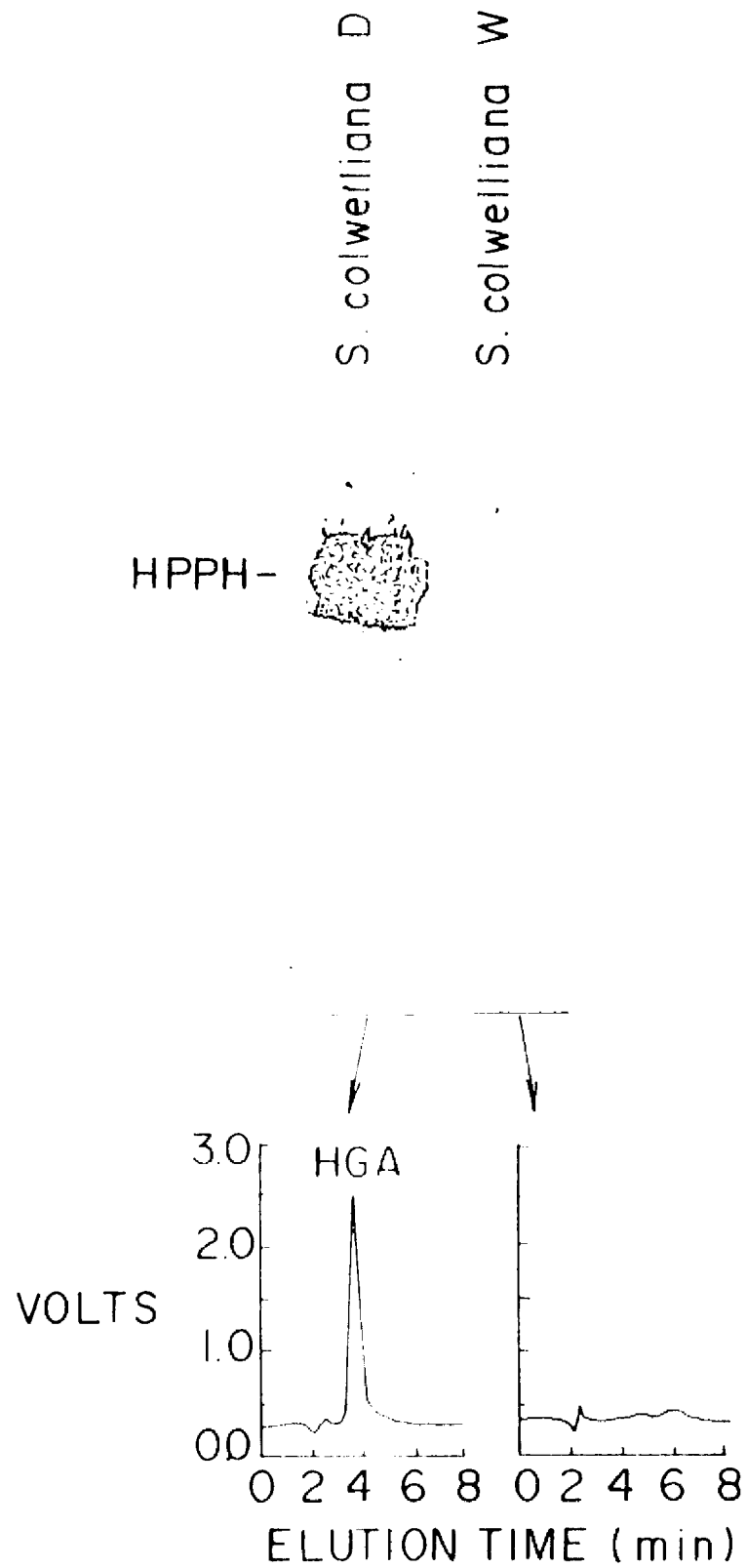

In all cases, pigment production correlated with the detection of HGA in the spent medium and cell lysates (Tables 9 and 10, FIG. 22). However, HGA was not detected in the lysate of V. cholerae 569B, but was detected in the spent medium under stress conditions. Lysates of S. colwelliana D and of E. coli containing melA produced HGA when HPP, but not HPA, were substituted for tyrosine as a substrate, consistent with the conventional pathway of tyrosine degradation in eukaryotes (Kotob et al, Abstr. 93d Ann. Meet. Am. Soc. Microbiol., p 274 (1993)).

Purified antibody to the melA-LacZ fusion protein from S. colwelliana cross-reacted with proteins synthesized by S. colwelliana D, V. cholerae HTX-3 and Hyphomonas MHS-3 PIM, all of which were pigmenting when harvested (FIG. 22). The antibody did not detect HPPH in the corresponding non-pigmenting strains. The 44 KDa protein in V. cholerae 569B (Lane A2) and the 52 KDa proteins in Hyphomonas (Lanes C1 and 2) may be cross-reacting with incompletely absorbed antibodies in the partially-purified preparation. Alternatively, it is possible that the band in lane A2 is an inactive proenzyme form of HPPH. Among the controls, there was a strong reaction to E. coli JM101[pMC3B] carrying the cloned melA gene; however, no detectable band was observed with either E. coli JM101[pUC19] and the melA mutant S. colwelliana C75 (data not shown).

The hypertoxic mutant of V. cholerae, strain HTX-3, had been reported to synthesize phaeomelanin, a red DOPA-melanin incorporating more cysteine than is incorporated into eumelanin (Ivins et al, Infect. Immun. 34:895–899 (1981). It was also reported that V. cholerae 569B produced eumelanin (DOPA-based) when subjected to stress and elevated temperature, i.e., physiological conditions that reflect those of human hosts (Coyne et al, Appl. Environ. Microbiol. 58:2861–2865 (1992). In our hands, both V. cholerae strains produced pyomelanin as determined by the solubility of the pigment, the presumptive immunoblot detection of HPPH correlating with pigmentation and, most importantly, the identification of HGA but not DOPA (Coon et al, D. Appl. Environ. Microbiol. 60:3006–3010 (1994); Fuqua, Ph.D. Thesis, University of Maryland, College Park (1991); Fuqua et al, J. Gen. Microbiol. 139:1105–1114 (1993); Fuqua et al, Gene 109:131–136 (1991)) in spent medium. These results do not unequivocally rule out the possibility that a DOPA-based melanin was also synthesized in very low quantities.

Pyomelanin production via HGA pathway has been reported in several strains of Pseudomonas (Mann, Arch. Mikrobiol. 65:359–379 (1969); Ogunnariwo et al, J. Med. Microbiol. 8:199–203 (1975); Yabuuchi et al, Int. J. Sys. Bacteriol. 22:53–64 (1972)), the marine bacteria S. colwelliana D (Coon et al, D. Appl. Environ. Microbiol. 60:3006–3010 (1994)), and other prokaryotes (Blakely, Can. J. Microbiol. 18:1247–1255 (1972).

EXAMPLE 19

ISOLATION OF HGA GENE FROM Vibrio cholerae

V. cholerae LST chromosomal DNA will be partially digested with the restriction endonuclease PstI and fragments of approximately 35 kb will be isolated. These fragments will be annealed into the cosmid vector pHC79 which will be packaged in vitro into phage lambda heads and transduced into *E. coli* recipients. Transductants will screened for HGA activity by assessing pigment properties. Any clone which exhibited heavy pigment production, similar to pigment production in *S. colwelliana,* will be isolated. A 4.2-kb PstI fragment will be subcloned into pUC19 to generate a plasmid. To verify that the insert in the clone is derived from *V. cholerae* DNA, chromosomal *V. cholerae* DNA will be extracted from the cells and analyzed by Southern blotting using the generated plasmid or the plasmid *V. cholerae* insert as the hybridization probe.

The size of the DNA insert encoding the HGA gene will be determined and a restriction map of the insert will be constructed. The insert will be subjected to deletion analysis to localize the region encoding the HGA gene. Specific restriction fragments will be deleted and the resulting plasmids will be tested for pigment production on agar plates. Any fragment in plasmid pDC1 which appears to direct melanin synthesis will be subjected to further analysis, as described in Example 3, above, in order to determine the location of the HGA open reading frame and the nucleotide sequence of the relevant fragment and the translated HGA amino acid sequence.

EXAMPLE 20

ISOLATION OF HGA GENE FROM Hyphomonas sp.

Hyphomonas sp. LST chromosomal DNA will be partially digested with the restriction endonuclease PstI and fragments of approximately 35 kb will be isolated. These fragments will be annealed into the cosmid vector pHC79 which will be packaged in vitro into phage lambda heads and transduced into E. coli recipients. Transductants will screened for HGA activity by assessing pigment properties. Any clone which exhibited heavy pigment production, similar to pigment production in S. colwelliana, will be isolated. A 4.2-kb PstI fragment will be subcloned into pUC19 to generate a plasmid. To verify that the insert in the clone is derived from V. cholerae DNA, chromosomal V. cholerae DNA will be extracted from the cells and analyzed by Southern blotting using the generated plasmid or the plasmid *V. cholerae* insert as the hybridization probe.

The size of the DNA insert encoding the HGA gene will be determined and a restriction map of the insert will be constructed. The insert will be subjected to deletion analysis to localize the region encoding the HGA gene. Specific restriction fragments will be deleted and the resulting plasmids will be tested for pigment production on agar plates. Any fragment in plasmid pDC1 which appears to direct melanin synthesis will be subjected to further analysis, as described in Example 3, above, in order to determine the location of the HGA open reading frame and the nucleotide sequence of the relevant fragment and the translated HGA amino acid sequence.

While the invention has been described and illustrated herein by references to various specific material, procedures and examples, it is understood that the invention is not restricted to the particular material, combinations of material, and procedures selected for that purpose. Numerous variations of such details can be implied as will be appreciated by those skilled in the art.

We claim:

1. A MelA isolated from a marine bacteria, wherein said bacteria is a member of the genus Shewanella, Vibrio, or Hyphomonas.

2. The MelA of claim 1 wherein said bacteria is *S. colwelliana* or *V. cholerae*.

3. The MelA of claim 1 wherein said MelA has an amino acid sequence comprising:

1 Met Ala Ser Glu Gln Ans Pro Leu Gly Leu Leu Gly Ile  Glu Phe

16 Thr Glu Phe Ala Thr Pro Asp Leu Asp Phe Met His Lys Val Phe

31 Ile Asp Phe Gly Phe Ser Lys Leu Lys Lys His Lys Gln Lys Asp

46 Ile Val Tyr Tyr Lys Gln Asn Asp Ile  Asn Phe Leu Leu Asn Asn

61 Glu Lys Gln Gly Phe Ser Ala Gln Phe Ala Lys Thr His Gly Pro

76 Ala Ile  Ser Ser Met Gly Trp Arg Val Glu Asp Ala Asn Phe Ala

91 Phe Glu Gly Ala Val Ala Arg Gly Ala Lys Pro Ala Ala Asp Glu

| | |
|---|---|
| 106 | Val Lys Asp Leu Pro Tyr Pro Ala Ile Tyr Gly Ile Gly Asp Ser |
| 121 | Leu Ile Tyr Phe Ile Asp Thr Phe Gly Asp Asp Asn Asn Ile Tyr |
| 136 | Thr Ser Asp Phe Glu Ala Leu Asp Glu Pro Ile Ile Thr Gln Glu |
| 151 | Lys Gly Phe Ile Glu Val Asp His Leu Thr Asn Asn Val His Lys |
| 166 | Gly Thr Met Glu Tyr Trp Ser Asn Phe Tyr Lys Asp Ile Phe Gly |
| 181 | Phe Thr Glu Val Arg Tyr Phe Asp Ile Lys Gly Ser Gln Thr Ala |
| 196 | Leu Ile Ser Tyr Ala Leu Arg Ser Pro Asp Gly Ser Phe Cys Ile |
| 211 | Pro Ile Asn Glu Gly Lys Gly Asp Asp Arg Asn Gln Ile Asp Glu |
| 226 | Tyr Leu Lys Glu Tyr Asp Gly Pro Gly Val Gln His Leu Ala Phe |
| 241 | Arg Ser Arg Asp Ile Val Ala Ser Leu Asp Ala Met Glu Gly Ser |
| 256 | Ser Ile Gln Thr Leu Asp Ile Ile Pro Glu Tyr Tyr Asp Thr Ile |
| 271 | Phe Glu Lys Leu Pro Gln Val Thr Glu Asp Arg Asp Arg Ile Lys |
| 286 | His His Gln Ile Leu Val Asp Gly Asp Glu Asp Gly Tyr Leu Leu |
| 301 | Gln Ile Phe Thr Lys Asn Leu Phe Gly Pro Ile Phe Ile Glu Ile |
| 316 | Ile Gln Arg Lys Asn Asn Leu Gly Phe Gly Glu Gly Ans Phe Lys |
| 331 | Ala Leu Phe Glu Ser Ile Glu Arg Asp Gln Val Arg Arg Gly Val |
| 346 | Leu (SEQ ID NO:2) | or biologically active fragment thereof retaining p-hydroxyphenylpyruvate hydroxylase activity.

4. The MelA of claim 1 wherein said MelA is recombinant.

5. The biologically active fragment of claim 3, wherein said fragment is produced by enzymatic digestion with trypsin, chymotrypsin, pepsin, subtilisin, V8 protease or mixtures thereof.

6. A composition for protecting the skin against ultraviolet rays, comprising an effective amount of the MelA of claim 1 and a pharmaceutically acceptable vehicle.

7. A pigment composition comprising the MelA of claim 1.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 1434 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 316..1353

( x i ) SEQUENCE DESCRIPTION: SEQ ID NO:1:

```
TGACTTTATG AGTCGCACAG GTTCGAAGCG GGCTACATGA CCTTACATCA AAAAGGCGTG      60

GCCGCATGGA CCACAACCTG GTCGTACTGA AGCCTCAGTG GGCAAAACTG AAACCTATGA     120

GTATGCAGTA ATGGTGGACA CCTTTGCACC ACTGCAACTG ACCCAGCATG TCAATCGTGC     180

ATGAGCAAAG ATTACAACCG TTCCTGGCTA GAAGAGTAAA AGCGTTCAGC CAGTGCTGAA     240

CATCTAATAA ATATAACACC AGAGGTGACA CCGAAGAGTG CCCTTGGTTG CAATAAGTTG     300

AAAGAGGATA ATTAC ATG GCA AGC GAA CAA AAC CCA CTG GGT CTA CTT GGT      351
                 Met Ala Ser Glu Gln Asn Pro Leu Gly Leu Leu Gly
                  1               5                  10

ATC GAA TTC ACT GAA TTT GCT ACA CCA GAT CTA GAT TTT ATG CAT AAA      399
Ile Glu Phe Thr Glu Phe Ala Thr Pro Asp Leu Asp Phe Met His Lys
         15                  20                  25

GTT TTT ATC GAC TTT GGT TTC TCA AAA CTT AAA AAA CAC AAG CAG AAA      447
Val Phe Ile Asp Phe Gly Phe Ser Lys Leu Lys Lys His Lys Gln Lys
    30                  35                  40

GAT ATT GTT TAC TAT AAA CAA AAT GAT ATT AAC TTT TTA CTC AAA ATG      495
Asp Ile Val Tyr Tyr Lys Gln Asn Asp Ile Asn Phe Leu Leu Lys Met
 45                  50                  55                  60
```

-continued

```
AAA  AAA  CAG  GGC  TTT  TCA  GCC  CAG  TTT  GCC  AAA  ACG  CAT  GGC  CCA  GCC        543
Lys  Lys  Gln  Gly  Phe  Ser  Ala  Gln  Phe  Ala  Lys  Thr  His  Gly  Pro  Ala
               65                  70                            75

ATT  AGT  TCT  ATG  GGC  TGG  CGT  GTA  GAA  GAT  GCC  AAC  TTT  GCC  TTT  GAA        591
Ile  Ser  Ser  Met  Gly  Trp  Arg  Val  Glu  Asp  Ala  Asn  Phe  Ala  Phe  Glu
               80                  85                            90

GGT  GCT  GTA  GCC  CGT  GGG  GCT  AAA  CCC  GCA  GCA  GAT  GAG  GTG  AAA  GAT        639
Gly  Ala  Val  Ala  Arg  Gly  Ala  Lys  Pro  Ala  Ala  Asp  Glu  Val  Lys  Asp
               95                  100                           105

CTT  CCC  TAT  CCC  GCT  ATC  TAT  GGC  ATT  GGT  GAC  AGC  CTT  ATC  TAC  TTT        687
Leu  Pro  Tyr  Pro  Ala  Ile  Tyr  Gly  Ile  Gly  Asp  Ser  Leu  Ile  Tyr  Phe
     110                 115                      120

ATC  GAT  ACG  TTT  GGC  GAT  GAC  AAC  AAT  ATC  TAC  ACT  TCT  GAT  TTT  GAA        735
Ile  Asp  Thr  Phe  Gly  Asp  Asp  Asn  Asn  Ile  Tyr  Thr  Ser  Asp  Phe  Glu
125                      130                      135                      140

GCG  TTA  GAT  GAG  CCT  ATC  ATC  ACC  CAA  GAG  AAA  GGC  TTC  ATT  GAG  GTC        783
Ala  Leu  Asp  Glu  Pro  Ile  Ile  Thr  Gln  Glu  Lys  Gly  Phe  Ile  Glu  Val
               145                 150                           155

GAC  CAT  CTC  ACC  AAT  AAT  GTC  CAT  AAG  GGC  ACC  ATG  GAA  TAT  TGG  TCA        831
Asp  His  Leu  Thr  Asn  Asn  Val  His  Lys  Gly  Thr  Met  Glu  Tyr  Trp  Ser
          160                      165                      170

AAC  TTC  TAC  AAA  GAC  ATT  TTT  GGC  TTT  ACA  GAA  GTG  CGT  TAC  TTC  GAC        879
Asn  Phe  Tyr  Lys  Asp  Ile  Phe  Gly  Phe  Thr  Glu  Val  Arg  Tyr  Phe  Asp
          175                      180                      185

ATT  AAG  GGC  TCA  CAA  ACA  GCT  CTT  ATC  TCT  TAC  GCC  CTG  CGC  TCG  CCA        927
Ile  Lys  Gly  Ser  Gln  Thr  Ala  Leu  Ile  Ser  Tyr  Ala  Leu  Arg  Ser  Pro
     190                 195                      200

GAT  GGT  AGT  TTC  TGC  ATT  CCA  ATT  AAC  GAA  GGC  AAA  GGC  GAT  GAT  CGT        975
Asp  Gly  Ser  Phe  Cys  Ile  Pro  Ile  Asn  Glu  Gly  Lys  Gly  Asp  Asp  Arg
205                      210                      215                      220

AAC  CAA  ATT  GAT  GAG  TAC  TTA  AAA  GAG  TAC  GAT  GGC  CCA  GGT  GTC  CAA       1023
Asn  Gln  Ile  Asp  Glu  Tyr  Leu  Lys  Glu  Tyr  Asp  Gly  Pro  Gly  Val  Gln
               225                 230                           235

CAC  TTA  GCG  TTC  CGT  AGC  CGC  GAC  ATA  GTT  GCC  TCA  CTG  GAT  GCC  ATG       1071
His  Leu  Ala  Phe  Arg  Ser  Arg  Asp  Ile  Val  Ala  Ser  Leu  Asp  Ala  Met
               240                 245                           250

GAA  GGA  AGC  TCC  ATT  CAA  ACC  TTG  GAC  ATA  ATT  CCA  GAG  TAT  TAC  GAC       1119
Glu  Gly  Ser  Ser  Ile  Gln  Thr  Leu  Asp  Ile  Ile  Pro  Glu  Tyr  Tyr  Asp
          255                      260                      265

ACT  ATC  TTT  GAA  AAG  CTG  CCT  CAA  GTC  ACT  GAA  GAC  AGA  GAT  CGC  ATC       1167
Thr  Ile  Phe  Glu  Lys  Leu  Pro  Gln  Val  Thr  Glu  Asp  Arg  Asp  Arg  Ile
     270                 275                      280

AAG  CAT  CAT  CAA  ATC  CTG  GTA  GAT  GGC  GAT  GAA  GAT  GGC  TAC  TTA  CTG       1215
Lys  His  His  Gln  Ile  Leu  Val  Asp  Gly  Asp  Glu  Asp  Gly  Tyr  Leu  Leu
285                      290                      295                      300

CAA  ATT  TTC  ACC  AAA  AAT  CTA  TTT  GGT  CCA  ATT  TTT  ATC  GAA  ATC  ATC       1263
Gln  Ile  Phe  Thr  Lys  Asn  Leu  Phe  Gly  Pro  Ile  Phe  Ile  Glu  Ile  Ile
               305                 310                           315

CAG  CGT  AAA  AAC  AAT  CTC  GGT  TTT  GGC  GAA  GGT  AAT  TTT  AAA  GCC  CTA       1311
Gln  Arg  Lys  Asn  Asn  Leu  Gly  Phe  Gly  Glu  Gly  Asn  Phe  Lys  Ala  Leu
               320                 325                           330

TTT  GAA  TCG  ATT  GAG  CGT  GAT  CAG  GTG  CGT  CGC  GGC  GTA  CTC                 1353
Phe  Glu  Ser  Ile  Glu  Arg  Asp  Gln  Val  Arg  Arg  Gly  Val  Leu
               335                 340                           345

TAACAATCAC  CCAGTGATCC  AACCTCAAAA  AACCAGCATC  GCGCTGGTTT  TTTTATTGCA             1413

GCACAACAAT  AAACCTCTAC  A                                                          1434
```

( 2 ) INFORMATION FOR SEQ ID NO:2:

( i ) SEQUENCE CHARACTERISTICS:

(A) LENGTH: 346 amino acids
(B) TYPE: amino acid
(D) TOPOLOGY: linear (ii) MOLECULE TYPE: protein (xi) SEQUENCE DESCRIPTION: SEQ ID NO:2:

```
Met Ala Ser Glu Gln Asn Pro Leu Gly Leu Leu Gly Ile Glu Phe Thr
 1               5                  10                  15
Glu Phe Ala Thr Pro Asp Leu Asp Phe Met His Lys Val Phe Ile Asp
                20                  25                  30
Phe Gly Phe Ser Lys Leu Lys Lys His Lys Gln Lys Asp Ile Val Tyr
                35                  40                  45
Tyr Lys Gln Asn Asp Ile Asn Phe Leu Leu Lys Met Lys Lys Gln Gly
     50                  55                  60
Phe Ser Ala Gln Phe Ala Lys Thr His Gly Pro Ala Ile Ser Ser Met
 65                  70                  75                  80
Gly Trp Arg Val Glu Asp Ala Asn Phe Ala Phe Glu Gly Ala Val Ala
                85                  90                  95
Arg Gly Ala Lys Pro Ala Ala Asp Glu Val Lys Asp Leu Pro Tyr Pro
                100                 105                 110
Ala Ile Tyr Gly Ile Gly Asp Ser Leu Ile Tyr Phe Ile Asp Thr Phe
                115                 120                 125
Gly Asp Asp Asn Asn Ile Tyr Thr Ser Asp Phe Glu Ala Leu Asp Glu
    130                 135                 140
Pro Ile Ile Thr Gln Glu Lys Gly Phe Ile Glu Val Asp His Leu Thr
145                 150                 155                 160
Asn Asn Val His Lys Gly Thr Met Glu Tyr Trp Ser Asn Phe Tyr Lys
                165                 170                 175
Asp Ile Phe Gly Phe Thr Glu Val Arg Tyr Phe Asp Ile Lys Gly Ser
                180                 185                 190
Gln Thr Ala Leu Ile Ser Tyr Ala Leu Arg Ser Pro Asp Gly Ser Phe
                195                 200                 205
Cys Ile Pro Ile Asn Glu Gly Lys Gly Asp Asp Arg Asn Gln Ile Asp
                210                 215                 220
Glu Tyr Leu Lys Glu Tyr Asp Gly Pro Gly Val Gln His Leu Ala Phe
225                 230                 235                 240
Arg Ser Arg Asp Ile Val Ala Ser Leu Asp Ala Met Glu Gly Ser Ser
                245                 250                 255
Ile Gln Thr Leu Asp Ile Ile Pro Glu Tyr Tyr Asp Thr Ile Phe Glu
                260                 265                 270
Lys Leu Pro Gln Val Thr Glu Asp Arg Asp Arg Ile Lys His His Gln
                275                 280                 285
Ile Leu Val Asp Gly Asp Glu Asp Gly Tyr Leu Leu Gln Ile Phe Thr
    290                 295                 300
Lys Asn Leu Phe Gly Pro Ile Phe Ile Glu Ile Ile Gln Arg Lys Asn
305                 310                 315                 320
Asn Leu Gly Phe Gly Glu Gly Asn Phe Lys Ala Leu Phe Glu Ser Ile
                325                 330                 335
Glu Arg Asp Gln Val Arg Arg Gly Val Leu
                340                 345
```

(2) INFORMATION FOR SEQ ID NO:3:

(i) SEQUENCE CHARACTERISTICS:
(A) LENGTH: 30 base pairs
(B) TYPE: nucleic acid ( C ) STRANDEDNESS: single
( D ) TOPOLOGY: linear ( i i ) MOLECULE TYPE: other nucleic acid
  ( A ) DESCRIPTION: /desc = "PRIMER"

( i i i ) HYPOTHETICAL: NO ( i v ) ANTI-SENSE: NO ( x i ) SEQUENCE DESCRIPTION: SEQ ID NO:3:

GTTTTGTTCG CTTGCCATGT AATTATCCTC                30

( 2 ) INFORMATION FOR SEQ ID NO:4:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

ATCGTAACCA AATTGATGAG T                         21

( 2 ) INFORMATION FOR SEQ ID NO:5:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

GGGGATCCGT CGACCTGCAG CC                        22

( 2 ) INFORMATION FOR SEQ ID NO:6:

( i ) SEQUENCE CHARACTERISTICS:
  ( A ) LENGTH: 720 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: CDS
  ( B ) LOCATION: 167..628

( x i ) SEQUENCE DESCRIPTION: SEQ ID NO:6:

AAAAACCAGC ATCGCGCTGG TTTTTTTATT GCAGCACAAC AATAAACCTC TACACTAGCA     60

CACTTAATTA TCTACTCACT GGCCTAACGC TTTCATGTCA GAACATATTC TCATTGCGGT    120

ATTTTTACCG ACCTTTTTTT TCGTCTCAAT TACACCAGGT ATGTGT ATG ACA CTG       175
                                                  Met Thr Leu

```
GCC ATG ACT CTC GGT ATG AGT ATC GGT GTG CGC CGA ACC TTA TGG ATG        223
Ala Met Thr Leu Gly Met Ser Ile Gly Val Arg Arg Thr Leu Trp Met
350                     355                 360                 365

ATG GTT GGT GAG CTA GCA GGC GTT GCC CTC GTG GCG ATT GCC GCC GTA        271
Met Val Gly Glu Leu Ala Gly Val Ala Leu Val Ala Ile Ala Ala Val
                370                 375                 380

ATG GGT GTC GCC AGT ATG ATG CTG AAC TAT CCA CAA CTC TTC GAT ATT        319
Met Gly Val Ala Ser Met Met Leu Asn Tyr Pro Gln Leu Phe Asp Ile
            385                 390                 395

TTA AAA TGG GTC GGT GGG CTC TAT CTT GGT TAC ATC GGC ATT AGC ATG        367
Leu Lys Trp Val Gly Gly Leu Tyr Leu Gly Tyr Ile Gly Ile Ser Met
        400                 405                 410

TGG CGG GCC AAA GGG AAA ATG GCC AAC CTT GAC AAT ACC TCC AGT CAG        415
Trp Arg Ala Lys Gly Lys Met Ala Asn Leu Asp Asn Thr Ser Ser Gln
    415                 420                 425

ATC AGT AAT CGA GCG CTA ATA ACT CAA GGC TTT GTC ACC GCA ATT GCT        463
Ile Ser Asn Arg Ala Leu Ile Thr Gln Gly Phe Val Thr Ala Ile Ala
430                 435                 440                 445

AAT CCA AAA GGC TGG GCC TTT ATG ATC TCG CTG CTC CCC CCT TTT ATC        511
Asn Pro Lys Gly Trp Ala Phe Met Ile Ser Leu Leu Pro Pro Phe Ile
                450                 455                 460

AGC GTT GAC CAA GCG ATT GCA CCA CAA TTA ATG GTA TTA CTG TCA ATT        559
Ser Val Asp Gln Ala Ile Ala Pro Gln Leu Met Val Leu Leu Ser Ile
            465                 470                 475

ATT ATG ATG ACA GAG TTC TTC AGC ATG CTT GCT TAT GCG AGC GGC GGA        607
Ile Met Met Thr Glu Phe Phe Ser Met Leu Ala Tyr Ala Ser Gly Gly
        480                 485                 490

AAA CCC TTA AAC TGT TTT TAA GTCGAGGCGA TAACATCAAG TGGATGAACC           658
Lys Pro Leu Asn Cys Phe *
    495                 500

GCATAGCAGG GAGTTTAATG ATCTGTGTTG CTTATGGTT GGCGCTAGGT TAACGCAGAG       718

T C                                                                    720
```

(2) INFORMATION FOR SEQ ID NO:7:

(i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO:7:

```
Met Thr Leu Ala Met Thr Leu Gly Met Ser Ile Gly Val Arg Arg Thr
1               5                   10                  15

Leu Trp Met Met Val Gly Glu Leu Ala Gly Val Ala Leu Val Ala Ile
            20                  25                  30

Ala Ala Val Met Gly Val Ala Ser Met Met Leu Asn Tyr Pro Gln Leu
        35                  40                  45

Phe Asp Ile Leu Lys Trp Val Gly Gly Leu Tyr Leu Gly Tyr Ile Gly
    50                  55                  60

Ile Ser Met Trp Arg Ala Lys Gly Lys Met Ala Asn Leu Asp Asn Thr
65                  70                  75                  80

Ser Ser Gln Ile Ser Asn Arg Ala Leu Ile Thr Gln Gly Phe Val Thr
                85                  90                  95

Ala Ile Ala Asn Pro Lys Gly Trp Ala Phe Met Ile Ser Leu Leu Pro
            100                 105                 110

Pro Phe Ile Ser Val Asp Gln Ala Ile Ala Pro Gln Leu Met Val Leu
        115                 120                 125
```

```
Leu  Ser  Ile  Ile  Met  Met  Thr  Glu  Phe  Phe  Ser  Met  Leu  Ala  Tyr  Ala
     130                 135                      140

Ser  Gly  Gly  Lys  Pro  Leu  Asn  Cys  Phe
145                      150
```

( 2 ) INFORMATION FOR SEQ ID NO:8:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "POLYLINKER"

( i i i ) HYPOTHETICAL: NO ( i v ) ANTI-SENSE: NO ( x i ) SEQUENCE DESCRIPTION: SEQ ID NO:8:

```
GTGAATTCGA  GCTCGGTACC  CGGGGATCCT  CTAGAGTTGC  ATGCCTGCAG  GTC                53
```

( 2 ) INFORMATION FOR SEQ ID NO:9:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "POLYLINKER"

( i i i ) HYPOTHETICAL: NO ( i v ) ANTI-SENSE: NO ( x i ) SEQUENCE DESCRIPTION: SEQ ID NO:9:

```
GACTCTAGAG  GATCCCCGGG  TACCGGACCT  GCAGGCATGC  AAGCTT                         46
```

( 2 ) INFORMATION FOR SEQ ID NO:10:

( i ) SEQUENCE CHARACTERISTICS:
        ( A ) LENGTH: 346 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: S. colwelliana
        ( B ) STRAIN: D ( x i ) SEQUENCE DESCRIPTION: SEQ ID NO:10:

```
Met  Ala  Ser  Glu  Gln  Asn  Pro  Leu  Gly  Leu  Leu  Gly  Ile  Glu  Phe  Thr
1                   5                        10                      15

Glu  Phe  Ala  Thr  Pro  Asp  Leu  Asp  Phe  Met  His  Lys  Val  Phe  Ile  Asp
               20                  25                       30

Phe  Gly  Phe  Ser  Lys  Leu  Lys  Lys  His  Lys  Gln  Lys  Asp  Ile  Val  Tyr
          35                       40                       45

Tyr  Lys  Gln  Asn  Asp  Ile  Asn  Phe  Leu  Leu  Asn  Asn  Glu  Lys  Gln  Gly
     50                       55                       60

Phe  Ser  Ala  Gln  Phe  Ala  Lys  Thr  His  Gly  Pro  Ala  Ile  Ser  Ser  Met
```

|     |     |     |     | 65  |     |     |     |     | 70  |     |     |     |     | 75  |     |     |     |     | 80  |
|-----|-----|-----|-----|-----|-----|-----|-----|-----|-----|-----|-----|-----|-----|-----|-----|-----|-----|-----|-----|
| Gly | Trp | Arg | Val | Glu | Asp | Ala | Asn | Phe | Ala | Phe | Glu | Gly | Ala | Val | Ala |
|     |     |     |     | 85  |     |     |     |     | 90  |     |     |     |     | 95  |     |
| Arg | Gly | Ala | Lys | Pro | Ala | Ala | Asp | Glu | Val | Lys | Asp | Leu | Pro | Tyr | Pro |
|     |     |     | 100 |     |     |     |     | 105 |     |     |     | 110 |     |     |     |
| Ala | Ile | Tyr | Gly | Ile | Gly | Asp | Ser | Leu | Ile | Tyr | Phe | Ile | Asp | Thr | Phe |
|     |     | 115 |     |     |     | 120 |     |     |     |     |     | 125 |     |     |     |
| Gly | Asp | Asp | Asn | Asn | Ile | Tyr | Thr | Ser | Asp | Phe | Glu | Ala | Leu | Asp | Glu |
|     | 130 |     |     |     |     | 135 |     |     |     |     | 140 |     |     |     |     |
| Pro | Ile | Ile | Thr | Gln | Glu | Lys | Gly | Phe | Ile | Glu | Val | Asp | His | Leu | Thr |
| 145 |     |     |     |     | 150 |     |     |     |     | 155 |     |     |     |     | 160 |
| Asn | Asn | Val | His | Lys | Gly | Thr | Met | Glu | Tyr | Trp | Ser | Asn | Phe | Tyr | Lys |
|     |     |     |     | 165 |     |     |     |     | 170 |     |     |     |     | 175 |     |
| Asp | Ile | Phe | Gly | Phe | Thr | Glu | Val | Arg | Tyr | Phe | Asp | Ile | Lys | Gly | Ser |
|     |     |     | 180 |     |     |     |     | 185 |     |     |     |     | 190 |     |     |
| Gln | Thr | Ala | Leu | Ile | Ser | Tyr | Ala | Leu | Arg | Ser | Pro | Asp | Gly | Ser | Phe |
|     |     | 195 |     |     |     |     | 200 |     |     |     |     | 205 |     |     |     |
| Cys | Ile | Pro | Ile | Asn | Glu | Gly | Lys | Gly | Asp | Asp | Arg | Asn | Gln | Ile | Asp |
|     | 210 |     |     |     |     | 215 |     |     |     |     | 220 |     |     |     |     |
| Glu | Tyr | Leu | Lys | Glu | Tyr | Asp | Gly | Pro | Gly | Val | Gln | His | Leu | Ala | Phe |
| 225 |     |     |     |     | 230 |     |     |     |     | 235 |     |     |     |     | 240 |
| Arg | Ser | Arg | Asp | Ile | Val | Ala | Ser | Leu | Asp | Ala | Met | Glu | Gly | Ser | Ser |
|     |     |     |     | 245 |     |     |     |     | 250 |     |     |     |     | 255 |     |
| Ile | Gln | Thr | Leu | Asp | Ile | Ile | Pro | Glu | Tyr | Tyr | Asp | Thr | Ile | Phe | Glu |
|     |     |     | 260 |     |     |     |     | 265 |     |     |     |     | 270 |     |     |
| Lys | Leu | Pro | Gln | Val | Thr | Glu | Asp | Arg | Asp | Arg | Ile | Lys | His | His | Gln |
|     |     | 275 |     |     |     |     | 280 |     |     |     |     | 285 |     |     |     |
| Ile | Leu | Val | Asp | Gly | Asp | Glu | Asp | Gly | Tyr | Leu | Leu | Gln | Ile | Phe | Thr |
|     |     | 290 |     |     |     |     | 295 |     |     |     |     | 300 |     |     |     |
| Lys | Asn | Leu | Phe | Gly | Pro | Ile | Phe | Ile | Glu | Ile | Ile | Gln | Arg | Lys | Asn |
| 305 |     |     |     |     | 310 |     |     |     |     | 315 |     |     |     |     | 320 |
| Asn | Leu | Gly | Phe | Gly | Glu | Gly | Asn | Phe | Lys | Ala | Leu | Phe | Glu | Ser | Ile |
|     |     |     |     | 325 |     |     |     |     | 330 |     |     |     |     | 335 |     |
| Glu | Arg | Asp | Gln | Val | Arg | Arg | Gly | Val | Leu |
|     |     |     | 340 |     |     |     |     | 345 |     |     |

( 2 ) INFORMATION FOR SEQ ID NO:11:

( i ) SEQUENCE CHARACTERISTICS:
       ( A ) LENGTH: 357 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
       ( A ) ORGANISM: PSEUDOMONAS pHPPH ( x i ) SEQUENCE DESCRIPTION: SEQ ID NO:11:

| Ala | Asp | Leu | Tyr | Glu | Asn | Pro | Met | Gly | Leu | Met | Gly | Phe | Glu | Phe | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Glu | Leu | Ala | Ser | Pro | Thr | Pro | Asn | Thr | Leu | Glu | Pro | Ile | Phe | Glu | Ile |
|     |     |     | 20  |     |     |     |     | 25  |     |     |     |     | 30  |     |     |
| Met | Gly | Phe | Thr | Lys | Val | Ala | Thr | His | Arg | Ser | Lys | Asp | Val | His | Leu |

-continued

|  | | 35 | | | | 40 | | | | | 45 | | | |
|---|---|---|---|---|---|---|---|---|---|---|---|---|---|---|
| Tyr | Arg 50 | Gln | Gly | Ala | Ile 55 | Asn | Leu | Ile | Leu | Asn 60 | Asn | Glu | Pro | His | Ser |
| Val 65 | Ala | Ser | Tyr | Phe 70 | Ala | Ala | Glu | His | Gly | Pro 75 | Ser | Val | Cys | Gly | Met 80 |
| Ala | Phe | Arg | Val | Lys 85 | Asp | Ser | Gln | Lys | Ala 90 | Tyr | Lys | Arg | Ala | Leu 95 | Glu |
| Leu | Gly | Ala | Gln 100 | Pro | Ile | His | Ile | Glu 105 | Thr | Gly | Pro | Met | Glu 110 | Leu | Asn |
| Leu | Pro | Ala 115 | Ile | Lys | Gly | Ile | Gly 120 | Gly | Ala | Pro | Leu | Tyr 125 | Leu | Ile | Asp |
| Arg | Phe 130 | Gly | Glu | Gly | Ser | Ser 135 | Ile | Tyr | Asp | Ile | Asp 140 | Phe | Val | Phe | Leu |
| Glu 145 | Gly | Val | Asp | Arg | His 150 | Pro | Val | Gly | Ala | Gly 155 | Leu | Lys | Ile | Ile | Asp 160 |
| His | Leu | Thr | His | Asn 165 | Val | Tyr | Arg | Gly | Arg 170 | Met | Ala | Tyr | Trp | Ala 175 | Asn |
| Phe | Tyr | Glu | Lys 180 | Leu | Phe | Asn | Phe | Arg 185 | Glu | Ile | Arg | Tyr | Phe 190 | Asp | Ile |
| Lys | Gly | Glu 195 | Tyr | Thr | Gly | Leu | Thr 200 | Ser | Lys | Ala | Met | Thr 205 | Ala | Pro | Asp |
| Gly | Met 210 | Ile | Arg | Ile | Pro | Leu 215 | Asn | Glu | Glu | Ser | Ser 220 | Lys | Gly | Ala | Gly |
| Gln 225 | Ile | Glu | Glu | Phe | Leu 230 | Met | Gln | Phe | Asn | Gly 235 | Glu | Gly | Ile | Gln | His 240 |
| Val | Ala | Phe | Leu | Ser 245 | Asp | Asp | Leu | Ile | Lys 250 | Thr | Trp | Asp | His | Leu 255 | Lys |
| Ser | Ile | Gly | Met 260 | Arg | Phe | Met | Thr | Ala 265 | Pro | Pro | Asp | Thr | Tyr 270 | Tyr | Glu |
| Met | Leu | Glu 275 | Gly | Arg | Leu | Pro | Asn 280 | His | Gly | Glu | Pro | Val 285 | Gly | Glu | Leu |
| Gln | Ala 290 | Arg | Gly | Ile | Leu | Leu 295 | Asp | Gly | Ser | Ser | Glu 300 | Ser | Gly | Asp | Lys |
| Arg 305 | Leu | Leu | Leu | Gln | Ile 310 | Phe | Ser | Glu | Thr | Leu 315 | Met | Gly | Pro | Val | Phe 320 |
| Phe | Glu | Phe | Ile | Gln 325 | Arg | Lys | Gly | Asp | Asp 330 | Gly | Phe | Gly | Glu | Gly 335 | Asn |
| Phe | Lys | Ala | Leu 340 | Phe | Glu | Ser | Ile | Glu 345 | Arg | Asp | Gln | Val | Arg 350 | Arg | Gly |
| Val | Leu | Ser 355 | Thr | Asp |  | | | | | | | | | | |